United States Patent
Tanaka et al.

(10) Patent No.: US 9,994,538 B2
(45) Date of Patent: Jun. 12, 2018

(54) LATENT ACIDS AND THEIR USE

(71) Applicant: BASF SE, Ludwigshafen (DE)

(72) Inventors: Keita Tanaka, Nishinomiya (JP); Yuki Matsuoka, Nishinomiya (JP); Kazuhiko Kunimoto, Kawanishi (JP); Toshikage Asakura, Minoo (JP); Hisatoshi Kura, Takarazuka (JP)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/546,699

(22) PCT Filed: Jan. 29, 2016

(86) PCT No.: PCT/EP2016/051912
§ 371 (c)(1),
(2) Date: Jul. 27, 2017

(87) PCT Pub. No.: WO2016/124493
PCT Pub. Date: Aug. 11, 2016

(65) Prior Publication Data
US 2018/0009775 A1 Jan. 11, 2018

(30) Foreign Application Priority Data
Feb. 2, 2015 (EP) .................................... 15153404

(51) Int. Cl.
| C07D 307/52 | (2006.01) |
| C07D 311/16 | (2006.01) |
| G03F 7/039 | (2006.01) |
| G03F 7/004 | (2006.01) |
| G03F 7/038 | (2006.01) |

(52) U.S. Cl.
CPC .......... C07D 307/52 (2013.01); C07D 311/16 (2013.01); G03F 7/0045 (2013.01); G03F 7/0046 (2013.01); G03F 7/038 (2013.01); G03F 7/039 (2013.01)

(58) Field of Classification Search
CPC ... C07D 307/52; C07D 311/16; G03F 7/0045; G03F 7/0046; G03F 7/038; G03F 7/039
See application file for complete search history.

(56) References Cited

U.S. PATENT DOCUMENTS

| 3,018,262 A | 1/1962 | Schroeder |
| 3,117,099 A | 1/1964 | Proops et al. |
| 4,017,652 A | 4/1977 | Gruber |
| 4,026,705 A | 5/1977 | Crivello et al. |
| 4,069,954 A | 1/1978 | Rauch |
| 4,282,309 A | 8/1981 | Laridon et al. |
| 4,299,938 A | 11/1981 | Green et al. |
| 4,339,567 A | 7/1982 | Green et al. |
| 4,366,228 A | 12/1982 | Specht et al. |
| 4,772,530 A | 9/1988 | Gottschalk et al. |
| 4,882,245 A | 11/1989 | Gelorme et al. |
| 4,950,581 A | 8/1990 | Koike et al. |
| 4,988,741 A | 1/1991 | Stein |
| 5,013,768 A | 5/1991 | Kiriyama et al. |
| 5,015,554 A | 5/1991 | Ruckert et al. |
| 5,026,624 A | 6/1991 | Day et al. |
| 5,037,721 A | 8/1991 | Doessel |
| 5,225,316 A | 7/1993 | Vogel et al. |
| 5,237,059 A | 8/1993 | Wakamatsu et al. |
| 5,328,940 A | 7/1994 | Zimmer |
| 5,354,643 A | 10/1994 | Cabrera et al. |
| 5,356,752 A | 10/1994 | Cabrera et al. |
| 5,368,976 A | 11/1994 | Tajima et al. |
| 5,372,912 A | 12/1994 | Allen et al. |
| 5,468,589 A | 11/1995 | Urano et al. |
| 5,492,793 A | 2/1996 | Breyta et al. |
| 5,498,506 A | 3/1996 | Wengenroth et al. |
| 5,525,453 A | 6/1996 | Przybilla et al. |
| 5,534,633 A | 7/1996 | Ali |
| 5,554,664 A | 9/1996 | Lamanna et al. |
| 5,556,734 A | 9/1996 | Yamachika et al. |
| 5,558,971 A | 9/1996 | Urano et al. |
| 5,558,976 A | 9/1996 | Urano et al. |

(Continued)

FOREIGN PATENT DOCUMENTS

| DE | 2 027 467 | 12/1971 |
| DE | 225 985 A1 | 8/1985 |

(Continued)

OTHER PUBLICATIONS

International Search Report dated Apr. 11, 2016 in PCT/EP2016/051912 filed Jan. 29, 2016.

*Primary Examiner* — Timothy R Rozof
(74) *Attorney, Agent, or Firm* — Oblon, McClelland, Maier & Neustadt, L.L.P.

(57) ABSTRACT

Compounds of the formula (I) and (IA) wherein X is —O(CO)—; $R_1$ is $C_1$-$C_{12}$haloalkyl or $C_6$-$C_{10}$haloaryl; $R_2$ is located in position 7 of the coumarinyl ring and is $OR_8$; $R_2a$, $R_2b$ and $R_2C$ independently of each other are hydrogen; $R_3$ is $C_1$-$C_8$haloalkyl or $C_1$-$C_8$haloalkyl; $R_4$ is hydrogen; and $R_8$ is $C_1$-$C_6$alkyl; are suitable as photosensitive acid donors in the preparation of photoresist compositions such as used for example in the preparation of spacers, insulating layers, interlayer dielectric films, insulation layers, planarization layers, protecting layers, overcoat layers, banks for electroluminescence displays and liquid crystal displays (LCD).

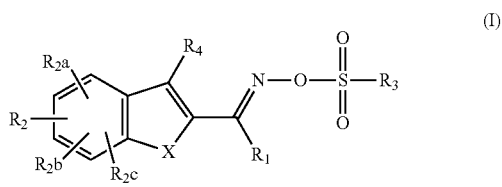

(I)

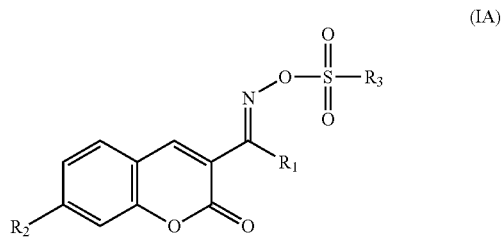

(IA)

20 Claims, No Drawings

(56) References Cited

U.S. PATENT DOCUMENTS

| | | |
|---|---|---|
| 5,595,855 A | 1/1997 | Padmanaban et al. |
| 5,609,989 A | 3/1997 | Bantu et al. |
| 5,625,020 A | 4/1997 | Breyta et al. |
| 5,627,006 A | 5/1997 | Urano et al. |
| 5,663,035 A | 9/1997 | Masuda et al. |
| 5,670,299 A | 9/1997 | Urano et al. |
| 5,679,495 A | 10/1997 | Yamachika et al. |
| 5,719,008 A | 2/1998 | Hozumi et al. |
| 5,731,364 A | 3/1998 | Sinta et al. |
| 5,800,952 A | 9/1998 | Urano et al. |
| 5,800,964 A | 9/1998 | Sato et al. |
| 5,817,444 A | 10/1998 | Sato et al. |
| 5,821,016 A | 10/1998 | Satoh et al. |
| 5,827,634 A | 10/1998 | Thackeray et al. |
| 5,847,015 A | 12/1998 | Tajima et al. |
| 5,863,678 A | 1/1999 | Urano et al. |
| 5,866,298 A | 2/1999 | Iwamoto et al. |
| 5,879,855 A | 3/1999 | Schädeli et al. |
| 5,882,843 A | 3/1999 | Kudo et al. |
| 5,922,473 A | 7/1999 | Muthiah et al. |
| 6,004,724 A | 12/1999 | Yamato et al. |
| 6,017,675 A | 1/2000 | Dietliker et al. |
| 6,048,953 A | 4/2000 | Kawashima et al. |
| 6,261,738 B1 | 7/2001 | Asakura et al. |
| 6,277,538 B1 | 8/2001 | Choi et al. |
| 6,379,861 B1 | 4/2002 | Trefonas, III et al. |
| 6,391,523 B1 | 5/2002 | Hurditch et al. |
| 6,458,506 B2 | 10/2002 | Cameron |
| 6,512,020 B1 | 1/2003 | Asakura et al. |
| 6,576,394 B1 | 6/2003 | Xu et al. |
| 6,599,677 B2 | 7/2003 | Szmanda et al. |
| 6,692,888 B1 | 2/2004 | Barclay et al. |
| 6,777,157 B1 | 8/2004 | Barclay et al. |
| 6,929,896 B2 | 8/2005 | Yamato et al. |
| 2001/0053496 A1 | 12/2001 | Adams |
| 2002/0009663 A1 | 1/2002 | Cameron et al. |
| 2002/0119391 A1 | 8/2002 | Barclay et al. |
| 2002/0172886 A1 | 11/2002 | Momota et al. |
| 2003/0027061 A1 | 2/2003 | Cameron et al. |
| 2003/0064321 A1 | 4/2003 | Malik et al. |
| 2003/0065101 A1 | 4/2003 | Blakeney et al. |
| 2003/0078354 A1 | 4/2003 | Medina et al. |
| 2012/0045616 A1* | 2/2012 | Ishiji ............. C07D 209/20 428/156 |
| 2013/0171415 A1 | 7/2013 | Sakita et al. |
| 2014/0005409 A1 | 1/2014 | Ishiji et al. |

FOREIGN PATENT DOCUMENTS

| | | |
|---|---|---|
| DE | 43 06 069 A1 | 9/1994 |
| DE | 44 08 318 A1 | 9/1994 |
| EP | 0 005 274 B1 | 1/1984 |
| EP | 0 039 025 B1 | 3/1984 |
| EP | 0 022 188 B1 | 10/1984 |
| EP | 0 103 294 B1 | 12/1986 |
| EP | 0 199 672 B1 | 6/1988 |
| EP | 0 119 425 B1 | 1/1990 |
| EP | 0 361 906 A2 | 4/1990 |
| EP | 0 115 870 B1 | 5/1990 |
| EP | 0 245 639 B1 | 6/1991 |
| EP | 0 342 498 B1 | 12/1993 |
| EP | 0 359 431 B1 | 12/1993 |
| EP | 0 320 264 B1 | 4/1994 |
| EP | 0 254 853 B1 | 1/1995 |
| EP | 0 619 520 B1 | 1/1996 |
| EP | 0 727 713 A1 | 8/1996 |
| EP | 0 679 951 B1 | 1/1997 |
| EP | 0 660 187 B1 | 3/1997 |
| EP | 0 831 369 A2 | 3/1998 |
| EP | 0 538 997 B1 | 7/1998 |
| EP | 0 568 993 B1 | 8/1998 |
| EP | 0 710 885 B1 | 12/1998 |
| EP | 0 881 541 A1 | 12/1998 |
| EP | 0 902 327 A2 | 3/1999 |
| EP | 0 654 711 B1 | 6/1999 |
| EP | 0 928 800 A1 | 7/1999 |
| EP | 0 553 737 B1 | 9/1999 |
| EP | 0 592 139 B1 | 10/1999 |
| EP | 0 648 817 B1 | 11/1999 |
| EP | 0 704 762 B1 | 12/1999 |
| EP | 0 762 207 B1 | 4/2000 |
| EP | 0 648 770 B1 | 5/2000 |
| EP | 0 611 998 B1 | 8/2000 |
| EP | 1 091 249 A1 | 4/2001 |
| EP | 0 738 928 B1 | 6/2001 |
| EP | 0 794 457 B1 | 8/2001 |
| EP | 1 128 213 A2 | 8/2001 |
| EP | 0 726 497 B1 | 10/2001 |
| EP | 0 747 771 B1 | 1/2002 |
| EP | 0 762 206 B1 | 1/2002 |
| EP | 0 878 738 B1 | 1/2002 |
| EP | 0 795 786 B1 | 5/2002 |
| EP | 0 775 706 B1 | 6/2002 |
| EP | 0 831 369 B1 | 1/2003 |
| EP | 0 829 766 B1 | 2/2003 |
| EP | 0 780 732 B1 | 7/2003 |
| EP | 1 127 870 B1 | 11/2003 |
| EP | 0 877 293 B1 | 1/2004 |
| EP | 0 742 255 B1 | 4/2004 |
| EP | 0 813 113 B1 | 7/2006 |
| EP | 2 420 890 A1 | 2/2012 |
| GB | 2 304 472 B | 3/1999 |
| GB | 2 307 473 B | 11/1999 |
| GB | 2 307 474 B | 12/1999 |
| JP | 54-5869 A | 1/1979 |
| JP | 57-42009 A | 3/1982 |
| JP | 1-130103 A | 5/1989 |
| JP | 1-134306 A | 5/1989 |
| JP | 1-289946 A | 11/1989 |
| JP | 1-289947 A | 11/1989 |
| JP | 2-2560 A | 1/1990 |
| JP | 2-25850 A | 1/1990 |
| JP | 2-289611 A | 11/1990 |
| JP | 3-128959 A | 5/1991 |
| JP | 3-158855 A | 7/1991 |
| JP | 3-179353 A | 8/1991 |
| JP | 3-191351 A | 8/1991 |
| JP | 3-200251 A | 9/1991 |
| JP | 3-200252 A | 9/1991 |
| JP | 3-200253 A | 9/1991 |
| JP | 3-200254 A | 9/1991 |
| JP | 3-200255 A | 9/1991 |
| JP | 3-223860 A | 10/1991 |
| JP | 3-259149 A | 11/1991 |
| JP | 3-279958 A | 12/1991 |
| JP | 3-279959 A | 12/1991 |
| JP | 4-1650 A | 1/1992 |
| JP | 4-1651 A | 1/1992 |
| JP | 4-11260 A | 1/1992 |
| JP | 4-12356 A | 1/1992 |
| JP | 4-14083 A | 1/1992 |
| JP | 4-123567 A | 4/1992 |
| JP | 4-251259 A | 9/1992 |
| JP | 4-271349 A | 9/1992 |
| JP | 4-294148 A | 10/1992 |
| JP | 4-328552 A | 11/1992 |
| JP | 5-5005 A | 1/1993 |
| JP | 5-27432 A | 2/1993 |
| JP | 5-158233 A | 6/1993 |
| JP | 5-165214 A | 7/1993 |
| JP | 5-173320 A | 7/1993 |
| JP | 5-257275 A | 10/1993 |
| JP | 5-297581 A | 11/1993 |
| JP | 5-297583 A | 11/1993 |
| JP | 5-301910 A | 11/1993 |
| JP | 5-303197 A | 11/1993 |
| JP | 5-303200 A | 11/1993 |
| JP | 5-341510 A | 12/1993 |
| JP | 6-35198 A | 2/1994 |
| JP | 6-43641 A | 2/1994 |
| JP | 6-161109 A | 6/1994 |
| JP | 6-230212 A | 8/1994 |
| JP | 7-36179 A | 2/1995 |

(56) References Cited

FOREIGN PATENT DOCUMENTS

| | | |
|---|---|---|
| JP | 8-272095 A | 10/1996 |
| JP | 8-305019 A | 11/1996 |
| JP | 8-320551 A | 12/1996 |
| JP | 9-127697 A | 5/1997 |
| JP | 9-179299 A | 7/1997 |
| JP | 9-203806 A | 8/1997 |
| JP | 9-269410 A | 10/1997 |
| JP | 9-325209 A | 12/1997 |
| JP | 10-90516 A | 4/1998 |
| JP | 10-171119 A | 6/1998 |
| JP | 10-186664 A | 7/1998 |
| JP | 10-203037 A | 8/1998 |
| JP | 10-221843 A | 8/1998 |
| JP | 10-228110 A | 8/1998 |
| JP | 10-282650 A | 10/1998 |
| JP | 10-307393 A | 11/1998 |
| JP | 10-333334 A | 12/1998 |
| JP | 11-84653 A | 3/1999 |
| JP | 2888454 B2 | 5/1999 |
| JP | 11-153866 A | 6/1999 |
| JP | 11-174459 A | 7/1999 |
| JP | 11-174464 A | 7/1999 |
| JP | 11-194494 A | 7/1999 |
| JP | 11-202489 A | 7/1999 |
| JP | 11-315141 A | 11/1999 |
| JP | 11-338154 A | 12/1999 |
| JP | 2000-26603 A | 1/2000 |
| JP | 2000-34346 A | 2/2000 |
| JP | 2000-34347 A | 2/2000 |
| JP | 2000-34348 A | 2/2000 |
| JP | 2000-81701 A | 3/2000 |
| JP | 2000-221681 A | 8/2000 |
| JP | 2000-241974 A | 9/2000 |
| JP | 2000-292917 A | 10/2000 |
| JP | 2001-5184 A | 1/2001 |
| JP | 2001-33963 A | 2/2001 |
| JP | 2001-56559 A | 2/2001 |
| JP | 2001-66781 A | 3/2001 |
| JP | 2001-83704 A | 3/2001 |
| JP | 2001-125267 A | 5/2001 |
| JP | 2001-147533 A | 5/2001 |
| JP | 2 348 644 B | 6/2001 |
| JP | 2001-166484 A | 6/2001 |
| JP | 2001-214055 A | 8/2001 |
| JP | 2001-214056 A | 8/2001 |
| JP | 2001-228612 A | 8/2001 |
| JP | 2001-235863 A | 8/2001 |
| JP | 2001-242627 A | 9/2001 |
| JP | 2001-255656 A | 9/2001 |
| JP | 2001-255657 A | 9/2001 |
| JP | 2001-264980 A | 9/2001 |
| JP | 2001-264984 A | 9/2001 |
| JP | 2001-272783 A | 10/2001 |
| JP | 2001-281440 A | 10/2001 |
| JP | 2001-290270 A | 10/2001 |
| JP | 2001-290274 A | 10/2001 |
| JP | 2001-296663 A | 10/2001 |
| JP | 2001-305727 A | 11/2001 |
| JP | 2001-318459 A | 11/2001 |
| JP | 2001-318464 A | 11/2001 |
| JP | 2001-330947 A | 11/2001 |
| JP | 2001-330953 A | 11/2001 |
| JP | 2001-330959 A | 11/2001 |
| JP | 2001-337457 A | 12/2001 |
| JP | 2001-343750 A | 12/2001 |
| JP | 2002-3537 A | 1/2002 |
| JP | 2002-6480 A | 1/2002 |
| JP | 2002-6483 A | 1/2002 |
| JP | 2002-6495 A | 1/2002 |
| JP | 2002-6502 A | 1/2002 |
| JP | 2002-23371 A | 1/2002 |
| JP | 2002-23374 A | 1/2002 |
| JP | 2002-30114 A | 1/2002 |
| JP | 2002-30116 A | 1/2002 |
| JP | 2002-30118 A | 1/2002 |
| JP | 2002-37885 A | 2/2002 |
| JP | 2002-40658 A | 2/2002 |
| JP | 2002-72477 A | 3/2002 |
| JP | 2002-72484 A | 3/2002 |
| JP | 2002-82437 A | 3/2002 |
| JP | 2002-90987 A | 3/2002 |
| JP | 2002-91004 A | 3/2002 |
| JP | 2002-99084 A | 4/2002 |
| JP | 2002-116546 A | 4/2002 |
| JP | 2002-122992 A | 4/2002 |
| JP | 2002-122993 A | 4/2002 |
| JP | 2002-128755 A | 5/2002 |
| JP | 2002-131913 A | 5/2002 |
| JP | 2002-131916 A | 5/2002 |
| JP | 2002-139837 A | 5/2002 |
| JP | 2002-145954 A | 5/2002 |
| JP | 2002-145955 A | 5/2002 |
| JP | 2002-156750 A | 5/2002 |
| JP | 2002-161116 A | 6/2002 |
| JP | 2002-162743 A | 6/2002 |
| JP | 2002-162745 A | 6/2002 |
| JP | 2002-169290 A | 6/2002 |
| JP | 2002-169292 A | 6/2002 |
| JP | 2002-179624 A | 6/2002 |
| JP | 2002-182393 A | 6/2002 |
| JP | 2002-202604 A | 7/2002 |
| JP | 2002-206009 A | 7/2002 |
| JP | 2002-214768 A | 7/2002 |
| JP | 2002-226470 A | 8/2002 |
| JP | 2002-229192 A | 8/2002 |
| JP | 2002-234918 A | 8/2002 |
| JP | 2002-241442 A | 8/2002 |
| JP | 2002-251009 A | 9/2002 |
| JP | 2002-251011 A | 9/2002 |
| JP | 2002-265530 A | 9/2002 |
| JP | 2002-268221 A | 9/2002 |
| JP | 2002-268222 A | 9/2002 |
| JP | 2002-275215 A | 9/2002 |
| JP | 2002-278069 A | 9/2002 |
| JP | 2002-278071 A | 9/2002 |
| JP | 2002-278073 A | 9/2002 |
| JP | 2002-284875 A | 10/2002 |
| JP | 2002-287359 A | 10/2002 |
| JP | 2002-287362 A | 10/2002 |
| JP | 2002-296783 A | 10/2002 |
| JP | 2002-301161 A | 10/2002 |
| JP | 2002-303977 A | 10/2002 |
| JP | 2002-303986 A | 10/2002 |
| JP | 2002-308869 A | 10/2002 |
| JP | 2002-308938 A | 10/2002 |
| JP | 2002-311590 A | 10/2002 |
| JP | 2002-328475 A | 11/2002 |
| JP | 2002-338627 A | 11/2002 |
| JP | 2002-341522 A | 11/2002 |
| JP | 2002-348332 A | 12/2002 |
| JP | 2002-351078 A | 12/2002 |
| JP | 2002-356554 A | 12/2002 |
| JP | 2002-356555 A | 12/2002 |
| JP | 2002-357904 A | 12/2002 |
| JP | 2002-357905 A | 12/2002 |
| JP | 2002-363146 A | 12/2002 |
| JP | 2002-363148 A | 12/2002 |
| JP | 2002-363152 A | 12/2002 |
| JP | 2002-371114 A | 12/2002 |
| JP | 2003-5371 A | 1/2003 |
| JP | 2003-5372 A | 1/2003 |
| JP | 2003-26919 A | 1/2003 |
| JP | 2003-35948 A | 2/2003 |
| JP | 2003-43677 A | 2/2003 |
| JP | 2003-43678 A | 2/2003 |
| JP | 2003-43688 A | 2/2003 |
| JP | 2003-43689 A | 2/2003 |
| JP | 2003-57815 A | 2/2003 |
| JP | 2003-57827 A | 2/2003 |
| JP | 2003-66626 A | 3/2003 |
| JP | 2003-98672 A | 4/2003 |
| JP | 2003-114531 A | 4/2003 |
| JP | 2003-122010 A | 4/2003 |
| JP | 2003-122013 A | 4/2003 |

(56) References Cited

FOREIGN PATENT DOCUMENTS

| | | |
|---|---|---|
| JP | 2003-140332 A | 5/2003 |
| JP | 2003-140348 A | 5/2003 |
| JP | 2003-149800 A | 5/2003 |
| JP | 2003-149822 A | 5/2003 |
| JP | 2003-167357 A | 6/2003 |
| JP | 2003-177540 A | 6/2003 |
| JP | 2003-177544 A | 6/2003 |
| JP | 2003-186195 A | 7/2003 |
| JP | 2003-192665 A | 7/2003 |
| JP | 2003-195504 A | 7/2003 |
| JP | 2003-207896 A | 7/2003 |
| JP | 2003-233185 A | 8/2003 |
| JP | 2003-241385 A | 8/2003 |
| JP | 2003-280200 A | 10/2003 |
| JP | 2003-280207 A | 10/2003 |
| JP | 2004-264623 A | 9/2004 |
| JP | 2008-40183 A | 2/2008 |
| JP | 4168443 B2 | 10/2008 |
| JP | 4207604 B2 | 1/2009 |
| JP | 2009-98616 A | 5/2009 |
| JP | 2011-181391 A | 9/2011 |
| JP | 2011-241055 A | 12/2011 |
| JP | 2013-231868 A | 11/2013 |
| JP | 2013-242511 A | 12/2013 |
| JP | 2013-242537 A | 12/2013 |
| JP | 2014-10200 A | 1/2014 |
| JP | 2014-10382 A | 1/2014 |
| WO | WO 90/01512 A1 | 2/1990 |
| WO | WO 93/15440 A1 | 8/1993 |
| WO | WO 96/41237 A1 | 12/1996 |
| WO | WO98/31765 A1 | 7/1998 |
| WO | WO 99/63017 A1 | 12/1999 |
| WO | WO 99/66506 A1 | 12/1999 |
| WO | WO 01/86353 A1 | 11/2001 |
| WO | WO 02/06901 A2 | 1/2002 |
| WO | WO 03/021358 A1 | 3/2003 |
| WO | WO 2007/118794 A1 | 10/2007 |
| WO | WO 2010/057922 A1 | 5/2010 |
| WO | WO 2012/101245 A1 | 8/2012 |
| WO | WO 2012/113829 A1 | 8/2012 |
| WO | WO 2013/156509 A2 | 10/2013 |
| WO | WO 2014/064064 A1 | 5/2014 |

\* cited by examiner

LATENT ACIDS AND THEIR USE

The present invention relates to novel oxime derivatives with specific heteroaryl chromophore, chemically amplified photoresist compositions comprising said compounds and to the use of the compounds as latent acids in alkaline soluble resin composition, in particular in photo resist formulations for display application, e.g. insulation layer, liquid crystal displays (LCD), organic light emitting diode (OLED).

LCD device, OLED device, etc. are equipped with a patterned interlayer insulating film. In forming this interlayer insulating film a photosensitive resin composition is widely employed since the number of steps required for obtaining a pattern shapes is small, and moreover, it gives sufficient flatness. There is a desire for the interlayer insulating film in the display device to have high transparency in addition to cured film physical properties such as excellent insulation, solvent resistance, heat resistance, hardness and indium tin oxide (ITO) sputtering suitability.

The insulation layer in backplane for LCD and OLED which is used to keep interlayer insulation characteristics is manufactured by photolithography by using positive or negative type photo resists comprising alkaline soluble photoresists, chemically amplified catalysts generating latent acid and solvent. Contact hall in the passivation layer is patterned by photo exposure through the patterned mask and baked, for example, at about 230° C. Transparency, thermal stability, adhesion, residual film rate and storage stability are required for the insulation layer.

The planarization layer for LCD and OLED is used to form a flat surface on the color filter (CF) or the electrode. As a base material for a planarization layer, acrylic and/or epoxy resins, are usually employed. A planarization layer is usually manufactured by heating for example, at about 230° C. or in combination with photolithography prior to the post-baking process. Transparency and specific insulation characteristic are required for the planarization layer.

The protecting layer for LCD and OLED is used to protect a colored layer, and to form a flat surface of the step of coloration layer. As a base material for a protecting layer, acrylic resin, melamine resin, and polyimide resin are usually employed. The protecting layer is usually manufactured by heating for example, at about 200° C. for 1 h. Transparency, surface flatness, adhesion and thermal resistance are required for the protecting layer.

The overcoat layer for LCD is used to planarize the surface of the color filters and enhance the orientation of liquid crystal and to prevent ion elution from CF to the liquid crystal. The overcoat is manufactured using a thermosetting resin based on acrylate resin and/or epoxy resin on the color filter by heating, for example, at 220° C. for 30 min. or in combination with photolithography prior to the post-baking process. Thermal stability, light resistance, adhesiveness, hardness and transparency are required for the overcoat layer.

A large number of organic substances belonging to the classes of onium salts or oxime sulfonates which generate latent acid by photo exposure to the photoresist are known for the application as photo acid generator. However, compositions comprising them often present difficulties concerning the photo sensitivity.

For example U.S. Pat. No. 6,017,675 discloses a broad scope of oxime sulfonated compounds, inter alia an arylsulfonyloxime ester compound with a coumarinyl chromophore.

In U.S. Pat. No. 6,512,020 and U.S. Pat. No. 6,261,738 monomeric and dimeric oxime derivatives are described as latent acid donors in positive and negative photoresists particular suitable for applications in the Deep UV range.

In US20120045616A as acid generating compound in a photosensitive resin composition a sulfonyl oxime ester compound with a nitrogen-comprising heterocyclic chromophore part is disclosed.

According to US20130171415A a photosensitive compound, having an oxime group bound directly to the C-atom of a ring, is used as acid-generating component in a photosensitive composition.

In forming electronic display devices, in particular in forming insulation layers, color filters and microlenses, it is necessary that the radiation-sensitive resin composition used to form the insulation layers etc. have a high sensitivity and high transmittance properties. In this context the challenge for the corresponding acid-generating compounds, being part of said radiation-sensitive resin composition also is to provide corresponding properties, namely with respect to photosensitivity and in particular transmittance.

It has been found, surprisingly, that photo sensitivity and transparency significantly increased by introducing a coumarinyl chromophore with a strong electron withdrawing group such as a perfluoroalkyl or perfluoroaryl group attached to the oxime part.

Accordingly, subject of the invention is a compound of the formula (I)

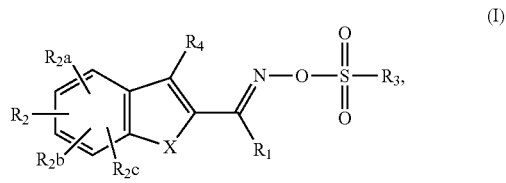

X is —O(CO)—;
$R_1$ is $C_1$-$C_{12}$haloalkyl or $C_6$-$C_{10}$haloaryl;
$R_2$ is located in position 7 of the coumarinyl ring and is $OR_8$;
$R_2a$, $R_2b$ and $R_2c$ independently of each other are hydrogen;
$R_3$ is $C_1$-$C_8$haloalkyl or $C_1$-$C_8$alkyl;
$R_4$ is hydrogen; and
$R_8$ is $C_1$-$C_6$alkyl.

$C_1$-$C_6$alkyl is linear or branched and is, for example $C_1$-$C_4$alkyl. Examples are methyl, ethyl, propyl, isopropyl, n-butyl, sec-butyl, isobutyl, tert-butyl, Pentyl or hexyl.

$C_1$-$C_{12}$haloalkyl is for example $C_1$-$C_8$-, $C_1$-$C_6$- or $C_1$-$C_4$-alkyl mono- or poly-substituted by halogen, $C_1$-$C_8$-, $C_1$-$C_6$- or $C_1$-$C_4$-alkyl being, for example, as defined above. The alkyl radical is for example mono- or poly-halogenated, up to the exchange of all H-atoms by halogen. Examples are fluoromethyl, trifluoromethyl, trichloromethyl or 2-fluoropropyl, especially trifluoromethyl or trichloromethyl.

$C_1$-$C_{12}$haloalkyl is for example $CF_3$, $C_mHF_{2m}$, $C_nF_{2n+1}$; wherein n is an integer 2 to 8, for example 2 to 6, 2 to 4, 2 or 3, and m is an integer 1 to 8, for example 1 to 6, 1 to 4, 1 to 3, 1 or 2.

$C_6$-$C_{10}$haloaryl is for example an aromatic group substituted by one or more halogen atoms. Examples are phenyl or naphthyl substituted by one or more halogen. Phenyl is for example substituted 1 to five times, e.g. once, twice or three times, in particular once or twice by halogen. Naphthyl is for example substituted 1 to seven times, e.g. once, twice or three times, in particular once or twice by halogen.

Halogen is fluorine, chlorine, bromine and iodine, especially fluorine, chlorine and bromine, preferably fluorine and chlorine. In particular fluorine Position 7 of the coumarinyl ring is indicated in the formula:

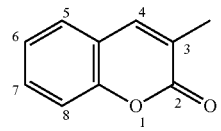

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

The term "optionally interrupted" means uninterrupted or interrupted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated above for the compounds according to the present invention in the context of this invention are intended to refer to all categories of the claims, that is to the compounds, compositions, use, process claims as well.

It is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is +/−10%.

Description of compounds of the formula formula (I), (IIa) or (IIb)

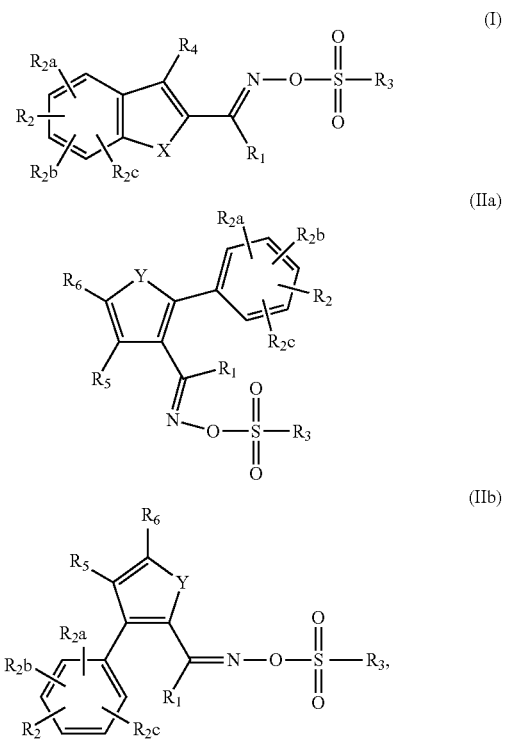

wherein

X is —O(CO)—, —NR$_7$(CO)—, NR$_7$, O or S; Y is NR$_7$, O or S; R$_1$ is C$_1$-C$_{12}$haloalkyl or C$_6$-C$_{10}$haloaryl; R$_2$, R$_{2a}$, R$_2$b and R$_2$c independently of each other are hydrogen, C$_1$-C$_{12}$alkyl, OR$_8$, SR$_9$, NR$_{10}$R$_{11}$, O(CO)R$_8$, or R$_2$, R$_{2a}$, R$_2$b and R$_2$c independently of each other are phenyl, phenyl which is substituted one or more C$_1$-C$_8$alkyl, C$_1$-C$_8$haloalkyl, C$_2$-C$_8$alkenyl, halogen, OR$_8$, SR$_9$, NR$_{10}$R$_{11}$ or by C$_2$-C$_8$alkyl which is interrupted by one or more non-consecutive O, S, (CO)O or O(CO); or R$_2$ denotes a group —CR$_{12}$═CR$_{13}$—CR$_{14}$═CR$_{15}$— which is attached to a C-atom of the phenyl ring to which R$_2$ is bound; R$_3$ is C$_1$-C$_8$alkyl, C$_1$-C$_8$haloalkyl, C$_2$-C$_8$alkenyl or C$_2$-C$_8$alkyl which is interrupted by one or more non-consecutive O, S, (CO)O or O(CO); R$_4$, R$_5$ and R$_6$ independently of each other are hydrogen, C$_1$-C$_{20}$alkyl, C$_1$-C$_8$haloalkyl, phenyl-C$_1$-C$_4$alkyl, unsubstituted phenyl or phenyl which is substituted by one or more C$_1$-C$_8$alkyl, C$_1$-C$_8$haloalkyl, C$_2$-C$_8$alkenyl, halogen, OR$_8$, SR$_9$, NR$_{10}$R$_{11}$ or by C$_2$-C$_8$alkyl which is interrupted by one or more non-consecutive O, S, (CO)O or O(CO); R$_7$ is C$_1$-C$_{12}$alklyl, phenyl-C$_1$-C$_4$alkyl, phenyl, phenyl which is substituted by one or more C$_1$-C$_8$alkyl, C$_1$-C$_8$haloalkyl, halogen, C$_2$-C$_8$alkenyl, OR$_8$, SR$_9$, NR$_{10}$R$_{11}$ or by C$_2$-C$_8$alkyl which is interrupted by one or more non-consecutive O, S, (CO)O or O(CO); R$_8$ is C$_1$-C$_{12}$alkyl or C$_2$-C$_{12}$alkyl which is interrupted by one or more non-consecutive O, S, (CO)O, O(CO), or R$_8$ is C$_3$-C$_{12}$cycloalkyl, C$_3$-C$_{12}$cycloalkyl which is interrupted by one or more O, C$_3$-C$_{12}$cycloalkyl-C$_1$-C$_{12}$alkyl, C$_3$-C$_{12}$cycloalkyl-C$_1$-C$_{12}$alkyl which is interrupted by one or more O, wherein the interrupting O-atoms may be interrupting both, the cycloalkyl as well as the alkyl part of the radical, or R$_8$ is phenyl, phenyl which is substituted one or more C$_1$-C$_8$alkyl, C$_1$-C$_8$haloalkyl, C$_2$-C$_8$alkenyl, halogen, SR$_9$, NR$_{10}$R$_{11}$, C$_1$-C$_{12}$alkoxy, phenoxy or by C$_2$-C$_8$alkyl which is interrupted by one or more non-consecutive O, S, (CO)O or O(CO); $R_9$ is $C_1$-$C_{12}$alkyl or $C_2$-$C_{12}$alkyl which is interrupted by one or more non-consecutive O, S, COO, OCO, or $R_9$ is $C_3$-$C_{12}$cycloalkyl, $C_3$-$C_{12}$cycloalkyl which is interrupted by one or more O, $C_3$-$C_{12}$cycloalkyl-$C_1$-$C_{12}$alkyl, $C_3$-$C_{12}$cycloalkyl-$C_1$-$C_{12}$alkyl which is interrupted by one or more O, wherein the interrupting O-atoms may be interrupting both, the cycloalkyl as well as the alkyl part of the radical, or $R_9$ is phenyl, phenyl which is substituted one or more $C_1$-$C_8$alkyl, $C_1$-$C_8$haloalkyl, $C_2$-$C_8$alkenyl, halogen, $OR_8$, $C_1$-$C_{12}$alkylthio, phenylthio, $NR_{10}R_{11}$, or by $C_2$-$C_8$alkyl which is interrupted by one or more non-consecutive O, S, (CO)O or O(CO); $R_{10}$ and $R_{11}$ independently of one another are hydrogen, phenyl-$C_1$-$C_4$alkyl, $C_1$-$C_{12}$alkyl, $C_2$-$C_{12}$alkyl which is interrupted by one or more non-consecutive O, S, (CO)O or O(CO); $R_{12}$, $R_{13}$, $R_{14}$ and $R_{15}$ independently of each other are hydrogen, $C_1$-$C_8$alkyl, halogen, $OR_8$, $SR_9$ or $NR_{10}R_{11}$ could be suitable.

Oxime sulfonates of the formula I [and of the fomual (IA) as shown below] are prepared by methods described in the literature, for example by reaction of the corresponding oximes with a sulfonyl halide, in particular a chloride, or an anhydride in an inert solvent such as for example t-butyl methyl ether, tetra-hydrofurane (THF), dimethoxyethane, dimethylacetamide (DMA) or dimethylformamide in the presence of a base or a mixture of bases, for example trimethylamine, pyridine or 2,6-lutidine, or in a basic solvent such as pyridine. As example in the following the preparation of compounds of the formula (I) is described:

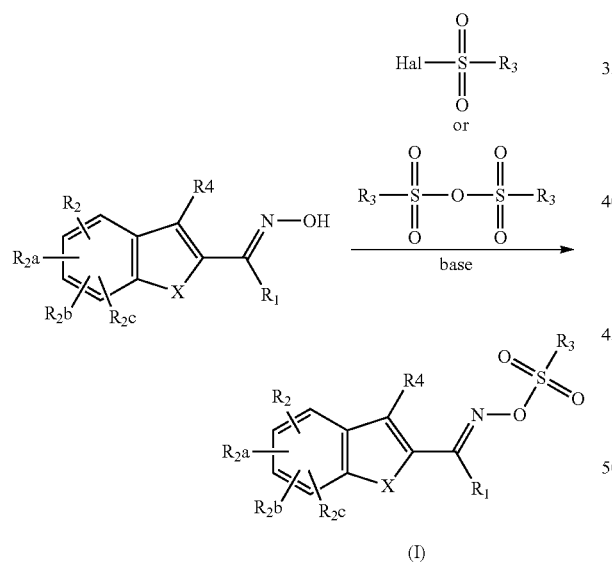

$R_1$, $R_2$, $R_{2a}$, $R_{2b}$, $R_3$, $R_4$ and X have the meanings as given above. Hal means a halogen atom, in particular Cl.

$R_3$ preferably is n-propyl or trifluoromethyl.

Such reactions are well known to those skilled in the art, and are generally carried out at temperatures of −15 to +50° C., preferably 0 to 25° C.

Every oxime sulfonate group can exist in two configurations, (Z) or (E). It is possible to separate the isomers by conventional methods, but it is also possible to use the isomeric mixture as such photoacid generating species. Therefore, the invention also relates to mixtures of configurational isomers of compounds of the formula (I) or mixtures of configurational isomers of compounds of the formulae (IIa) or mixtures of configurational isomers of compounds of the formula (IIb).

The oximes required as starting materials can be obtained by a variety of methods described in standard chemistry textbooks (for instance in J. March, Advanced Organic Chemistry, 4th Edition, Wiley Interscience, 1992), or in specialized monographs, for example, S. R. Sandler & W. Karo, Organic functional group preparations, Vol. 3, Academic Press.

One of the most convenient methods is, for example, the reaction of aldehydes or ketones with hydroxylamine or its salt in polar solvents like DMA, aqueous DMA, ethanol or aqueous ethanol. In that case, a base such as sodium acetate or pyridine can be added to control the pH of the reaction mixture. It is well known that the rate of the reaction is pH-dependent, and the base can be added at the beginning or continuously during the reaction. Basic solvents such as pyridine can also be used as base and/or solvent or co-solvent. The reaction temperature is generally from room temperature to the refluxing temperature of the mixture, usually about 20-120° C.

The corresponding ketone intermediates bearing a coumarin group are for example prepared by the methods described in Dyes and Pigments 91 (2011) 309-316. Such reactions are well known to those skilled in the art.

The coumarinyl body of the compounds of the present invention is for example prepared by reaction of a phenolic aldehyde and a corresponding diketone

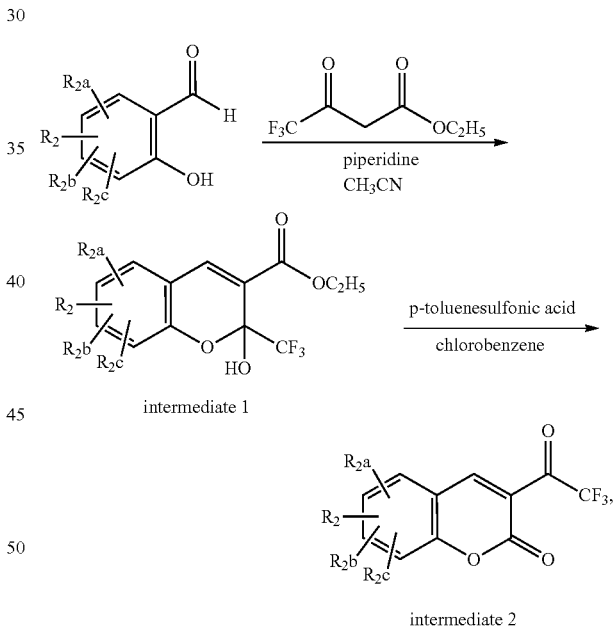

followed by formation of the oxime and esterification of said oxime

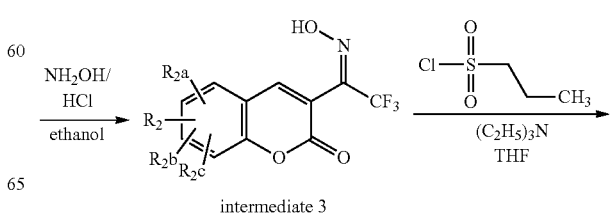

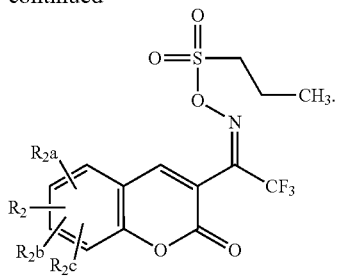

X is —O(CO)— and $R_2$ is located in the para-position to the oxime group. Accordingly the compound of the formula (I) has the following structure (IA)

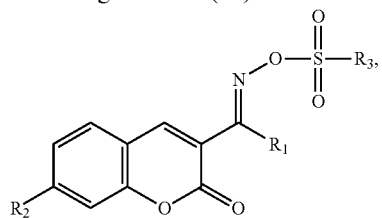

$R_1$, $R_2$, and $R_3$ have the definitions as listed above.

Subject of the invention therefore also is a compound of the formula (I), which is of the formula (IA)

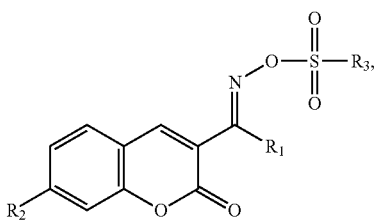

(IA)

wherein $R_1$, $R_2$ and $R_3$ have the definitions as listed above.

$R_1$ is $C_1$-$C_{12}$haloalkyl or $C_6$-$C_{10}$haloaryl; in particular $C_1$-$C_{12}$haloalkyl as defined above.

$R_2$ is $OR_8$, especially $OC_1$-$C_4$alkyl, preferably methoxy.

$R_8$ for example is $C_1$-$C_4$alkyl, in particular methyl.

Preferred is a compound of the formula (IA) as defined above, wherein $R_1$ is $C_1$-$C_4$haloalkyl, in particular $CF_3$;

$R_2$ is is $OR_8$;

$R_3$ is $C_1$-$C_4$haloalkyl or $C_1$-$C_4$alkyl, in particular $CH_3$ or $CF_3$; and $R_8$ is $C_1$-$C_4$alkyl, in particular methyl.

In particular interesting are compounds of the formula (IA).

Preferred is a compound of the formula (IA) which is (OS17)

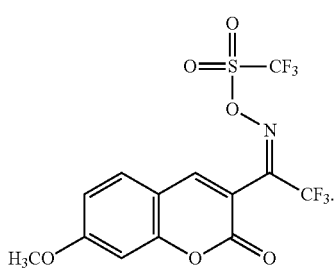

The compounds of the formula (I) and (IA), can be used as photosensitive acid donors.

Interesting therefore is a composition comprising (a) a compound which cures upon the action of an acid or a compound whose solubility is increased upon the action of an acid; and (b) at least one compound of the formula (I) and (IA) as described above.

The compounds of the formula (I) and (IA) can be used as photosensitive acid donors in a photosensitive resin composition. They optionally also function as a compound whose solubility is increased upon the action of an acid, that is as part of component (a) as defined above. Photosensitive resin composition systems can be prepared by image-wise irradiation of systems comprising compounds of formula (I) or (IA) followed by a developing step.

The invention accordingly relates to a chemically amplified photosensitive resin composition comprising (a) a compound which cures upon the action of an acid; or
    a compound whose solubility is increased upon the action of an acid; and (b) as photosensitive acid donor, at least one compound of the formula (I) or (IA) as defined above.

A chemically amplified photosensitive resin composition is understood to be a photosensitive resin composition wherein the radiation sensitive component provides a catalytic amount of acid which subsequently catalyses a chemical reaction of at least one acid-sensitive component of the photosensitive resin composition. Resulting is the induction of a solubility difference between the irradiated and non-irradiated areas of the photosensitive resin composition. Because of the catalytic nature of this process one acid molecule can trigger reactions at multiple sites as it diffuses through the reactive polymer matrix, from one reaction site to the next, as long as it is not trapped or destroyed by any secondary reaction. Therefore, a small acid concentration is sufficient to induce a high difference in the solubility between exposed and unexposed areas. Thus, only a small concentration of the latent acid compound is necessary. As a result, photosensitive resin compositions with high contrast and high transparency at the exposure wavelength in optical imaging can be formulated, which in turn produce steep, vertical image profiles at high photosensitivity. However, as a result of this catalytic process, it is required that the latent acid catalysts are chemically and thermally very stable (as long as not irradiated) in order not to generate acid during storage or during processing, which—in most cases—requires a post exposure bake step to start or to complete the catalytic reaction which leads to the solubility differential. It is also required to have good solubility of the latent catalysts in the liquid formulation and the solid film to avoid any particle generation which would interfere with the application of these photosensitive resin compositions in microelectronic manufacturing processes.

In contrast, positive photosensitive resin composition, i.e. photoresist, materials which are not based on the chemical amplification mechanism must contain a high concentration of the latent acid, because it is only the acid concentration which is generated from the latent acid under exposure which contributes to the increased solubility of the exposed areas in alkaline developer. Because small acid concentration has only a little effect on the change of the dissolution rate of such photoresist and the reaction proceeds typically without a post exposure bake here, the requirements regarding chemical and thermal stability of the latent acid are less demanding than for chemically amplified positive photosensitive resin compositions. These photoresists require also a much higher exposure dose to generate enough acid for achieving sufficient solubility in the alkaline developer in the exposed areas and also suffer from the relatively low optical transparency (due to the high concentration of latent acid necessary) and thus also lower resolution and sloped images. Resist compositions based on non-chemically amplified technology are therefore inferior in photosensitivity, resolution and image quality compared to chemically amplified photosensitive resin compositions.

From the above it becomes clear that chemical and thermal stability of a latent catalyst is vital for a chemically amplified photosensitive resin composition and that latent acids which can work in a non-chemically amplified photosensitive resin composition are not necessarily applicable to chemically amplified photosensitive resin compositions because of the different acid diffusion requirements, acid strength requirements and thermal and chemical stability requirements.

The difference in photosensitive resin composition solubility between irradiated and non-irradiated sections that occurs as a result of the acid-catalysed reaction of the photosensitive resin composition material during or after irradiation may be of two types depending upon which further constituents are present in the photosensitive resin composition. If the compositions according to the invention comprise components that increase the solubility of the composition in the developer after irradiation, the photosensitive resin composition is positive.

The invention accordingly relates to a chemically amplified photosensitive resin composition, which is positive tone.

If, on the other hand, the components of the formulation reduce the solubility of the composition after irradiation, the photosensitive resin composition is negative.

The invention accordingly relates also to a chemically amplified photosensitive resin composition, which is negative tone.

A monomeric or polymeric compound which—in the unexposed areas—reduces the dissolution rate of an additionally present alkaline soluble binder resin in the formulation and which is essentially alkali-insoluble in the unexposed areas so that the coated film remains in the unexposed area after development in alkaline solution, but which is cleaved in the presence of acid, or is capable of being rearranged, in such a manner that its reaction product becomes soluble in the alkaline developer is referred to hereinafter as dissolution inhibitor.

The invention includes, as a special embodiment a chemically amplified positive alkaline-developable photosensitive resin composition, comprising (a1) at least one polymer having acid-labile groups which decompose in the presence of an acid and increase the solubility of the coated film in an aqueous alkaline developer solution in the exposed area and (b) at least one compound of formula (I) or (IA).

A further embodiment of the invention is a chemically amplified positive alkaline-developable photosensitive resin composition, comprising (a2) at least one monomeric or oligomeric dissolution inhibitor having at least one acid-labile group which decomposes in the presence of acid and increases the solubility in an aqueous alkaline developer solution and at least one alkali-soluble polymer and, (b) at least one compound of formula (I) or (IA).

Another specific embodiment of the invention resides in a chemically amplified positive alkaline-developable photosensitive resin composition, comprising (a1) at least one polymer having acid labile groups which decompose in the presence of an acid and increase the solubility in an alkaline developer in the exposed area;

(a2) a monomeric or oligomeric dissolution inhibitor, having at least one acid labile group, which decomposes in the presence of an acid and increase the alkaline solubility in the exposed area;

(a3) an alkali-soluble monomeric, oligomeric or polymeric compound at a concentration which still keeps the colated film in the unexposed area essentially insoluble in the alkaline developer, and (b) at least one compound of formula (I) or (IA).

The invention therefore pertains to a chemically amplified photosensitive resin composition, comprising (a1) at least one polymer having an acid-labile group which decomposes in the presence of an acid to increase the solubility in aqueous alkaline developer solution and/or (a2) at least one monomeric or oligomeric dissolution inhibtor having an acid-labile group which decomposes in the presence of an acid to increase the solubility in aqueous alkaline developer solution and/or (a3) at least one alkali-soluble monomeric, oligomeric or polymeric compound; and (b) as photosensitive acid donor, at least one compound of formula (I) or (IA).

The compositions may comprise additionally to the component (b) other photosensitive acid donors and/or (c) other additives.

Such chemically amplified positive photosensitive resin composition, i.e. photoresist, systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

Suitable examples of acid-labile groups which decompose in the presence of an acid to produce aromatic hydroxy groups, carboxylic groups, keto groups and aldehyde groups and increase the solubility in aqueous alkaline developer solution are, for example, alkoxyalkyl ether groups, tetrahydrofuranyl ether groups, tetrahydropyranyl ether groups, tert.-alkyl ester groups, trityl ether groups, silyl ether groups, alkyl carbonate groups as for example tert.-butyloxycarbonyloxy-, trityl ester groups, silyl ester groups, alkoxymethyl ester groups, cumyl ester groups, acetal groups, ketal groups, tetrahydropyranyl ester groups, tetrafuranyl ester groups, tertiary alkyl ether groups, tertiary alkyl ester groups, and the like. Examples of such group include alkyl esters such as methyl ester and tert-butyl ester, acetal type esters such as methoxymethyl ester, ethoxymethyl enter, 1-ethoxyethyl ester, 1-isobutoxyethyl ester, 1-isopropoxyethyl ester, 1-ethoxypropyl ester, 1-(2-methoxyethoxy) ethyl ester, 1-(2-acetoxyethoxy)ethyl ester, 1-[2-(1-adamantyloxy) ethoxy]ethyl ester, 1-[2-(1-adamantylcarbonyloxy) ethoxy]ethyl ester, tetrahydro-2-furyl ester and tetrahydro-2-pyranyl ester, and alicyclic ester such as isobornyl ester.

The polymer having functional groups capable of decomposing by the action of an acid to enhance solubility of the coated film comprising this polymer in an alkaline developing solution, which can be incorporated in the positive photosensitive resin composition according to the present invention, may have the acid-labile groups in the backbone and/or side chains thereof, preferably in side chains thereof.

The polymer having acid-labile groups suitable for the use in the present invention can be obtained with a polymer analogous reaction where the alkaline soluble groups are partially or completely converted into the respective acid labile groups or directly by (co)-polymerization of monomers which have the acid labile groups already attached, as is for instance disclosed in EP254853, EP878738, EP877293, JP02-025850A, JP03-223860A, and JP04251259A.

The polymers which have acid labile groups pendant to the polymer backbone, in the present invention preferably are polymers which have, for example silylether, acetal, ketal and alkoxyalkylester groups (called "low-activation energy blocking groups") which cleave completely at relatively low post exposure bake temperatures (typically between room temperature and 110° C.) and polymers which have, for example, tert-butylester groups or tert.-butyloxycarbonyl (TBOC) groups or other ester groups which contain a secondary or tertiary carbon atom next to the oxygen atom of the ester bond (called "high-activation energy blocking groups") which need higher bake temperatures (typically >110° C.) or without any post exposure process, especially in the cases for the applications on insulating layers, interlayer dielectric films, passivation layers, planarization layers, protecting layers, overcoat layers, banks for display devices such as electroluminescence displays and liquid crystal displays (LCD), in order to complete the deblocking reaction in the presence of acid. Hybrid systems can also be applied, wherein, both, high activation energy blocking groups as well as low activation energy blocking groups are present within one polymer. Alternatively, polymer blends of polymers, each utilizing a different blocking group chemistry, can be used in the photosensitive positive compositions according to the invention.

Preferred polymers which have acid labile groups are polymers and co-polymers comprising the following distinct monomer types:

1) monomers that contain acid-labile groups which decompose in the presence of an acid to increase the solubility in aqueous alkaline developer solution and 2) monomers that are free of acid labile groups and free of groups that contribute to the alkaline solubility and/or 3) monomers that contribute to aqueous alkaline solubility of the polymer.

Please note monomers hereinafter mean repeating constituent units in case of polymers obtained with a polymer analogous reaction where the alkaline soluble groups are partially or completely converted into the respective acid labile groups.

Examples of monomers of type 1) are:

non-cyclic or cyclic secondary and tertiary-alkyl (meth)acrylates such as butyl acrylate, including t-butyl acrylate, butyl methacrylate, including t-butyl methacrylate, 3-oxocyclohexyl (meth)acrylate, tetrahydropyranyl (meth)acrylate, 2-methyl-adamantyl (meth)acrylate, cyclohexyl (meth)acrylate, norbornyl (meth)acrylate, (2-tetrahydropyranyl) oxynorbonylalcohol acrylates, (2-tetrahydropyranyl) oxymethyltricyclododecanemethanol methacrylates, trimethylsilylmethyl (meth)acrylate, (2-tetrahydropyranyl) oxynorbonylalcohol acrylates, (2-tetrahydropyranyl)oxymethyltricyclododecanemethanol methacrylates, trimethylsilylmethyl (meth)acrylate o-/m-/p-(3-oxocyclohexyloxy)-styrene, o-/m-/p-(1-methyl-1-phenylethoxy)styrene, o-/m-/p-tetrahydropyranyloxy-styrene, o-/m-/p-adamantyloxystyrene, o-/m-/p-cyclohexyloxystyrene, o-/m-/p-norbornyloxystyrene, non-cyclic or cyclic alkoxycarbonylstyrenes such as o-/m-/p-butoxycarbonylstyrene, including p-t-butoxycarbonylstyrene, o-/m-/p-(3-oxocyclohexyloxy-carbonyl)styrene, o-/m-/p-(1-methyl-1-phenylethoxycarbonyl)styrene, o-/m-/p-tetrahydropyranyloxycarbonylstyrene, o-/m-/p-adamantyloxycarbonylstyrene, o-/m-/p-cyclohexyloxycarbonylstyrene, o-/m-/p-norbornyloxycarbonylstyrene, non-cyclic or cyclic alkoxycarbonyloxystyrenes such as o-/m-/p-butoxycarbonyloxystyrene, including p-t-butoxycarbonyloxystyrene, o-/m-/p-(3-oxocyclohexyloxycarbonyloxy)styrene, o-/m-/p-(1-methyl-1-phenylethoxycarbonyloxy)styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxystyrene, non-cyclic or cyclic alkoxycarbonylalkoxystyrenes such as o/m/p-butoxycarbonylmethoxystyrene, p-t-butoxycarbonylmethoxystyrene, o-/m-/p-(3-oxocyclohexyloxycarbonylmethoxy)styrene, o-/m-/p-(1-methyl-1-phenylethoxycarbonylmethoxy)styrene, o-/m-/p-tetrahydropyranyloxy-carbonylmethoxystyrene, o-/m-/p-adamantyloxycarbonylmethoxystyrene, o-/m-/p-cyclohexyloxycarbonylmethoxystyrene, o-/m-/p-norbornyloxycarbonylmethoxystyrene, trimethylsiloxystyrene, dimethyl(butyl)siloxystyrene, unsaturated alkyl acetates such as isopropenyl acetate and the derivatives of thereof.

Monomers of type 1) bearing low activation energy acid labile groups include, for example, p- or m-(1-methoxy-1-methylethoxy)-styrene, p- or m-(1-methoxy-1-methylethoxy)-methylstyrene, p- or m-(1-methoxy-1-methylpropoxy)styrene, p- or m-(1-methoxy-1-methylpropoxy)-methylstyrene, p- or m-(1-methoxyethoxy)-styrene, p- or m-(1-methoxyethoxy)-methylstyrene, p- or m-(1-ethoxy-1-methylethoxy)styrene, p- or m-(1-ethoxy-1-methylethoxy)-methylstyrene, p- or m-(1-ethoxy-1-methylpropoxy)styrene, p- or m-(1-ethoxy-1-methylpropoxy)-methylstyrene, p- or m-(1-ethoxyethoxy)styrene, p- or m-(1-ethoxyethoxy)-methylstyrene, p-(1-ethoxyphenyl-ethoxy)styrene, p- or m-(1-n-propoxy-1-metylethoxy)styrene, p- or m-(1-n-propoxy-1-metylethoxy)-methylstyrene, p- or m-(1-n-propoxyethoxy)styrene, p- or m-(1-n-propoxyethoxy)-methylstyrene, p- or m-(1-isopropoxy-1-methylethoxy)styrene, p- or m-(1-isopropoxy-1-methylethoxy)-methylstyrene, p- or m-(1-isopropoxyethoxy)styrene, p- or m-(1-isopropoxyethoxy)-methylstyrene, p- or m-(1-isopropoxy-1-methylpropoxy)styrene, p- or m-(1-isopropoxy-1-methylpropoxy)-methylstyrene, p- or m-(1-isopropoxypropoxy)styrene, p- or m-(1-iso-propoxyporpoxy)-methylstyrene, p- or m-(1-n-butoxy-1-methylethoxy)styrene, p- or m-(1-n-butoxyethoxy) styrene, p- or m-(1-isobutoxy-1-methylethoxy)styrene, p- or m-(1-tertbutoxy-1-methylethoxy)styrene, p- or m-(1-n-pentoxy-1-methylethoxy)styrene, p- or m-(1-isoamyloxy-1-methylethoxy)styrene, p- or m-(1-n-hexyloxy-1-methylethoxy)styrene, p- or m-(1-cyclohexyloxy-1-methylethoxy) styrene, p- or m-(1-trimethylsilyloxy-1-methylethoxy) styrene, p- or m-(1-trimethylsilyloxy-1-methylethoxy)-methylstyrene, p- or m-(1-benzyloxy-1-methylethoxy) styrene, p- or m-(1-benzyloxy-1-methylethoxy)-methylstyrene, p- or m-(1-methoxy-1-methylethoxy) styrene, p- or m-(1-methoxy-1-methyl-ethoxy)-methylstyrene, p- or m-(1-trimethylsilyloxy-1-methylethoxy)styrene, p- or m-(1-trimethylsilyloxy-1-methylethoxy)-methylstyrene and (meth)acrylates, for example, 1-ethoxyethyl methacrylate, 1-ethoxyethyl acrylate, 1-methoxyethyl methacrylate, 1-methoxyethyl acrylate, 1-n-butoxyethyl methacrylate, 1-n-butoxyethyl acrylate, 1-isobutoxyethyl methacrylate, 1-isobutoxyethyl acrylate, 1-(2-chlorohexylethoxy)ethyl methacrylate, 1-(2-chlorohexylethoxy)ethyl acrylate, 1-(2-ethylhexyloxy)ethyl methacrylate, 1-(2-ethylhexyloxy)ethyl acrylate, 1-n-propoxyethyl methacrylate, 1-n-propoxyethyl acrylate, 1-cyclohexyloxyethyl methacrylate, 1-cyclohexyloxyethyl acrylate, 1-(2-cyclohexylethoxy)ethyl methacrylate, 1-(2- cyclohexylethoxy)ethyl acrylate, 1-benzyloxyethyl methacrylate and 1-benzyloxyethyl acrylate, tetrahydro-2H-pyran-2-yl methacrylate, tetrahydro-2H-pyran-2-yl acrylate, tetrahydrofuran-2-yl methacrylate, and tetrahydrofuran-2-yl acrylate.

Other examples of polymers having alkoxyalkylester acid labile groups are given in U.S. Pat. No. 5,225,316 and EP829766. Examples of polymers with acetal blocking groups are given in U.S. Pat. No. 5,670,299, EP780732, U.S. Pat. No. 5,627,006, U.S. Pat. No. 5,558,976, U.S. Pat. No. 5,558,971, U.S. Pat. No. 5,468,589, EP 704762, EP762206, EP342498, EP553737 and described in ACS Symp. Ser. 614, Microelectronics Technology, pp. 35-55 (1995) and J. Photopolymer Sci. Technol. Vol. 10, No. 4 (1997), pp. 571-578. The polymer used in the present invention is not limited thereto.

With respect to polymers having acetal groups as acid-labile groups, it is possible to incorporate acid labile crosslinks as for example described in H.-T. Schacht, P. Falcigno, N. Muenzel, R. Schulz, and A. Medina, ACS Symp. Ser. 706 (Micro- and Nano-patterning Polymers), p. 78-94, 1997; H.-T. Schacht, N. Muenzel, P. Falcigno, H. Holzwarth, and J. Schneider, J. Photopolymer Science and Technology, Vol. 9, (1996), 573-586. This crosslinked system is preferred from the standpoint of heat resistance of the generated patterns.

Monomers with high activation energy acid labile groups are, for example, p-tert.-butoxycarbonyloxystyrene, tert.-butyl-acrylate, tert.-butyl-methacrylate, 2-methyl-2-adamantyl-methacrylate, isobornyl-methacrylate.

Monomers of type 1) suitable for ArF resist technology in particular include, for example, 2-methyl-2-adamantyl acrylate, 2-ethyl-2-adamantyl acrylate, 2-n-butyl-2-adamantyl acrylate, 2-n-butyl-2-adamantyl methacrylate, 2-methyl-2-adamantyl methacrylate, 2-ethyl-2-adamantyl methacrylate2-(1-adamantyl)isopropyl methacrylate, 2-(1-adamantyl)isopropyl acrylate, 2-(1-adamantyl)isobutyl methacrylate, 2-(1-adamantyl) isobutyl acrylate, t-butyl methacrylate, t-butyl acrylate, 1-methylcyclohexyl methacrylate, 1-methylcyclohexyl acrylate, 1-ethylcyclohexyl methacrylate, 1-ethylcyclohexyl acrylate, 1-(n-propyl)cyclohexyl methacrylate, 1-(n-propyl)cyclohexyl acrylate, tetrahydro-2-methacryloyloxy-2H-pyran and tetrahydro-2-acryloyloxy-2H-pyran. Other monomers comprising acid-labile adamantyl moieties are disclosed in JP2002-265530A, JP2002-338627A, JP2002-169290A, JP2002-241442A, JP2002-145954A, JP2002-275215A, JP2002-156750A, JP2002-268222A, JP2002-169292A, JP2002-162745A, JP2002-301161A, WO02/06901A2, JP2002-311590A, JP2002-182393A, JP2002-371114A, JP2002-162745A.

Particular olefins with acid labile-group are also suitable for ArF resist technology as shown in, for example, JP2002-308938a, JP2002-308869A, JP2002-206009A, JP2002-179624A, JP2002-161116A.

Examples of comonomers according to type 2) are:
aromatic vinyl monomers, such as styrene, α-methylstyrene, acetoxystyrene, α-methylnaphthylene, acenaphthylene, vinyl alicyclic compounds such as vinyl norbornane, vinyl adamantane. vinyl cyclohexane, alkyl (meth)acrylates such as methyl methacrylate, (meth)acrylonitrile, vinylcyclohexane, vinylcyclohexanol, itaconic anhydride, as well as maleic anhydride. Radically polymerizable monomers including functional moieties, such as glycidyl, oxetane and so on, are also preferred as a comonomer of type 2).

(Meth)acrylates such as glycidyl acrylate, glycidyl methacrylate, glycidyl alpha-ethylacrylate, glycidyl alpha-n-propylacrylate, glycidyl alpha-n-butylacrylate, 3,4-epoxybutyl acrylate, 3,4-epoxybutyl methacrylate, 4,5-epoxypentyl acrylate, 4,5-epoxypentyl methacrylate, 6,7-epoxyheptyl acrylate, 6,7-epoxyheptyl alpha-ethylacrylate and 6,7-epoxyheptyl methacrylate; vinylbenzyl glycidyl ethers such as o-vinylbenzyl glycidyl ether, m-vinylbenzyl glycidyl ether, p-vinylbenzyl glycidyl ether, alpha-methyl-o-vinylbenzyl glycidyl ether, alpha-methyl-m-vinyl benzyl glycidyl ether and alpha-methyl-p-vinylbenzyl glycidyl ether; p-vinylphenyl glycidyl ether; 3,4-epoxycyclohexylmethyl acrylate; and 3,4-epoxycyclohexylmethyl methacrylate. Among these, glycidyl acrylate, glycidyl methacrylate, p-vinylphenyl glycidyl ether, 3,4-epoxycyclohexylmethyl acrylate and 3,4-epoxycyclohexylmethyl methacrylate are preferred, and glycidyl acrylate and glycidyl methacrylate are more preferred.

Also, oxetane containing (meth)acrylates, such as (3-phenyl-3-oxetanyl)methyl acrylate, (3-phenyl-3-oxetanyl)methyl methacrylate, (3-ethyl-3-oxetanyl)methyl acrylate, (3-ethyl-3-oxetanyl)methyl methacrylate are preferred. Additionally a constituent unit having an oxetane group as the functional group may be formed using a compound where the epoxy group in those specific examples of the compound having an epoxy group as the functional group is replaced by an oxetane group.

Comonomers according to type 2) suitable for ArF resist technology in particular include, for example, alpha-acryloyloxy-gamma-butyrolactone, alpha-methacryloyloxy-gamma-butyrolactone, alpha-acryloyloxy-beta,beta-dimethyl-gamma-butyrolactone, alpha-methacryloyloxy-beta, beta-dimethyl-gamma-butyrolactone, alpha-acryloyloxy-alpha-methyl-gamma-butyrolactone, alpha-methacryloyloxy-alpha-methyl-gamma-butyrolactone, beta-acryloyloxy-gamma,beta-methacryloyloxy-alpha-methyl-gamma-butyrolactone, 5-acryloyloxy-2,6-norbornanecarbolactone, 5-methacryloyloxy-2,6-norbonane-carbolactone, 2-norbornene, methyl 5-norbornene-2-carboxylate, tert-butyl 5-norbornene-2-carboxylate, 1-cyclohexyl-1-methylethyl 5-norbornene-2-carboxylate, 1-(4-methylcyclohexyl)-1-methylethyl 5-norbornene-2-carboxylate, 1-methyl-1-(4-oxocyclo-hexyl)ethyl 5-norbornene-2-carboxylate, 1-(1-adamatyl)-1 methylethyl 5-norbornene-2-carboxylate,1-methylcyclohexyl 5-norbornene-2-carboxylate, 2-methyl-2-adamantyl 5-norbornene-2-carboxylate, 2-ethy-2-adamantyl 5-norbornene-2carboxylate, 5-norbornene-2,3-dicarboxylic acid anhydrate, 2(5H)-furanone, 3-vinyl-gamma-butyrolactone, 3-methacryloyloxybicyclo[4,3,0]nonane, 3-acryloyloxybicyclo[4,3,0]nonane, 1-adamantyl methacrylate, 1-adamantyl acrylate, 3-methacryloyloxymethyltetracyclo-[4,4,0,1$^{2,5}$, 1$^{7,10}$]dodecane, 3-acryloyloxymethyltetracyclo[4,4,0,1$^{2,5}$, 1$^{7,10}$]dodecane, 2-methacryloyloxynorbornane, 2-acryloyloxynorbornane, 2-methacryloyloxyisobornane, 2-acryloyloxyisobornane, 2-methacryloyloxymethylnorbornane, 2-acryloyloxymethyl-norbornane.

Examples of comonomers according to type 3) are:
vinyl aromatic compounds such as hydroxystyrene, acrylic acid compounds such as methacrylic acid, ethylcarbonyloxystyrene and derivatives of thereof. These polymers are described, for example, in U.S. Pat. No. 5,827,634, U.S. Pat. No. 5,625,020, U.S. Pat. No. 5,492,793, U.S. Pat. No. 5,372,912, EP 660187, U.S. Pat. No. 5,679,495, EP813113 and EP831369. Further examples are crotonic acid, isocrotonic acid, 3-butenoic acid, acrylic acid, 4-pentenoic acid, propiolic acid, 2-butynoic acid, maleic acid, fumaric acid, and acetylenecarboxylic acid. The polymer used in the present invention is not limited thereto.

Comonomers according to type 3) suitable for ArF resist technology in particular include, for example, 3-hydroxy-1- adamantyl acrylate, 3-hydroxy-1-adamantyl methacrylate, 3,5-dihydroxy-1-adamantyl acrylate, 3,5-dihydroxy-1-adamantyl methacrylate, 2-hydroxy-5-norbornene, 5-norbornene-2-carboxylic acid, 1-(4-hydroxycyclohexyl)-1-methylethyl 5-norbornene-2-carboxylate, 2-hydroxy-1-ethyl 5-norbornene-2-carboxylate, 5-norbornene-2methanol, 8-hydroxymethyl-4-methacryloyloxymethyltricyclo-[5.2.1.0$^{2.6}$]decane, 8-hydroxymethyl-4-acryloyloxymethyl-tricyclo[5.2.1.0$^{2.6}$]decane, 4-hydroxymethyl-8-methacryloyloxymethyltricyclo[5.2.1.0$^{2.6}$]decane, 4-hydroxymethyl-8-acryloyloxymethyltricyclo[5.2.1.0$^{2.6}$]decane.

Other monomers comprising lactone moieties suitable for ArF technology are disclosed in, for example, JP2002-006502A, JP2002-145955A, EP1127870A1, JP2002-357905A, JP2002-296783A. Other olefins suitable for ArF technology are published in, for example, JP2002-351078A, JP2002-234918A, JP2002-251009A, EP1127870A, JP2002-328475A, JP2002-278069A, JP2003-43689A, JP2002-202604A, WO01/86353, JP2002-023371A, JP2002-072484A, JP2002-202604A, JP2001-330959A, JP2002-003537A, JP2002-030114A, JP2002-278071A, JP2002-251011A, JP2003-122010A, JP2002-139837A, JP2003-195504A, JP2001-264984A, JP2002-278069A, JP2002-328475A, U.S. Pat. No. 6,379,861, U.S. Pat. No. 6,599,677, US2002/119391, U.S. Pat. No. 6,277,538, US2003/78354.

The content of acid labile monomers in the polymer may vary over a wide range and depends on the amount of the other comonomers and the alkaline solubility of the deprotected polymer. Typically, the content of monomers with acid labile groups in the polymer is between 5 and 60 mol %. If the content is too small, too low development rates and residues of the photosensitive resin composition in the exposed areas result. If the content of acid labile monomers is too high, generated patterns are poorly defined (eroded) after development and narrow features cannot be resolved anymore and/or the pattern looses its adhesion to the substrate during development.

Preferably the copolymers which have acid labile groups have a $M_W$ of from about 3'000 to about 200'000, more preferably from about 5'000 to about 50'000 with a molecular weight distribution of about 3 or less, more preferably a molecular weight distribution of about 2 or less. Non-phenolic polymers, e.g. a copolymer of an alkyl acrylate such as t-butyl acrylate or t-butyl-methacrylate and a vinyl alicyclic compound, such as a vinyl norbonanyl or vinyl cyclohexanol compound, also may be prepared by such free radical polymerization or other known procedures and suitably will have a $M_W$ of from about 8'000 to about 50'000, and a molecular weight distribution of about 3 or less. Other comonomers may suitably be added in an appropriate amount for the purpose of controlling the glass transition point of the polymer and the like.

In the present invention a mixture of two or more polymers having acid-labile groups may be used. For example, use may be made of a mixture of a polymer having acid-labile groups, which are cleaved very easily, such as acetal groups or tetrahydropyranyloxy-groups and a polymer having acid-cleavable groups, that are less easily cleaved, such as for example tertiary alkyl ester groups. Also, acid cleavable groups of different size can be combined by blending two or more polymers having different acid cleavable groups, such as a tert-butylester group and 2-methyl-adamantyl group or an 1-ethoxy-ethoxy group and a tetrahydropyranyloxy group. A mixture of a non-crosslinked resin and a crosslinked resin may also be used. The amount of these polymers in the present invention is preferably from 30 to 99% by weight, more preferably from 50 to 98% by weight, based on the total amount of all solid components. An alkali-soluble resin or monomeric or oligomeric compound having no acid-labile groups may be further incorporated into the composition in order to control the alkali solubility.

Examples of polymer blends with polymers having different acid-labile groups are given in EP 780732, EP679951 and U.S. Pat. No. 5,817,444.

Especially suitable examples of copolymers comprising acetal group as acid-labile moieties are 1-ethoxyethylmethacrylate/tert-butylmethacrylate/glycidylmethacrylate copolymer, 1-ethoxyethyl methacrylate/tert-butyl methacrylate/glycidylmethacrylate/methacrylic acid copolymer, 1-ethoxyethyl methacrylate/tetrahydro-2H-pyran-2-yl methacrylate/glycidyl methacrylate/methacrylic acid copolymer, 1-ethoxyethyl methacrylate/tert-butyl methacrylate/3,4-epoxycyclohexylmethyl methacrylate copolymer, 1-ethoxyethyl methacrylate/tert-butyl methacrylate/3,4-epoxycyclohexylmethyl methacrylate/methacrylic acid copolymer, 1-ethoxyethyl methacrylate/tert-butyl methacrylate/3,4-epoxycyclohexylmethyl methacrylate/(3-methacryloyloxy-2-hydroxypropyl) 4-hydroxybenzoate copolymer, 1-ethoxyethyl methacrylate/tert-butyl methacrylate/3,4-epoxycyclohexylmethyl methacrylate/(3-methacryloyloxypropyl)-4-hydroxybenzoate copolymer, 1-ethoxyethyl methacrylate/tert-butyl methacrylate/3,4-epoxycyc-10-hexylmethyl methacrylate/(3-methacryloyloxypropyl)-4-hydroxybenzoate/2-hydroxyethyl methacrylate copolymer, 1-ethoxyethyl methacrylate/tert-butyl methacrylate/3,4-epoxycyclohexylmethyl methacrylate/(3-methacryloyloxypropyl)-4-hydroxybenzoate/-methyl methacrylate copolymer, 1-ethoxyethyl methacrylate/tetrahydro-2H-pyran-2-yl methacrylate/3,4-epoxycyclohexyl methyl methacrylate/(3-methacryloyloxypropyl)-4-hydroxybenzoate copolymer, 1-ethoxyethyl methacrylate/tetrahydro-2H-pyran-2-yl methacrylate/3,4-epoxycyclohexylmethyl methacrylate/(3-methacryloyloxypropyl) 4-hydroxybenzoate/2-hydroxyethyl methacrylate copolymer, 1-ethoxyethyl methacrylate/tert-butyl methacrylate/3,4-epoxycyclohexyl-methyl acrylate/(3-methacryloyloxypropyl)-4-hydroxybenzoate copolymer, 1-ethoxyethyl methacrylate/tert-butyl methacrylate/3,4-epoxycyclohexyl methyl acrylate/(3-methacryloyloxypropyl)4-hydroxybenzoate/-2-hydroxyethyl methacrylate copolymer, 1-ethoxyethyl methacrylate/tert-butyl methacrylate/(3-ethyloxetan-3-yl)methyl methacrylate copolymer, 1-ethoxyethyl methacrylate/tert-butyl methacrylate/(3-ethyloxetan-3-yl)methyl methacrylate/methacrylic acid copolymer, 1-ethoxyethyl methacrylate/tert-butyl methacrylate/(3-ethyloxetan-3-yl)methyl methacrylate/(3-methacryloyloxy-2-hydroxypropyl)-4-hydroxybenzoate co-polymer, 1-ethoxyethyl methacrylate/tert-butyl methacrylate/(3-ethyloxetan-3-yl)methyl methacrylate/(3-methacryloyloxypropyl)-4-hydroxybenzoate copolymer, 1-ethoxyethyl methacrylate/2-methyl-2-adamantyl methacrylate/(3-ethyloxetan-3-yl)methyl methacrylate/(3-methacryloyloxypropyl)-4-hydroxybenzoate copolymer, 1-ethoxyethyl methacrylate/I-methyl-1-cyclohexyl methacrylate/(3-ethyloxetan-3-yl)methyl methacrylate/(3-methacryloyloxypropyl) 4-hydroxybenzoate copolymer, 1-ethoxyethyl methacrylate/tert-butyl methacrylate/(3-ethyloxetan-3-yl)methyl methacrylate/(2-methacryloyloxyethyl)4-hydroxybenzoate copolymer, 1-ethoxyethyl methacrylate/tert-butyl methacrylate/(3-ethyloxetan-3-yl)methyl methacrylate/(6-methacryloyloxyhexyl)-4-hydroxybenzoate copolymer, 1-ethoxyethyl methacrylate/tert-butyl methacrylate/(3-ethyloxetan-3-yl)methyl methacrylate/(3-methacryloyloxypropyl)4-hydroxybenzoate/2-hydroxyethyl methacrylate copolymer, 1-ethoxyethyl methacrylate/tert-butyl methacrylate/(3-ethyloxetan-3-yl)methyl methacrylate/(3-methacryloyloxypropyl)-4-hydroxybenzoate/-methyl methacrylate copolymer, 1-ethoxyethyl methacrylate/tetrahydro-2H-pyran-2-yl methacrylate/(3-ethyloxetan-3-yl)methyl methacrylate/(3-methacryloyloxypropyl)-4-hydroxybenzoate copolymer, 1-ethoxyethyl methacrylate/tetrahydro-2H-pyran-2-yl methacrylate/(3-ethyloxetan-3-yl)methyl methacrylate/(3-methacryloyloxypropyl)-4-hydroxybenzoate/2-hydroxyethyl methacrylate copolymer, 1-ethoxyethyl methacrylate/tert-butyl methacrylate/(3-ethyloxetan-3-yl)methyl acrylate/(3-methacryloyloxypropyl)-4-hydroxybenzoate copolymer, 1-ethoxyethyl methacrylate/tert-butyl methacrylate/(3-ethyloxetan-3-yl)methyl acrylate/(3-methacryloyloxypropyl)-4-hydroxybenzoate/-2-hydroxyethyl methacrylate copolymer, 1-(cyclohexyloxy)ethyl methacrylate/tert-butyl methacrylate/3,4-epoxycyclohexylmethyl methacrylate copolymer, 1-(cyclohexyl-oxy)ethyl methacrylate/tert-butyl methacrylate/3,4-epoxycyclohexylmethyl methacrylate/(3-methacryloyloxypropyl)-4-hydroxybenzoate/2-hydroxyethyl methacrylate copolymer, 1-(cyclohexyloxy)ethyl methacrylate/tert-butyl methacrylate/(3-ethyloxetan-3-yl)methyl methacrylate copolymer, 1-(cyclohexyloxy)ethyl methacrylate/tert-butyl meth-acrylate/(3-ethyloxetan-3-yl)methyl methacrylate/(3-methacryloyloxypropyl)-4-hydroxybenzoate/2-hydroxyethyl methacrylate copolymer, 1-(cyclohexyloxy)ethyl methacrylate/tetrahydro-2H-pyran-2-yl methacrylate/3,4-epoxycyclohexylmethyl methacrylate/(3-methacryloyloxypropyl)-4-hydroxybenzoate/2-hydroxyethyl methacrylate copolymer, 1-(cyclohexyloxy)ethyl methacrylate/tetrahydro-2H-pyran-2-yl methacrylate/(3-ethyloxetan-3-yl)methyl methacrylate/(3-methacryloyloxypropyl) 4-hydroxybenzoate/2-hydroxyethyl methacrylate copolymer, 1-ethoxyethyl ether of (3-methacryloyloxypropyl)-4-hydroxybenzoate/tert-butyl methacrylate/(3-ethyloxetan-3-yl)methyl meth-acrylate/methacrylic acid copolymer, 1-ethoxyethyl ether of (3-methacryloyloxypropyl)4-hydroxybenzoate/tert-butoxycarbonyl grou p-protected-alpha-methyl-para-hydroxystyrene/(3-ethyloxetan-3-yl)methyl methacrylate/methacrylic acid copolymer, 1-ethoxyethyl ether of (2-methacryloyloxyethyl)-4-hydroxybenzoate/tert-butyl group-protected 4-hydroxyphenylmethacrylate/(3-ethyloxetan-3-yl)methyl methacrylate/methacrylic acid copolymer, 1-ethoxyethyl-methacrylate/styrene/glycidylmethacrylate/methacrylic acid copolymer, 1-ethoxyethyl methacrylate/N-cyclohexylmaleimide/glycidyl methacrylate/methacrylic acid copolymer, tetrahydrofuran-2-yl methacrylate/(tricycle-[5.2.1.0$^{2,6}$]decan-8-yl)methacrylate/(3-ethyloxetan-3-yl)methyl meth-acrylate/methacrylic acid copolymer, and tetrahydrofuran-2-yl methacrylate/(tricyclo[5.2.1.0$^{2,6}$]decan-8-yl) methacrylate/glycidyl methacrylate/methacrylic acid copolymer.

Furthermore, the constituent unit having an acid labile group that is decomposed by an acid to form a carboxyl group may be formed by polymerizing a monomer containing a carboxyl group that is to be protected with a carboxylic acid monomer or a precursor thereof and then reacting the carboxyl group with a vinyl ether compound. Specific preferred examples of a monomer unit formed as above include a monomer unit derived from the specific preferred examples of the radically polymerizable monomer.

Preferably monomeric and oligomeric dissolution inhibitors (a2) are used in the present invention.

The monomeric or oligomeric dissolution inhibitor having the acid-labile group for use in the present invention is a compound which has at least one acid-labile group in the molecular structure, which decomposes in the presence of acid to increase the solubility in aqueous alkaline developer solution. Examples are alkoxymethyl ether groups, tetrahydrofuranyl ether groups, tetrahydropyranyl ether groups, alkoxyethyl ether groups, trityl ether groups, silyl ether groups, alkyl carbonate groups, trityl ester groups, silyl ester groups, alkoxymethyl ester groups, vinyl carbamate groups, tertiary alkyl carbamate groups, trityl amino groups, cumyl ester groups, acetal groups, ketal groups, tetrahydropyranyl ester groups, tetrafuranyl ester groups, tertiary alkyl ether groups, tertiary alkyl ester groups, and the like. The molecular weight of the acid-decomposable dissolution inhibitive compound for use in the present invention is 3'000 or lower, preferably from 100 to 3'000, more preferably from 200 to 2'500.

Examples of monomeric and oligomeric dissolution inhibitors having acid-labile groups are described as formulae (I) to (XVI) in EP0831369. Other suitable dissolution inhibitors having acid-labile groups are shown in U.S. Pat. No. 5,356,752, U.S. Pat. No. 5,037,721, U.S. Pat. No. 5,015,554, JP01-289946A, JP01-289947A, JP02-002560A, JP03-128959A, JP03-158855A, JP03-179353A, JP03-191351A, JP03-200251A, JP03-200252A, JP03-200253A, JP03-200254A, JP03-200255A, JP03-259149A, JP03-279958A, JP03-279959A, JP04-001650A, JP04-001651A, JP04-011260A, JP04-012356A, JP04-123567A and JP04-271349A, JP05-45869A, JP05-158233A, JP05-257275A, JP05-297581A, JP05-297583A, JP05-303197A, JP05-303200A and JP05-341510A.

The composition can also contain polymeric dissolution inhibitors, for example, polyacetals as described for example in U.S. Pat. No. 5,354,643 or poly-N,O-acetals for example those described in U.S. Pat. No. 5,498,506, either in combination with an alkaline soluble polymer, or in combination with a polymer containing acid labile groups which increase the solubility of the coated film in the developer after exposure, or with a combination of both types of polymers.

In the case where the dissolution inhibitor having acid-labile groups is used in the present invention in combination with the compounds of formula I, the alkali-soluble polymer and/or the polymer having acid-labile groups, the amount of the dissolution inhibitor is from 3 to 55% by weight, preferably from κ to 45% by weight, most preferably from 10 to 35% by weight, based on the total amount of all solid components of the photosensitive composition.

A polymer soluble in an aqueous alkali solution (a3) is preferably used in the present invention. Examples of these polymers include novolak resins, hydrogenated novolak resins, acetone-pyrogallol resins, poly(o-hydroxystyrene), poly(m-hydroxystyrene), poly(p-hydroxystyrene), hydrogenated poly(hydroxystyrene)s, halogen- or alkyl-substituted poly(hydroxystyrene)s, hydroxystyrene/N-substituted maleimide copolymers, o/p- and m/p-hydroxystyrene copolymers, partially o-alkylated poly-(hydroxystyrene)s, [e.g., o-methylated, o-(1-methoxy)ethylated, o-(1-ethoxy)ethylated, o-2-tetrahydropyranylated, and o-(t-butoxycarbonyl) methylated poly(hydroxystyrene)s having a degree of substitution of from 5 to 30 mol % of the hydroxyl groups], o-acylated poly(hydroxystyrene)s [e.g. o-acetylated and o-(t-butoxy)carbonylated poly-(hydroxystyrene)s having a degree of substitution of from 5 to 30 mol % of the hydroxyl groups], styrene/maleic anhydride copolymers, styrene/hydroxystyrene copolymers, α-methylstyrene/hydroxystyrene copolymers, carboxylated methacrylic resins, and derivatives thereof. Further suitable are poly (meth)acrylic acid [e.g. poly(acrylic acid)], (meth)acrylic acid/(meth)acrylate copolymers [e.g. acrylic acid/methyl acrylate copolymers, methacrylic acid/methyl methacrylate copolymers or methacrylic acid/methyl methacrylate/t-butyl methacrylate copolymers], (meth)acrylic acid/alkene copolymers [e.g. acrylic acid/ethylene copolymers], (meth)acrylic acid/(meth)acrylamide copolymers [e.g. acrylic acid/acrylamide copolymers], (meth)acrylic acid/vinyl chloride copolymers [e.g. acrylic acid/vinyl chloride copolymers], (meth)acrylic acid/vinyl acetate co-polymer [e.g. acrylic acid/vinyl acetate copolymers], maleic acid/vinyl ether copolymers [e.g. maleic acid/methyl vinyl ether copolymers], maleic acid mono ester/methyl vinyl ester copolymers [e.g. maleic acid mono methyl ester/methyl vinyl ether copolymers], maleic acid/(meth)acrylic acid copolymers [e.g. maleic acid/acrylic acid copolymers or maleic acid/methacrylic acid copolymers], maleic acid/(meth)acrylate copolymers [e.g. maleic acid/methyl acrylate copolymers], maleic acid/vinyl chloride copolymers, maleic acid/vinyl acetate copolymers and maleic acid/alkene copolymers [e.g. maleic acid/ethylene copolymers and maleic acid/1-chloropropene copolymers]. However, the alkali-soluble polymer for use in the present invention should not be construed as being limited to these examples.

Especially preferred alkali-soluble polymers (a3) are novolak resins, poly(o-hydroxystyrene), poly(m-hydroxystyrene), poly(p-hydroxystyrene), copolymers of the respective hydroxystyrene monomers, for example with p-vinylcyclohexanol, alkyl-substituted poly(hydroxystyrene)s, partially o- or m-alkylated and o- or m-acylated poly(hydroxystyrene)s, styrene/hydroxystyrene copolymer, and α-methylstyrene/-hydroxystyrene copolymers. The novolak resins are obtained by addition-condensing one or more given monomers as the main ingredient with one or more aldehydes in the presence of an acid catalyst.

Examples of monomers useful in preparing alkaline soluble resins include hydroxylated aromatic compounds such as phenol, cresols, i.e., m-cresol, p-cresol, and o-cresol, xylenols, e.g., 2,5-xylenol, 3,5-xylenol, 3,4-xylenol, and 2,3-xylenol, alkoxyphenols, e.g., p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol, and p-butoxyphenol, dialkylphenols, e.g., 2-methyl-4-isopropylphenol, and other hydroxylated aromatics including m-chlorophenol, p-chlorophenol, o-chlorophenol, dihydroxybiphenyl, bisphenol A, phenylphenol, resorcinol, and naphthol. These compounds may be used alone or as a mixture of two or more thereof. The main monomers for novolak resins should not be construed as being limited to the above examples.

Examples of the aldehydes for polycondensation with phenolic compounds to obtain novolaks include formaldehyde, p-formaldehyde, acetaldehyde, propionaldehyde, benzaldehyde, phenylacetaldehyde, α-phenylpropionaldehyde, β-phenylpropionaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde, and acetals derived from these, such as chloroacetaldehyde diethyl acetal. Preferred of these is formaldehyde.

These aldehydes may be used alone or in combination of two or more thereof. Examples of the acid catalyst include hydrochloric acid, sulfuric acid, formic acid, acetic acid, and oxalic acid.

The weight-average molecular weight of the thus-obtained novolak resin suitably is from 1'000 to 30'000. If the weight-average molecular weight thereof is lower than 1'000, the film reduction at unexposed parts during development is liable to be large. If the weight-average molecular weight there of exceeds 50'000, the developing rate may be too low. The especially preferred range of the molecular weight of the novolak resin is from 2'000 to 20'000.

The poly(hydroxystyrene)s and derivatives and copolymers thereof shown above as alkali-soluble polymers other than novolak resins each have a weight-average molecular weight of 2'000 or higher, preferably from 4'000 to 200'000, more preferably from 5'000 to 50'000. From the standpoint of obtaining a polymer film having improved heat resistance, the weight-average molecular weight thereof is desirably at least 5'000 or higher.

Weight-average molecular weight in the context of the present invention is meant to be the one determined by gel permeation chromatography and calibrated for with polystyrene standard.

In the present invention the alkali-soluble polymers may be used as a mixture of two or more thereof. In the case where a mixture of an alkali-soluble polymer and the polymer having groups which decompose by the action of an acid to enhance solubility in an alkaline developing solution is used, the addition amount of the alkali-soluble polymer is preferably up to 80% by weight, more preferably up to 60% by weight, most preferably up to 40% by weight, based on the total amount of the photosensitive composition (excluding the solvent). The amount exceeding 80% by weight is undesirable because the generated pattern suffers a considerable decrease in thickness, resulting in poor images and low resolution.

In the case where an alkali-soluble polymer is used together with a dissolution inhibitor, without the polymer having groups which decompose by the action of an acid, to enhance solubility in an alkaline developing solution, the amount of the alkali-soluble polymer is preferably from 40% to 90% by weight, more preferably from 50 to 85% by weight, most preferably 60 to 80% by weight. If the amount thereof is smaller than 40% by weight, undesirable results such as reduced sensitivity are caused. On the other hand, if it exceeds 90% by weight, the pattern suffers a considerable decrease in film thickness, resulting in poor resolution and image reproduction.

The use of the oxime sulfonate derivatives according to the invention in chemically amplified systems, which operates on the principle of the removal of a protecting group from a polymer, generally produces a positive photosensitive resin composition. Positive compositions are preferred over negative compositions in many applications, especially because of their higher resolution. There is, however, also interest in producing a negative image using the positive mechanism, in order to combine the ad-vantages of the high degree of resolution of the positive with the properties of the negative. This can be achieved by introducing a so-called image-reversal step as described, for example, in EP361906. For this purpose, the image-wise irradiated photosensitive resin composition material is before the developing step treated with, for example, a gaseous base, thereby imagewise neutralizing the acid which has been produced. Then, a second irradiation, over the whole area, and thermal aftertreatment are carried out and the negative image is then developed in the customary manner.

The compounds of the formula I according to the present invention are in particular suitable as photolatent acids in the ArF resist technology, i.e. a technology using ArF excimer lasers (193 nm) for the imaging step. This technology requests the use of specific polymers/copolymers. Suitable formulations and the preparation of suitable polymer/copolymers are for example published in *Proceeding of SPIE* 2438, 474 (1995); *Proceeding of SPIE* 3049, 44 (1997); *Proceeding of SPIE* 3333, 144 (1998); *J. Photopolym. Sci Technol* 14, 631 (2001); *Proceeding of SPIE* 3333, 546 (1998); *J. Photopolym. Sci Technol.* 13, 601 (2000); JP2001-242627A; JP2001-290274A; JP2001-235863A; JP2001-228612A; *Proceeding of SPIE* 3333, 144 (1998); JP2001-5184A, commercially available as Lithomax alpha-7K from Mitsubishi Rayon; JP2001-272783A; U.S. patent application Ser. No. 09/413,763 (filed 1999 Oct. 7); EP 1091249; JP2000-292917A; JP2003-241385A; *J. Photopolym. Sci Technol.* 14, 631 (2001); *Proceeding of SPIE* 3333, 11 (1998); ACS 1998 (University of Texas); JP2001-290274A; JP2001-235863A; JP2001-228612A; *Proceeding of SPIE* 3999, 13 (2000); JP2001-296663A; U.S. patent application Ser. No. 09/567,814 (filed 2000 May 9); EP 1128213; *Proceeding of SPIE* 3049, 104 (1997); *J. Photopolym. Sci Technol.* 10, 521 (1997); JP2001-290274A; JP2001-235863A; JP2001-228612A; *Proceeding of SPIE* 4345, 680 (2001); *J. Vac. Sci Technol. B* 16(6), p. 3716, 1998; *Proceeding of SPIE* 2724, 356 (1996); *Proceeding of SPIE* 4345, 67 (2001); *Proceeding of SPIE* 3333, 546 (1998); *Proceeding of SPIE* 4345, 87 (2001); *Proceeding of SPIE* 4345, 159 (2001); *Proceeding of SPIE* 3049, 92 (1997); *Proceeding of SPIE* 3049, 92 (1997); *Proceeding of SPIE* 3049, 92 (1997); *Proceeding of SPIE* 3999, 2 (2000); *Proceeding of SPIE* 3999, 23 (2000); *Proceeding of SPIE* 3999, 54 (2000); *Proceeding of SPIE* 4345, 119 (2001).

The formulations disclosed in the aforementioned publications are incorporated herein by reference. It is understood, that the compounds of the present invention are in particular suitable for use as photolatent acid in all the polymers/copolymers and compositions described in these cited publications.

The compounds of the formula (I) or (IA) according to the present invention are suitable as photolatent acids in the bi-layer resist. This technology requests the use of specific polymers/copolymers. Suitable formulations and the preparation of suitable polymer/copolymers are for example published in Proc. SPIE 4345, 361-370 (2001), Proc. SPIE 4345, 406-416 (2001), JP2002-278073A, JP2002-30116A, JP2002-030118A, JP2002-072477A, JP2002-348332A, JP2003-207896A, JP2002-082437A, US2003/65101, US2003/64321.

The compounds of the formula (I) or (IA) according to the present invention are suitable as photolatent acids in the multi-layer resist. This technology requests the use of specific polymers/copolymers. Suitable formulations and the preparation of suitable polymer/copolyers are for example published in JP2003-177540A, JP2003-280207A, JP2003-149822A, JP2003-177544A.

In order to make fine hole pattern, thermal flow process or chemical shrink technology, so-called RELACS (resolution enhancement lithography assisted by chemical shrink) process, are applied for chemically amplified photosensitive resin composition. The compounds of the formula I according to the present invention are suitable as photolatent acids in the compositions for thermal flow process or RELACS process. These technologies request the use of specific polymers/copolymers. Suitable formulations and the preparation of suitable polymer/copolymers are for example published in JP2003-167357A, JP2001-337457A, JP2003-066626A, US2001/53496, *Proceeding of SPIE* 5039, 789 (2003), *IEDM98, Dig.*, 333 (1998), *Proceeding Silicon Technology* 11, 12 (1999), The compounds of the formula (I) and (IA) according to the present invention are suitable as photolatent acids in the chemically amplified resist for immersion lithography. This technology reduces minimum feature size of resist pattern using liquid medium between the light source and the resist as described in *Proceeding of SPIE* 5040, 667 (2003), *Proceeding of SPIE* 5040, 679 (2003), *Proceeding of SPIE* 5040, 690 (2003), *Proceeding of SPIE* 5040, 724 (2003).

The compounds of the formula (I) or (IA) according to the present invention are suitable as photolatent acids in the positive and negative photosensitive polyimide. This technology requests the use of specific polymers/copolymers. Suitable formulations and the preparation of suitable polymer/copolymers are for example published in JP09-127697A, JP10-307393A, JP10-228110A, JP10-186664A, JP11-338154A, JP11-315141A, JP11-202489A, JP11-153866A, JP11-084653A, JP2000-241974A, JP2000-221681A, JP2000-034348A, JP2000-034347A, JP2000-034346A, JP2000-026603A, JP2001-290270A, JP2001-281440A, JP2001-264980A, JP2001-255657A, JP2001-214056A, JP2001-214055A, JP2001-166484A, JP2001-147533A, JP2001-125267A, JP2001-083704A, JP2001-066781A, JP2001-056559A, JP2001-033963A, JP2002-356555A, JP2002-356554A, JP2002-303977A, JP2002-284875A, JP2002-268221A, JP2002-162743A, JP2002-122993A, JP2002-99084A, JP2002-040658A, JP2002-037885A, JP2003-026919A.

The formulations disclosed in the aforementioned publications are incorporated herein by reference. It is understood, that the compounds of the present invention are in particular suitable for use as photolatent acid in all the polymers/copolymers and compositions described in these cited publications.

The difference in solubility between irradiated and non-irradiated sections that occurs as a result of the reaction of the material by an acid during or after irradiation may be of two types depending upon which further constituents are present in the photosensitive resin composition. If the compositions according to the invention comprise components that decrease the solubility of the composition in the developer after irradiation, the photosensitive resin composition is negative.

Subject of the invention also is a chemically amplified negative photosensitive resin composition.

The invention includes, as a special embodiment a chemically amplified negative alkaline-developable photosensitive resin composition, comprising
(a4) an alkali-soluble resin as binder;
(a5) a component which is cationically or acid-catalytically polymerizable or crosslinkable with itself and/or with the other components; and
(b) at least one compound of formula (I) or (IA).

A further embodiment of the invention is a chemically amplified negative alkaline-developable photosensitive resin composition, comprising
(a5) a component which is cationically or acid-catalytically polymerizable or crosslinkable with itself and/or with the other components; and
(b) at least one compound of formula (I) or (IA).

The subject composition includes, as a special embodiment, chemically amplified negative solvent-developable photosensitive resin composition, comprising (a5) a component which is cationically or acid-catalytically polymerizable or crosslinkable with itself and/or with the other components; and (b) at least one compound of formula (I) or (IA).

Another specific embodiment of the invention resides in a chemically amplified negative solvent-developable photosensitive resin composition, comprising (a5) a component which is cationically or acid-catalytically polymerizable or crosslinkable with itself and/or with the other components;

(a6) a solvent-developable resin as binder; and (b) at least one compound of formula (I) or (IA).

The composition may comprise additionally to the component (b) other photosensitive acid donors (b1), other photoinitiators (d), sensitizers (e) and/or other additives (c).

The invention also pertains to a chemically amplified negative photosensitive resin composition, comprising (a4) an alkali-soluble resin as binder; and/or (a6) a solvent-developable resin as binder; and/or (a5) a component which is cationically or acid-catalytically polymerizable or crosslinkable with itself and/or with the other components; and (b) as photosensitive acid donor, at least one compound of the formula (I) or (IA).

The composition may comprise additionally to the components (a) and (b), or components (a1), (a2), (a3) and (b), or components (a4), (a5), (a6) and (b), further additives (c), further photosensitive acid donor compounds (b1), other photoinitiators (d), and/or sensitizers (e).

Acid-sensitive components (a5) that produce a negative tone composition characteristically are especially compounds which are capable of undergoing a cationic or acidcatalytic polymerization or cross-linking reaction with themselves and/or with one or more further components of the composition by an acid (e.g. the acid formed during irradiation of the compounds of formula (I) or (IA)). Examples thereof include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, or mixtures thereof. Amino resins, phenolic resins and epoxy resins are very suitable. Acid-curable resins are generally known and are described, for example, in Wagner, Sarx/Lackkunstharze (Munich, 1971), pages 86 to 123 and 229 to 238, or in Ullmann/Encyclopädie der techn. Chemie, 4$^{th}$ edition, volume 15 (1978), pages 613 to 628, or Ullmann's Encyclopedia of Industrial Chemistry, Verlag Chemie, 1991, Vol. 18, 360 ff., Vol. A19, 371 ff.

It is possible, for example, to use all customary epoxides, such as aromatic, aliphatic or cycloaliphatic epoxy resins. These are compounds having at least one, preferably at least two, epoxy group(s) in the molecule. Examples thereof are the glycidyl ethers and p-methyl glycidyl ethers of aliphatic or cycloaliphatic diols or polyols, e.g. those of ethylene glycol, propane-1,2-diol, propane-1,3-diol, butane-1,4-diol, diethylene glycol, polyethylene glycol, polypropylene glycol, glycerol, trimethylolpropane or 1,4-dimethylolcyclohexane or of 2,2-bis(4-hydroxycyclohexyl)propane and N,N-bis(2-hydroxyethyl)aniline; the glycidyl ethers of di- and poly-phenols, for example of resorcinol, of 4,4'-dihydroxyphenyl-2,2-propane, of novolaks or of 1,1,2,2-tetrakis(4-hydroxyphenyl)ethane. Examples thereof include phenyl glycidyl ether, p-tert-butyl glycidyl ether, oicresyl glycidyl ether, polytetrahydrofuran glycidyl ether, n-butyl glycidyl ether, 2-ethylhexylglycidylether, $C_{12/15}$alkyl glycidyl ether and cyclohexanedimethanol diglycidyl ether. Further examples include N-glycidyl compounds, for example the glycidyl compounds of ethyleneurea, 1,3-propyleneurea or 5-dimethyl-hydantoin or of 4,4'-methylene-5,5'-tetramethyl-dihydantoin, or compounds such as triglycidyl isocyanurate.

Further examples of glycidyl ether components (a5) that are used in the formulations according to the invention are, for example, glycidyl ethers of polyhydric phenols obtained by the reaction of polyhydric phenols with an excess of chlorohydrin, such as, for example, epichlorohydrin (e.g. glycidyl ethers of 2,2-bis(2,3-epoxypropoxyphenol)propane. Further examples of glycidyl ether epoxides that can be used in connection with the present invention are described, for example, in U.S. Pat. No. 3,018,262 and in "Handbook of Epoxy Resins" by Lee and Neville, McGraw-Hill Book Co., New York (1967).

There is also a large number of commercially available glycidyl ether epoxides that are suitable as component (a5), such as, for example, glycidyl methacrylate, diglycidyl ethers of bisphenol A, for example those obtainable under the trade names EPON 828, EPON 825, EPON 1004 and EPON 1010 (Shell); DER-331, DER-332 and DER-334 (Dow Chemical); 1,4-butanediol diglycidyl ethers of phenolformaldehyde novolak, e.g. DEN-431, DEN-438 (Dow Chemical); and resorcinol diglycidyl ethers; alkyl glycidyl ethers, such as, for example, $C_8$-$C_{10}$glycidyl ethers, e.g. HELOXY Modifier 7, $C_{12}$-$C_{14}$glycidyl ethers, e.g. HELOXY Modifier 8, butyl glycidyl ethers, e.g. HELOXY Modifier 61, cresyl glycidyl ethers, e.g. HELOXY Modifier 62, p-tert-butylphenyl glycidyl ethers, e.g. HELOXY Modifier 65, polyfunctional glycidyl ethers, such as diglycidyl ethers of 1,4-butanediol, e.g. HELOXY Modifier 67, diglycidyl ethers of neopentyl glycol, e.g. HELOXY Modifier 68, diglycidyl ethers of cyclohexanedimethanol, e.g. HELOXY Modifier 107, trimethylolethane triglycidyl ethers, e.g. HELOXY Modifier 44, trimethylolpropane triglycidyl ethers, e.g. HELOXY Modifier 48, polyglycidyl ethers of aliphatic polyols, e.g. HELOXY Modifier 84 (all HELOXY glycidyl ethers are obtainable from Shell).

Also suitable are glycidyl ethers that comprise copolymers of acrylic esters, such as, for example, styrene-glycidyl methacrylate or methyl methacrylate-glycidyl acrylate. Examples thereof include 1:1 styrene/glycidyl methacrylate, 1:1 methyl methacrylate/glycidyl acrylate, 62.5:24:13.5 methyl methacrylate/ethyl acrylate/glycidyl methacrylate.

The polymers of the glycidyl ether compounds can, for example, also comprise other functionalities provided that these do not impair the cationic curing.

Other glycidyl ether compounds suitable as component (a5) that are commercially available are polyfunctional liquid and solid novolak glycidyl ether resins, e.g. PY 307, EPN 1179, EPN 1180, EPN 1182 and ECN 9699.

It will be understood that mixtures of different glycidyl ether compounds may also be used as component (a5).

The glycidyl ethers (a5) are, for example, compounds of formula XX

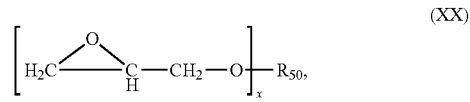

(XX)

wherein x is a number from 1 to 6; and $R_{50}$ is a mono- to hexavalent alkyl or aryl radical.

Preference is given, for example, to glycidyl ether compounds of formula XX, wherein x is the number 1, 2 or 3; and $R_{50}$ when x=1, is unsubstituted or $C_1$-$C_{12}$alkyl-substituted phenyl, naphthyl, anthracyl, biphenylyl, $C_1$-$C_{20}$alkyl, or $C_2$-$C_{20}$alkyl interrupted by one or more oxygen atoms, or $R_{50}$ when x=2, is 1,3-phenylene, 1,4-phenylene, $C_6$-$C_{10}$cycloalkylene, unsubstituted or halo-substituted $C_1$-$C_{40}$akylene, $C_2$-$C_{40}$alkylene interrupted by one or more oxygen atoms, or a group

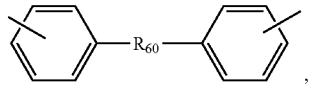, or $R_{50}$ when x=3, is a radical

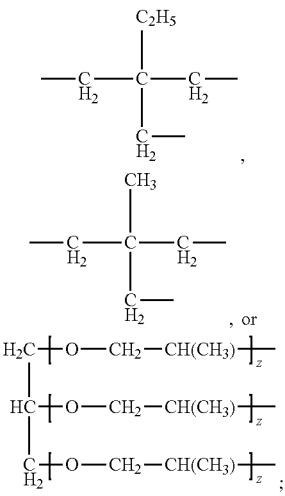, or

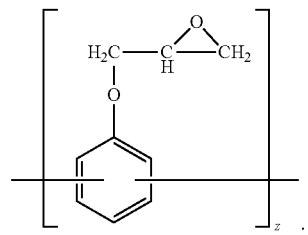;

z is a number from 1 to 10; and
$R_{60}$ is $C_1$-$C_{20}$alkylene, oxygen or

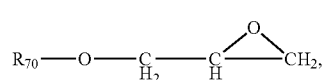.

The glycidyl ethers (a5) are, for example, compounds of formula XXa

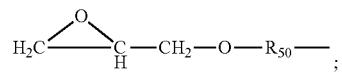 (XXa)

wherein $R_{70}$ is unsubstituted or $C_1$-$C_{12}$alkyl-substituted phenyl; naphthyl; anthracyl; biphenylyl; $C_1$-$C_{20}$alkyl, $C_2$-$C_{20}$alkyl interrupted by one or more oxygen atoms; or a group of formula

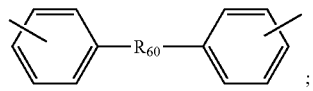;

$R_{50}$ is phenylene, $C_1$-$C_{20}$alkylene, $C_2$-$C_{20}$alkylene interrupted by one or more oxygen atoms, or a group

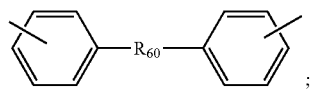;

and
$R_{60}$ is $C_1$-$C_{20}$alkylene or oxygen.

Preference is given to the glycidyl ether compounds of formula XXb

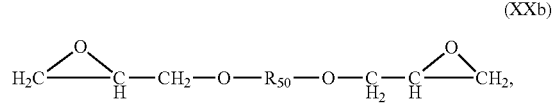 (XXb)

wherein $R_{50}$ is phenylene, $C_1$-$C_{20}$alkylene, $C_2$-$C_{20}$alkylene interrupted by one or more oxygen atoms, or a group

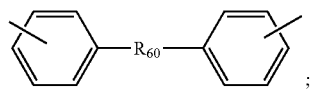;

and
$R_{60}$ is $C_1$-$C_{20}$alkylene or oxygen.

Further examples for component (a5) are polyglycidyl ethers and poly(β-methylglycidyl) ethers obtainable by the reaction of a compound containing at least two free alcoholic and/or phenolic hydroxy groups per molecule with the appropriate epichlorohydrin under alkaline conditions, or alternatively in the presence of an acid catalyst with subsequent alkali treatment. Mixtures of different polyols may also be used.

Such ethers can be prepared with poly(epichlorohydrin) from acyclic alcohols, such as ethylene glycol, diethylene glycol and higher poly(oxyethylene) glycols, propane-1,2-diol and poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylol-propane, pentaerythritol and sorbitol, from cycloaliphatic alcohols, such as resorcitol, quinitol, bis(4-hydroxycyclohexyl)methane, 2,2-bis(4-hydroxycyclohexyl) propane and 1,1-bis-(hydroxymethyl)cyclohex-3-ene, and from alcohols having aromatic nuclei, such as N,N-bis(2-hydroxyethyl)aniline and p,p'-bis(2-hydroxyethylamino)diphenylmethane.

They can also be prepared from mononuclear phenols, such as resorcinol and hydroquinone, and polynuclear phenols, such as bis(4-hydroxyphenyl)methane, 4,4-dihydroxydiphenyl, bis(4-hydroxyphenyl)sulphone, 1,1,2,2-tetrakis(4-hydroxyphenyl)ethane, 2,2-bis(4-hydroxyphenyl)-propane (bisphenol A) and 2,2-bis(3,5-dibromo-4-hydroxyphenyl) propane.

Further hydroxy compounds suitable for the preparation of polyglycidyl ethers and poly(β-methylglycidyl) ethers are the novolaks obtainable by the condensation of aldehydes, such as formaldehyde, acetaldehyde, chloral and furfural, with phenols, such as, for example, phenol, o-cresol, m-cresol, p-cresol, 3,5-dimethylphenol, 4-chlorophenol and 4-tert-butylphenol.

Poly(N-glycidyl) compounds can be obtained, for example, by dehydrochlorination of the reaction products of epichlorohydrin with amines containing at least two amino-hydrogen atoms, such as aniline, n-butylamine, bis(4-aminophenyl)methane, bis(4-aminophenyl)-propane, bis(4-methylaminophenyl)methane and bis(4-aminophenyl) ether, sulphone and sulphoxide. Further suitable poly(N-glycidyl) compounds include triglycidyl isocyanurate, and N,N'-diglycidyl derivatives of cyclic alkyleneureas, such as ethyleneurea and 1,3-propyleneurea, and hydantoins, such as, for example, 5,5-dimethylhydantoin.

Poly(S-glycidyl) compounds are also suitable. Examples thereof include the di-S-glycidyl derivatives of dithiols, such as ethane-1,2-dithiol and bis(4-mercaptomethylphenyl) ether.

There also come into consideration as component (a5) epoxy resins in which the glycidyl groups or β-methyl glycidyl groups are bonded to hetero atoms of different types, for example the N,N,O-triglycidyl derivative of 4-aminophenol, the glycidyl ether/glycidyl ester of salicylic acid or p-hydroxybenzoic acid, N-glycidyl-N'-(2-glycidyloxypropyl)-5,5-dimethyl-hydantoin and 2-glycidyloxy-1,3-bis(5,5-dimethyl-1-glycidylhydantoin-3-yl)propane.

Preference is given to diglycidyl ethers of bisphenols. Examples thereof include diglycidyl ethers of bisphenol A, e.g. ARALDIT GY 250, diglycidyl ethers of bisphenol F and diglycidyl ethers of bisphenol S. Special preference is given to diglycidyl ethers of bisphenol A.

Further glycidyl compounds of technical importance are the glycidyl esters of carboxylic acids, especially di- and poly-carboxylic acids. Examples thereof are the glycidyl esters of succinic acid, adipic acid, azelaic acid, sebacic acid, phthalic acid, terephthalic acid, tetra- and hexa-hydrophthalic acid, isophthalic acid or trimellitic acid, or of dimerised fatty acids.

Examples of polyepoxides that are not glycidyl compounds are the epoxides of vinylcyclohexane and dicyclopentadiene, 3-(3',4'-epoxycyclohexyl)-8,9-epoxy-2,4-dioxaspiro-[5.5]undecane, the 3',4'-epoxycyclohexylmethyl esters of 3,4-epoxycyclohexane-carboxylic acid, (3,4-epoxycyclohexyl-methyl 3,4-epoxycyclohexanecarboxylate), butadiene diepoxide or isoprene diepoxide, epoxidised linoleic acid derivatives or epoxidised polybutadiene.

Further suitable epoxy compounds are, for example, limonene monoxide, epoxidised soybean oil, bisphenol-A and bisphenol-F epoxy resins, such as, for example, Araldit GY 250 (A), ARALDIT GY 282 (F), ARALDIT GY 285 (F)), and photocurable siloxanes that contain epoxy groups.

A suitable component (a5) that when catalysed by an acid undergoes a crosslinking reaction or a polymerization with itself and/or with other components includes, for example, an epoxidized bisphenol A formaldehyde novolak resin and an epoxidized tetrabromo bisphenol A formaldehyde novolak resin. The preferred epoxy resin contains an average of eight epoxy groups, consisting of the glycidyl ether of the novolak condensation product of bisphenol A and formaldehyde, with an average molecular weight of about 1400 gram/mole, with an epoxy equivalent weight of about 215 gram/mole. Such a resin is, for example, commercially available from Shell Chemical under the trade name EPON® Resin SU-8.

Further suitable cationically polymerisable or crosslinkable components (a5) can be found, for example, also in U.S. Pat. No. 3,117,099, U.S. Pat. No. 4,299,938 and U.S. Pat. No. 4,339,567.

From the group of aliphatic epoxides there are suitable especially the monofunctional symbol α-olefin epoxides having an unbranched chain consisting of 10, 12, 14 or 16 carbon atoms.

Because nowadays a large number of different epoxy compounds are commercially available, the properties of the binder can vary widely. One possible variation, for example depending upon the intended use of the composition, is the use of mixtures of different epoxy compounds and the addition of flexibilisers and reactive diluents.

The epoxy resins can be diluted with a solvent to facilitate application, for example when application is effected by spraying, but the epoxy compound is preferably used in the solvent-less state. Resins that are viscous to solid at room temperature can be applied hot.

Oxime sulfonate derivatives can also be used as acid generators, which can be activated photochemically, for the acid-catalysed crosslinking of, for example, poly(glycidyl) methacrylates in negative tone systems. Such crosslinking reactions are described, for example, by Chae et al. in Pollimo 1993, 17(3), 292.

Examples of hydroxy-containing compounds include polyester polyols, such as, for example, polycaprolactones or polyester adipate polyols, glycols and polyether polyols, castor oil, hydroxy-functional vinyl and acrylic resins, cellulose esters, such as cellulose acetate butyrate, and phenoxy resins.

Further cationically curable formulations can be found, for example, in EP119425.

As component (a5), preference is given to cycloaliphatic epoxides, or epoxides based on bisphenol A.

Also suitable as component (a5) are all customary vinyl ethers, such as aromatic, aliphatic or cycloaliphatic vinyl ethers and also silicon-containing vinyl ethers. These are compounds having at least one, preferably at least two, vinyl ether groups in the molecule. Examples of vinyl ethers suitable for use in the compositions according to the invention include triethylene glycol divinyl ether, 1,4-cyclohexanedimethanol divinyl ether, 4-hydroxybutyl vinyl ether, the propenyl ether of propylene carbonate, dodecyl vinyl ether, tert-butyl vinyl ether, tert-amyl vinyl ether, cyclohexyl vinyl ether, 2-ethylhexyl vinyl ether, ethylene glycol monovinyl ether, butanediol monovinyl ether, hexanediol monovinyl ether, 1,4-cyclohexanedimethanol monovinyl ether, diethylene glycol monovinyl ether, ethylene glycol divinyl ether, ethylene glycol butylvinyl ether, butane-1,4-diol divinyl ether, hexanediol divinyl ether, diethylene glycol divinyl ether, triethylene glycol divinyl ether, triethylene glycol methylvinyl ether, tetra-ethylene glycol divinyl ether, pluriol-E-200 divinyl ether, polytetrahydrofuran divinyl ether-290, trimethylolpropane trivinyl ether, dipropylene glycol divinyl ether, octadecyl vinyl ether, (4-cyclohexyl-methyleneoxyethene)-glutaric acid methyl ester and (4-butoxyethene)-isophthalic acid ester.

The vinyl ether, acetal and/or alkoxysilane compounds used as part of component (a5) preferably contain at least two vinyl ether, acetal and/or alkoxysilane groups and have a molecular weight of 150 or more. Those vinyl ether, acetal and/or alkoxysilane compounds can be obtained, for example, by the reaction of a commercially available vinyl ether, acetal and/or alkoxysilane compound containing a vinyl ether, acetal and/or alkoxysilane group and in addition a maximum of one functional amino, epoxy, thiol, isocyanate, acrylic, hydride or hydroxyl group, with a compound having at least two groups capable of reacting with an amino, epoxy, thiol, isocyanate, acrylic, hydride or hydroxyl group. As examples thereof there may be mentioned compounds having at least two epoxy, isocyanate, hydroxyl and/or ester groups or compounds having at least two ethylenically or ethynylenically unsaturated groups.

As component (a5), preference is given to a composition in which the vinyl ether, acetal and/or alkoxysilane compounds are covalently bonded to the alkyd resin by addition via a reactive group such as an amino, hydroxyl, thiol, hydride, epoxy and/or isocyanate group. For that purpose, the compounds must have at least one group capable of forming an adduct with the reactive groups present in the alkyd resin.

To incorporate vinyl ether groups into the alkyd resin, use is made of a vinyloxyalkyl compound, the alkyl group of which is substituted by a reactive group, such as a hydroxyl, amino, epoxy or isocyanate group, that is capable of forming an adduct with one or more of the reactive groups present in the alkyd resin.

The oxime sulfonate compounds of formula (I) and (IA) can also be used, for example, as photo-activatable hardeners for siloxane-group-containing resins. Those resins can, for example, either undergo self-condensation by way of acid-catalysed hydrolysis or can be crosslinked with a second resin component, such as, for example, a polyfunctional alcohol, a hydroxygroup-containing acrylic or polyester resin, a partially hydrolysed polyvinylacetal or a polyvinyl alcohol. That type of polycondensation of polysiloxanes is described, for example, in J. J. Lebrun, H. Pode, Comprehensive Polymer Science Vol. 5, page 593, Pergamon Press, Oxford, 1989.

Especially preferred as acid-curable resins (a5) are amino resins, such as non-etherified or etherified melamine, urea, guanidine or biuret resins, especially methylated melamine resins or butylated melamine resins, corresponding glycolurils and urones. By "resins" in this context, there are to be understood both customary technical mixtures, which generally also comprise oligomers, and pure and high purity compounds. N-hexa(methoxymethyl) melamine and tetramethoxymethyl glucoril and N,N'-dimethoxymethylurone are the acid-curable resins given the greatest preference. The crosslinker components should generally be present in a concentration of from 2 to 40, preferably from 5 to 30, percent by weight, based on the total solids content of the negative composition.

The concentration of the compound of formula (I) and (IA) in negative compositions in general is from 0.1 to 30, preferably up to 20, percent by weight, based on the total solids content of the compositions. From 1 to 15 percent by weight is especially preferred.

Where appropriate, the negative compositions may comprise a film-forming polymeric binder (a4). This binder is preferably an alkali-soluble phenolic resin. Well suited for this purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$-$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl)propane. Also suitable are homo- and copolymers based on ethylenically unsaturated phenols, for example homopolymers of vinyl- and 1-propenyl-substituted phenols, such as p-vinylphenol or p-(1-propenyl)phenol or copolymers of these phenols with one or more ethylenically unsaturated materials, for example styrenes. The amount of binder should generally be from 30 to 95 percent by weight or, preferably, from 40 to 80 percent by weight.

Suitable formulations and the preparation of suitable polymer/copolymers for the negative compositions using the compounds of the formula I according to the present invention are for example published in JP2003-43688A, JP2003-114531A, JP2002-287359A, JP2001-255656A, JP2001-305727A, JP2003-233185A, JP2003-186195A, U.S. Pat. No. 6,576,394.

The chemically amplified negative, solvent-developable photosensitive resin compositions request the use of a specific component that when catalysed by an acid undergoes a crosslinking reaction or a polymerization with itself and/or with other components in the formulation. Suitable formulations are for example published in U.S. Pat. No. 4,882,245, U.S. Pat. No. 5,026,624, U.S. Pat. No. 6,391,523. Binders (a6) may also be added to the compositions according to the invention, this being especially advantageous when the photopolymerisable compounds are liquid or viscous substances. The amount of binder may be, for example, from 5 to 95% by weight, preferably from 10 to 90% by weight and especially from 40 to 90% by weight, based on total solids. The binder will be selected according to the field of use and the properties required therefor, such as developability in aqueous and organic solvent systems, adhesion to substrates and sensitivity to oxygen.

Various kinds of polymers can be used as the binder resin (a6) in the chemically amplified negative solvent-developable photosensitive resin compositions. Suitable examples include a phenoxy polyol resin which is a condensation product between epichlorohydrin and bisphenol A. A resin of this type is, for example, sold by Union Carbide Corporation under the Trade Mark PKHC.

Suitable binders are, for example, polymers having a molecular weight of approximately from 2000 to 2 000 000, preferably from 5000 to 1 000 000. Examples thereof are: homo- and co-polymers of acrylates and methacrylates, for example copolymers of methyl meth-acrylate/ethyl acrylate/methacrylic acid, poly(methacrylic acid alkyl esters), poly(acrylic acid alkyl esters); phenolic resins, cellulose derivatives, such as cellulose esters and ethers, for example cellulose acetate, cellulose acetate butyrate, methyl cellulose, ethyl cellulose; polyvinyl butyral, polyvinylformal, polyolefins, cyclised rubber, polyethers, such as poly-ethylene oxide, polypropylene oxide, polytetrahydrofuran; polystyrene, polycarbonate, poly-urethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), polyesters such as poly(ethylene glycol terephthalate) and poly(hexamethylene glycol succinate); and polyamides.

The positive and the negative compositions may comprise in addition to the photosensitive acid donor compound of formula (I) and (IA), further photosensitive acid donor compounds (b1), further additives (c), other photoinitiators (d), and/or sensitizers (e). Therefore, subject of the invention also are chemically amplified photosensitive resin compositions as described above, in addition to components (a) and (b), or components (a1), (a2), (a3) and (b), or components (a4), (a5) and (b) comprising further additives (c), further photosensitive acid donor compounds (b1), other photoinitiators (d), and/or sensitizers (e).

Oxime sulfonate derivatives of the present invention in the positive and negative photoseincitive resin compositions can also be used together with other, known photolatent acids (b1), for example, onium salts, 6-nitrobenzylsulfonates, bis-sulfonyl diazomethane compounds, cyano group-containing oxime sulfonate compounds, etc. Examples of known photolatent acids for chemically amplified photoseisitive resin compositions are described in U.S. Pat. No. 5,731,364, U.S. Pat. No. 5,800,964, EP704762, U.S. Pat. No. 5,468,589, U.S. Pat. No. 5,558,971, U.S. Pat. No. 5,558,976, U.S. Pat. No. 6,004,724, GB2348644 and particularly in EP794457 and EP795786.

If a mixture of photolatent acids is used in the compositions according to the invention, the weight ratio of oxime sulfonate derivatives of formula (I) or (IA) to the other photolatent acid (b1) in the mixture is preferably from 1:99 to 99:1.

Examples of photolatent acids which are suitable to be used in admixture with the compounds of formula (I) or (IA) are (1) onium salt compounds, for example, iodonium salts, sulfonium salts, phosphonium salts, diazonium salts, pyridinium salts. Preferred are diphenyliodonium triflate, diphenyliodonium pyrenesulfonate, diphenyliodonium dodecylbenzenesulfonate, triphenylsulfonium triflate, triphenylsulfonium hexafluoroantimonate, diphenyliodonium hexafluoroantimonate, triphenylsulfonium naphthalenesulfonate, (hydroxyphenyl)benzylmethylsulfonium toluenesulfonate, bis(4-tertbutylphenyl)iodonium bis(nonafluorobutanesulfonyl)imide, bis(4-tert-butylphenyl) iodonium tris(trifluoromethanesulfonyl)methide, triphenylsulfonium bis(trifluoromethanesulfonyl)imide, triphenylsulfonium (octafluorobutane-1,4-disulfonyl)imide, triphenylsulfonium tris(trifluoromethanesulfonyl)methide, tert-butyldiphenylsulfonium tris(trifluoromethanesulfonyl) methide, triphenylsulfonium 1,3-disulfonylhexafluoropropyleneimide, triarylsulfonium tetrakis-(pentafluorophenyl) borates, e.g. triphenylsulfonium tetrakis(pentafluorophenyl) borate, diaryliodonium tetrakis(pentafluorophenyl)borates, e.g. diphenyl tetrakis(pentafluorophenyl) borate, diphenyl [4-(phenylthio)phenyl]sulfonium trifluorotris(pentafluoroethyl)phosphate and the like; the iodonium cation may also be 4-methylphenyl-4'-isobutylphenyliodonium or 4-methylphenyl-4'-isopropylphenyliodonium. Particularly preferred are triphenylsulfonium triflate, diphenyliodonium hexafluoroantimonate. Other examples are described in JP2002-229192A, JP2003-140332A, JP2002-128755A, JP2003-35948A, JP2003-149800A, JP2002-6480A, JP2002-116546A, JP2002-156750A, U.S. Pat. No. 6,458,506, US2003/27061, U.S. Pat. No. 5,554,664, WO2007-118794.

(2) halogen-containing compounds haloalkyl group-containing heterocyclic compounds, haloalkyl group-containing hydrocarbon compounds and the like. Preferred are (trichloromethyl)-s-triazine derivatives such as phenyl-bis(trichloromethyl)-s-triazine, methoxyphenyl-bis(trichloromethyl)-s-triazine, naphthyl-bis(trichloromethyl)-s-triazine and the like; 1,1-bis(4-chlorophnyl)2,2,2-trichloroethane; and the like.

(3) sulfone compounds, for example of the formula $$R_a—S(=O)_2—C(=N_2)—S(=O)_2—R_b,$$

wherein $R_a$ and $R_b$ independently of one another are alkyl, cycloalkyl or aryl, each of which may have at least one substituent, e.g.

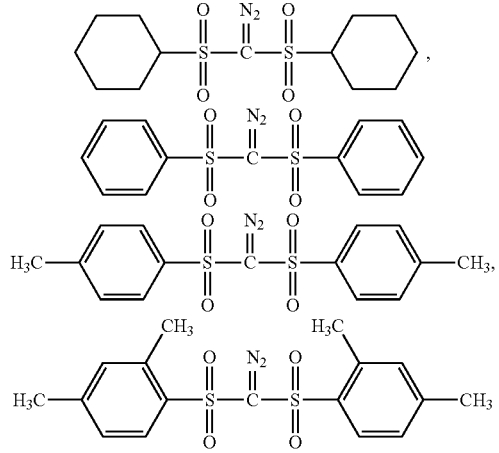

closed for example in US2002/0172886A, JP2003-192665A, US2002/9663A. More examples are β-ketosulfones, β-sulfonylsulfones and their α-diazo derivatives and the like. Preferred are phenacylphenylsulfone, mesitylphenacylsulfone, bis(phenylsulfonyl)methane, bis(phenylsulfonyl)diazomethane.

(4) sulfonate compounds, for example alkylsulfonic acid esters, haloalkylsulfonic acid esters, arylsulfonic acid esters, iminosulfonates, imidosulfonates and the like. Preferred imidosulfonate compounds are, for example, N-(trifluoromethlsulfonyloxy)succinimide, N-(trifluoromethylsulfonyloxy)phthalimide, N-(trifluoromethylsulfonyloxy)naphthylimide, N-(trifluoromethylsulfonyloxy) diphenylmaleimide, N-(trifluoromethylsulfonyloxy)-bicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-bicyclo-[2,2,1]-heptan-5,6-oxy-2,3-dicarboximide, N(camphanylsulfonyloxy) succinimide, N-(camphanylsulfonyloxy)phthalimide, N-(camphanylsulfonyloxy)naphthylimide, N-(camphanylsulfonyloxy)diphenylmaleimide, N(camphanylsulfonyloxy)-bicyclo-[2,2,1]-hept-5-ene-2,3dicarboximide, N-(camphenylsulfonyloxy)-7-oxabicyclo-[2,2,1]-hept-5-ene-2,3-dicarboximide, N-(camphanylsulfonyloxy)-7-oxabicyclo-[2,2,1]hept-5-ene-2,3-dicarboximide, N-(camphanylsulfonyloxy)-bicyclo-[2,2,1]-heptan-5,6-oxy-2,3-dicarboximide, N-(4-methylphenylsulfonyloxy)succinimide, N-(4-methylphenylsulfonyloxy)phthalimide, N-(4-methylphenylsulfonyloxy)naphthylimide, N-(4-methylphenylsulfonyloxy)naphthylimide, N-(4-methylphenylsulfonlyoxy)diphenylmaleimide, N-(4-methylphenylsulfonyloxy)-bicyclo-[2,2,1]-hept-5-ene2,3-dicarboximide, N-(4-methylphenylsulfonyloxy)-7-oxabicyclo-[2,2, 1]-hept-5-ene-2,3-dicarboximide, N-(4-methylphenylsulfonyloxy)-bicyclo-[2,2,1]-heptan-5,6-oxy-2,3-dicarboximide, N-(2-trifluoromethylphenylsulfonyloxy) succinimide, N-(2-trifluoromethylphenylsulfonyloxy) naphthylimide, N-(2-trifluoromethylphenylsulfonyloxy) diphenylmaleimide, N-(2-trifluoromethylphenylsulfonyloxy)-bicyclo-[2,2,1]-hept-5-ene-2,3-dicarboximide, N(2- trifluoromethylphenylsulfonyloxy)-7-oxabicyclo-[2,2,1]-hept-5-ene-2,3-dicarboximide, N-(2-trifluoromethylphenylsulfonyloxy)-bicyclo-[2,2,1]-heptan-5,6-oxy-2,3-dicarboximide and the like.

Other suitable sulfonate compounds preferably are, for example, benzoin tosylate, pyrogallol tristriflate, pyrogallolomethanesulfonic acid triester, nitorobenzyl-9,10-diethyloxyanthracene2-sulfonate, α-(4-toluene-sulfonyloxyimino)-benzyl cyanide, α-(4-toluene-sulfonyloxyiimino)-4-methoxybenzyl cyanide, α-(4-toluene-sulfonyloxyimino)-2-thienylmethyl cyanide, α-(methanesulfonyloxyimino)-1-cyclohexenylacetonitrile, α-(butylsulfonyloxyimino)-1-cyclopentenylacetonitrile, (4-methylsulfonyloxyimino-cyclohexa-2,5-dienylidene)-phenylacetonitrile, (5-methylsulfonyloxyimino-5H-thiophen-2-ylidene)-phenylacetonitrile, (5-methylsulfonyloxyimino-5H-thiophen-2-ylidene)-(2-methylphenyl)-acetonitrile, (5-propylsulfonyloxyimino5H-thiophen-2-ylidene)-(2-methylphenyl)acetonitrile, (5-(p-toluenesulfonyloxyimino)-5H-thiophen-2-ylidene)-(2-methylphenyl)acetonitrile, (5-(10-camphorsulfonyloxyimino)-5H-thiophen2-ylidene)-(2-methylphenyl)acetonitrile, (5-methylsulfonyloxyimino-5H-thiophen-2-ylidene)(2-chlorophenyl)-acetonitrile, 2,2,2-trifluoro-1-{4-(3-[4-{2,2,2-trifluoro-1-(1-propanesulfonyloxyimino)-ethyl}-phenoxy]-propoxy)-phenyl}-ethanone oxime 1-propanesulfonate, 2,2,2-trifluoro-1-{4-(3-[4-{2,2,2-trifluoro-1-(1-p-toluenesulfonyloxyimino)-ethyl}-phenoxy]-propoxy)-phenyl}-ethanone oxime 1-p-toluenesulfonate, 2-[2,2,3,3,4,4,5,5,6,6,7,7-dodecafluoro-1-(nonafluorobutylsulfonyloxyimino)-heptyl]-fluorene, 2-[2,2,3,3,4,4,4-heptafluoro-1-(nonafluorobutylsulfonyloxyimino)-butyl]-fluorene, 2-[2,2,3,3,4,4,5,5-octafluoro-1-(nonafluorobutylsulfonyloxyimino)-pentyl]-fluorene, 8-[2,2,3,3,4,4,5,5-octafluoro-1-(nonafluorobutylsulfonyloxyimino)-pentyl]-fluoranthene and the like.

In the radiation sensitive resin composition of this invention, particularly preferred sulfonate compounds include pyrogallolmethanesulfonic acid triester, N-(trifluoromethylsulfonyloxy)bicyclo-[2,2,1]-hept-5-ene-2,3-dicarboximide, N-(camphanylsulfonyloxy)naphthylimide, N-(2-trifluoromethylphenylsulfonyloxy)phthalimide, N-(trifluoromethylsulfonyloxy)-bicyclo-[2,2,1]hept-5-ene-2,3-dicarboximide, N-(camphanylsulfonyloxy)naphthylimide, N-(2-trifluoromethylphenylsulfonyloxy)phthalimide and the like.

(5) Quinonediazide compounds, for example 1,2-quinonediazidesulfonic acid ester compounds of polyhydroxy compounds. Preferred are compounds having a 1,2-quinonediazidesulfonyl group, e.g. a 1,2-benzoquinonediazide-4-sulfonyl group, a 1,2-naphthoquinonediazide-4-sulfonyl group, a 1,2-naphthoquinonediazide-5-sulfonyl group, a 1,2-naphthoquinonediazide-6-sulfonyl group or the like. Particularly preferred are compounds having a 1,2-naphthoquinonediazide-4-sulfonyl group or a 1,2-naphthoquinonediazide-5-sulfonyl group.

In particular suitable are 1,2-quinonediazidesulfonic acid esters of (poly)hydroxyphenyl aryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 2,3,4,4'-tetrahydroxybenzophenone, 2,2',4,4'tetrahydroxybenzophenone 2,2',3,4,4'-pentahydroxybenzophenone, 2,2'3,2,6'-pentahydroxybenzophenone, 2,3,3',4,4'5'-hexahydroxybenzophenone, 2,3',4,4',5'6-hexahydroxybenzophenone and the like; 1,2-quinonediazidesulfonic acid esters of bis-[(poly)hydroxylphenyl]alkanes such as bis(4-hydroxyphenyl)ethane, bis(2,4-dihydroxyphenyl)ethane, 2,2-bis(4-hydroxyphenyl)propane, 2,2-bis(2,4-dihydroxyphenyl)propane, 2,2-bis(2,3,4-trihydroxyphenyl)propane and the like; 1,2-quinonediazidesulfonic acid esters of (poly)hydroxyphenylalkanes such as 4,4'-dihydroxytriphenylmethane, 4,4'4"-trihydroxytriphenylmethane, 4,4'5,5'-tetramethyl-2,2'2"-trihydroxytriphenylmethane, 2,2,5,5'-tetramethyl4,4',4"-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]phenyl)ethane and the like; 1,2-quinonediazidesulfonic acid esters of (poly)hydroxylphenylflavans such as 2,4,4-trimethyl-2',4',7-trihydroxy-2-phenylflavan, 2,4,4-trimethyl-2',4',5',6,7-pentahydroxy-2-phenylflavan and the like.

Other examples of photolatent acids which are suitable to be used in admixture with the compounds according to the present invention are described in JP2003-43678A, JP2003-5372A, JP2003-43677A, JP2002-357904A, JP2002-229192A.

The positive and negative photosensitive resin composition of the present invention may optionally contain one or more additives (c) customarily used in the compositions in the customary amounts known to a person skilled in the art, for example, dyes, pigments, plasticizers, surfactants, flow improvers, wetting agents, adhesion promoters, thixotropic agents, colourants, fillers, solubility accelerators, acid-amplifier, photosensitizers and organic basic compounds.

Further examples for organic basic compounds which can be used in the composition of the present invention are compounds which are stronger bases than phenol, in particular, nitrogen-containing basic compounds. These compounds may be ionic, like, for example, tetraalkylammonium salts or non-ionic. Preferred organic basic compounds are nitrogen-containing basic compounds having, per molecule, two or more nitrogen atoms having different chemical environments. Especially preferred are compounds containing both at least one substituted or unsubstituted amino group and at least one nitrogen-containing ring structure, and compounds having at least one alkylamino group. Examples of such preferred compounds include guanidine, aminopyridine, amino alkylpyridines, aminopyrrolidine, indazole, imidazole, pyrazole, pyrazine, pyrimidine, purine, imidazoline, pyrazoline, piperazine, aminomorpholine, and aminoalkylmorpholines. Suitable are both, the unsubstituted compounds or substituted derivatives thereof. Preferred substituents include amino, aminoalkyl groups, alkylamino groups, aminoaryl groups, arylamino groups, alkyl groups, alkoxy groups, acyl groups acyloxy groups aryl groups, aryloxy groups, nitro, hydroxy, and cyano. Specific examples of especially preferred organic basic compounds include guanidine, 1,1-dimethylguanidine, 1,1,3,3-tetramethylguanidine, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoehtylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-imimopiperidine, 1-(2-aminoethyl)pyrrolidine, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine, and N-(2-aminoethyl)morpholine.

Other examples of suitable organic basic compounds are described in DE4408318, U.S. Pat. No. 5,609,989, U.S. Pat. No. 5,556,734, EP762207, DE4306069, EP611998, EP813113, EP611998, and U.S. Pat. No. 5,498,506, JP2003-43677A, JP2003-43678A, JP2002-226470A, JP2002-363146A, JP2002-363148A, JP2002-363152A, JP2003-98672A, JP2003-122013A, JP2002-341522A. However, the organic basic compounds suitable in the present invention are not limited to these examples.

The nitrogen-containing basic compounds may be used alone or in combination of two or more thereof. The added amount of the nitrogen-containing basic compounds is usually from 0.001 to 10 parts by weight, preferably from 0.01 to 5 parts by weight, per 100 parts by weight of the photosensitive resin composition (excluding the solvent). If the amount thereof is smaller than 0.001 part by weight, the effects of the present invention cannot be obtained. On the other hand, if it exceeds 10 parts by weight, reduced sensitivity and impaired developability at unexposed parts are liable to be caused.

The composition can further contain a basic organic compound which decomposes under actinic radiation ("suicide base") such as for example described in EP710885, U.S. Pat. No. 5,663,035, U.S. Pat. No. 5,595,855, U.S. Pat. No. 5,525,453 and EP611998.

(Spectral) sensitizers (e) may be further added to sensitize the photo latent acid to exhibit absorption in a region of longer wavelengths than far ultaviolet, whereby the photosensitive composition of the present invention can, for example, be rendered sensitive to an i-line or g-line radiation. Examples of suitable spectral sensitizers include benzophenones, p,p'-tetramethyldiaminobenzophenone, p,p'-tetraethylethylaminobenzophenone, thioxanthone, 2-chlorothioxanthone, anthrone, pyrene, perylene, phenothiazine, benzil, acridine orange, benzoflavin, cetoflavin T, 9,10-diphenylanthracene, 9-fluorenone, acetophenone, phenanthrene, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butylanthraquinone, 1,2-benzanthraquinone, 3-methyl-1,3-diaza-1,9-benzanthrone, dibenzalacetone, 1,2-naphthoquinone, 3-acylcoumarin derivatives, 3,3'-carbonyl-bis(5,7-dimethoxycarbonylcoumarin), 3-(aroylmethylene) thiazolines, eosin, rhodamine, erythrosine, and coronene. However, the suitable spectral sensitizers are not limited to these examples.

These spectral sensitizers can be used also as light absorbers for absorbing the far ultraviolet emitted by a light source. In this case, the light absorber reduces light reflection from the substrate and lessens the influence of multiple reflection within the coated film, thereby diminishing the effect of standing waves.

Specific examples of such compounds are

1. Thioxanthones

Thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfuryl-thioxanthone, 3,4-di-[2-(2-methoxyethoxy)ethoxycarbonyl]-thioxanthone, 1,3-dimethyl-2-hydroxy-9H-thioxanthen-9-one 2-ethylhexylether, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)benzophenone, 4,4'-bis(diethylamino)benzophenone, 4,4'-bis(methylethylamino)benzophenone, 4,4'-bis(p-isopropylphenoxy)benzophenone, 4-methyl benzophenone, 2,4,6-trimethylbenzophenone, 3-methyl-4'-phenyl-benzophenone, 2,4,6-trimethyl-4'-phenyl-benzophenone, 4-(4-methylthiophenyl)-benzophenone, 3,3'-dimethyl-4-methoxy benzophenone, methyl-2-benzoylbenzoate, 4-(2-hydroxyethylthio)benzophenone, 4-(4-tolylthio)benzophenone, 1-[4-(4-benzoyl-phenylsulfanyl)-phenyl]-2-methyl-2-(toluene-4-sulfonyl)-propan-1-one, 4-benzoyl-N,N,N-trimethyl-benzenemethanaminium chloride, 2-hydroxy-3-(4-benzoylphenoxy)-N,N,N-trimethyl-1-propanaminium chloride monohydrate, 4-(13-acryloyl-1,4,7,10,13pentaoxatridecyl)-benzophenone, 4-benzoyl-N,N-dimethyl-N-[2-(1-oxo-2-propenyl)oxy]ethyl-benzenemethanaminium chloride;

3. Coumarins

Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)-coumarin], 3,3'-carbonyl-bis(7-methoxycoumarin), 3,3'-carbonyl-bis(7-diethylamino-coumarin), 3-isobutyroylcoumarin, 3-benzoyl-5,7-dimethoxycoumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP09-179299A and JP09-325209A, for example 7-[{4-chloro-6-(diethylamino)-S-triazine-2-yl}amino]3-phenylcoumarin;

4. 3-(aroylmethylene)-thiazolines 3-methyl-2-benzoylmethylene-β-naphthothiazoline, 3-methyl-2-benzoylmethylene-benzothiazoline, 3-ethyl-2-propionylmethylene-β-naphthothiazoline;

5. Rhodanines 4-dimethylaminobenzalrhodanine, 4-diethylaminobenzalrhodanine, 3-ethyl-5-(3-octyl-2-benzothiazolinylidene)-rhodanine, the rhodanine derivatives, formulae [1], [2], [7], disclosed in JP08-305019A;

6. Other Compounds acetophenone, 3-methoxyacetophenone, 4-phenylacetophenone, benzil, 4,4'-bis(dimethylamino)benzil, 2-acetylnaphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thiomichler's ketone, α-(4-dimethylaminobenzylidene) ketones, e.g. 2,5-bis(4-diethylaminobenzylidene)cyclopentanone, 2-(4-dimethylamino-benzylidene)-indan-1-one, 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)phthalimide, phenothiazine, methylphenothiazine, amines, e.g. N-phenylglycine, ethyl 4-dimethylaminobenzoate, butoxyethyl 4-dimethylaminobenzoate, 4-dimethylaminoacetophenone, triethanolamine, methyldiethanolamine, dimethylaminoethanol, 2-(dimethylamino)ethyl benzoate, poly(propylenegylcol)-4-(dimethylamino) benzoate, pyrromethenes, e.g., 1,3,5,7,9-pentamethyl pyrromethene $BF_2$ complex, 2,8-diethyl-1,3,5,7,9-pentamethyl pyrromethene $BF_2$ complex, 2,8-diethyl-5-phenyl-1,3,7,9-tetramethyl pyrromethene $BF_2$ complex, 9,10-bis(phenylethynyl)-1,8-dimethoxyanthracene, benzo[1,2,3-kl:4,5,6-k'l]dixanthene.

Further suitable additives (c) are "acid-amplifiers", compounds that accelerate the acid formation or enhance the acid concentration. Such compounds may also be used in combination with the oxime sulfonate derivatives of the formula (I) or (IA) according to the invention in positive or negative compositions, or in imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

If desired, the composition according to the invention can also contain free-radically polymerisable components, such as ethylenically unsaturated monomers, oligomers or polymers. These radically polymerizable components may be added to the component (a). Said radically curable components may, however, also be part of (a1), (a2), (a3), (a4), (a5) or (a6). Suitable materials contain at least one ethylenically unsaturated double bond and are capable of undergoing addition polymerization.

Examples of suitable monomers that contain an ethylenic double bond include alkyl and hydroxyalkyl acrylates and methacrylates, such as methyl, ethyl, propyl, isopropyl, butyl, hexyl, 2-ethylhexyl and 2-hydroxyethyl (meth)acrylate, stearyl acrylate and isobornyl acrylates. Further suitable examples include acrylonitrile, acrylamide, methacrylamide, N-substituted (meth)acrylamides, vinyl esters, such as vinyl acetate, vinyl ethers, such as isobutylvinyl ether, styrene, alkyl- and halo-substituted styrene, N-vinylpyrrolidone, vinyl chloride and vinylidene chloride.

Examples of suitable monomers that contain at least two double bonds include glycerol diacrylates, glycerol triacrylates, ethylene glycol diacrylates, diethylene glycol diacrylates, diethylene glycol dimethacrylate, triethylene glycol dimethacrylates, 1,3-propanediol di-acrylate, 1,3-propanediol dimethacrylate, neopentyl glycol diacrylates, hexamethylene glycol diacrylate, bisphenol-A diacrylates, 4,4'-bis(2-acryloyloxyethoxy)diphenylpropane, penta-erythritol triacrylate or tetraacrylate, pentaerythritol tetramethacrylate, trimethylolpropane triacrylate, 1,2,4-butanetriol trimethacrylate, 1,4-cyclohexanediol diacrylate, sorbitol hexa-acrylate, bis[1-(2-acryloxy)]-p-ethoxyphenyldimethylmethane, bis[1-(3-acryloxy-2-hydroxy)]-p-propoxyphenyldimethylmethane and trishydroxyethyl isocyanurate trimethacrylate; the bis-acrylates and bismethacrylates of poly(ethylene glycol) having a molecular weight of from 200 to 500, diallyl phthalate, divinyl succinate, divinyl adipate and divinyl phthalate, vinyl acrylate, divinyl benzene, triallyl phosphate, triallyl isocyanurates and tris(2-acryloyl-ethyl) isocyanurate.

Examples of higher-molecular-weight (oligomeric) poly-unsaturated compounds include acrylated epoxy resins, acrylated or vinyl ether- or epoxy-group-containing polyesters, polyurethanes and polyethers. Further examples of unsaturated oligomers are unsaturated polyester resins, which are usually prepared from maleic acid, phthalic acid and one or more diols and have molecular weights of approximately from 500 to 3000. Vinyl ether monomers and oligomers, and maleate-terminated oligomers having polyester, poly-urethane, polyether, polyvinyl ether and epoxy main chains can also be used.

Also copolymers of vinyl ethers and monomers which are functionalised with maleic acid, as described in WO90/01512, are also very suitable. Also suitable, however, are copolymers of monomers functionalised with vinyl ether and maleic acid. Such unsaturated oligomers can also be referred to as pre-polymers.

Functionalised acrylates are also suitable. Examples of suitable monomers that are normally used to form the base polymer (the backbone) of the functionalised acrylate or methacrylate polymer are acrylate, methacrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, etc. In addition, suitable amounts of functional monomers are copolymerised during the polymerisation in order to obtain the functional polymers. Acid-functionalised acrylate or methacrylate polymers are obtained using acid-functional monomers, such as acrylic acid and methacrylic acid. Hydroxy-functional acrylate or methacrylate polymers are obtained from hydroxy-functional monomers, such as 2-hydroxyethyl methacrylate, 2-hydroxypropyl methacrylate and 3,4-dihydroxybutyl methacrylate. Epoxy-functionalised acrylate or methacrylate polymers are obtained using epoxy-functional monomers, such as glycidyl methacrylate, 2,3-epoxybutyl methacrylate, 3,4-epoxybutyl methacrylate, 2,3-epoxycyclohexyl methacrylate, 10,11-epoxyundecyl meth-acrylate, etc. It is also possible to obtain isocyanate-functional polymers from isocyanate-functionalised monomers, such as meta-isopropenyl-α,α-dimethylbenzyl isocyanate.

Especially suitable are, for example, esters of ethylenically unsaturated mono- or polyfunctional carboxylic acids and polyols or polyepoxides, and polymers having ethylenically unsaturated groups in the chain or in side groups, such as unsaturated polyesters, poly-amides and polyurethanes and copolymers thereof, alkyd resins, polybutadiene and buta-diene copolymers, polyisoprene and isoprene copolymers, polymers and copolymers having (meth)acrylic groups in side chains, and mixtures of one or more such polymers.

Examples of suitable mono- or poly-functional unsaturated carboxylic acids are acrylic acid, methacrylic acid, crotonic acid, itaconic acid, cinnamic acid, maleic acid and fumaric acid and unsaturated fatty acids, such as linolenic acid or oleic acid. Preference is given to acrylic acid and methacrylic acid.

Mixtures of saturated di- or poly-carboxylic acids with unsaturated carboxylic acids may, however, also be used. Examples of suitable saturated di- or poly-carboxylic acids include, for example, tetrachlorophthalic acid, tetrabromophthalic acid, phthalic acid anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid, etc.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)-propane, and novolaks and resoles. Examples of polyepoxides are those based on the polyols mentioned, especially the aromatic polyols and epichlorohydrin. Also suitable as polyols are polymers and copolymers containing hydroxyl groups in the polymer chain or in side groups, such as polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(P3-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to have been modified, for example etherified, or esterified by other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol di-acrylate, penta-erythritol triacrylate, pentaerythritol tetraacrylate, dipentaerythritol di-acrylate, dipenta-erythritol triacrylate, dipentaerythritol tetraacrylate, dipentaerythritol pentaacrylate, dipenta-erythritol hexaacrylate, tripentaerythritol octaacrylate, pentaerythritol dimethacrylate, penta-erythritol trimethacrylate, dipentaerythritol dimethacrylate, dipentaerythritol tetrameth-acrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Suitable unsaturated, free-radically polymerisable compounds are also the amides of the same or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetraamine and di(β-aminoethoxy)- or di(β-aminopropoxy)-ethane.

Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They can be used together with ethylenically unsaturated comonomers, for example styrene. The polyesters and polyamides can also be derived from dicarboxylic acids and ethylenically unsaturated diols or diamines, especially from those having longer chains of, for example, from 6 to 20 carbon atoms. Examples of polyurethanes are those composed of saturated or unsaturated diisocyanates and saturated or unsaturated diols.

Polybutadiene and polyisoprene and copolymers thereof are known. Suitable comonomers include, for example, olefins, such as ethylene, propene, butene, hexene, (meth)acrylates, acrylonitrile, styrene and vinyl chloride. Polymers having (meth)acrylate groups in the side chain are also known. They may be, for example, reaction products of novolak-based epoxy resins with (meth)acrylic acid; homo- or co-polymers of vinyl alcohol or hydroxyalkyl derivatives thereof that have been esterified with (meth)acrylic acid; or homo- and co-polymers of (meth)acrylates that have been esterified with hydroxyalkyl (meth)acrylates.

It is also possible to use compounds that can be cross-linked equally both free-radically and cationically. Such compounds contain, for example, both a vinyl group and a cycloaliphatic epoxy group. Examples thereof are described in JP2-289611A and U.S. Pat. No. 6,048,953.

Mixtures of two or more such free-radically polymerisable materials can also be used.

The formulations can also comprise dyes and/or white or coloured pigments as additional additives (c). Depending upon the intended use, it is possible to use both inorganic and organic pigments. Such additives are known to the person skilled in the art; some examples thereof are titanium dioxide pigments, for example of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and metal complexes thereof, phthalocyanine pigments, polycyclic pigments, such as, for example, perylene, anthraquinone, thioindigo, quinacridone and triphenylmethane pigments, and diketopyrrolo-pyrrole, isoindolinone, e.g. tetrachloro-isoindolinone, isoindoline, dioxazine, benzimidazolone and quinophthalone pigments.

The pigments can be used individually or in admixture in the formulations. Depending upon the intended use, the pigments are added to the formulations in amounts customary in the art, for example in an amount of from 1 to 60% by weight, or from 10 to 30% by weight, based on the total weight.

The formulations may, for example, also comprise organic dyes of a wide variety of classes. Examples thereof include azo dyes, methine dyes, anthraquinone dyes and metal complex dyes. Customary concentrations are, for example, from 0.1 to 20%, especially from 1 to 5%, based on the total weight.

The pigments, latent pigments or dyes or differently coloured precursors of such pigments and dyes that are added may be so selected that they undergo a colour change in the presence of the acid formed from the iodonium salt as a result of irradiation.

Such compositions then show, by the colour change, that they have been irradiated and can be used, for example, as irradiation dose indicators, e.g. for UV radiation, electron beams, X-rays, etc.

Examples of dyes as further additves (c) suitable for the compositions of the present invention are oil-soluble dyes and basic dyes, e.g. Oil Yellow #101, Oil Yellow #103, Oil Pink #312, Oil Green BG, Oil Blue BOS, Oil Blue #603, Oil Black BY, Oil Black BS, Oil Black T-505 (all manufactured by Orient Chemical Industries Ltd., Japan), crystal violet ($C_{142555}$), methyl violet (CI 42535), rhodamine B (CI 45170B), malachite green (CI 42000), and methylene blue ($C_{152015}$).

The adhesion aid for use as additives (c) in the present invention is a compound for enhancing adhesion of an insulating film to an inorganic material Working out to a substrate, for example, a silicon compound such as silicon, silicon oxide and silicon nitride, or a metal such as gold, copper and aluminum. Specific examples thereof include a silane coupling agent and a thiol-based compound.

The silane coupling agent as the adhesion aid for use in the present invention is intended to modify the interface and is not particularly limited, and a known silane coupling agent may be used.

Preferable examples of the silane coupling agent are γ-aminopropyltrimethoxysilane, γ-aminopropyltriethoxysilane, γ-glycidoxypropyltrialkoxysilane, γ-glycidoxypropylalkyldialkoxysilane, γ-methacryloxypropyltrialkoxysilane, γ-methacryloxypropylalkyldialkoxysilane, γ-chloropropyltrialkoxysilane, γ-mercaptopropyltrialkoxysilane, β-(3,4-epoxycyclohexyl)ethyltrialkoxysilane, and vinyltrialkoxysilane.

Among these, γ-glycidoxypropyltrialkoxysilane and methacryloxypropyltrialkoxysilane are more preferred.

One of these may be used alone, or two or more kinds thereof may be used in combination. These are effective not only for enhancing the adhesion to a substrate but also for adjusting the taper angle with the substrate.

Other additives (c) to improve the performance such as resolution, pattern profile, process latitude, line edge roughness, stability are for example described in JP2002-122992A, JP2002-303986A, JP2002-278071A, JP2003-57827A, JP2003-140348A, JP2002-6495A, JP2002-23374A, JP2002-90987A, JP2002-91004A, JP2002-131913A, JP2002-131916A, JP2002-214768A, JP2001-318464A, JP2001-330947A, JP2003-57815A, JP2003-280200A, JP2002-287362A, JP2001-343750A. Such compounds may also be used in combination with the oxime sulfonate derivatives of the formula (I) or (IA) according to the invention in positive or negative photosensitive resin compositions.

Usually, for the application to a substrate of the photosensitive composition of the present invention, the composition is dissolved in an appropriate solvent. Preferred examples of these solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monomethyl ether, propylene glycol monomethyl ether acetate, toluene, ethyl acetate, butyl acetate, methyl lactate, ethyl lactate, methyl methoxypropionate, ethyl ethoxypropionate, methyl pyruvate, ethyl pyruvate, propyl pyruvate, N, N-dimethylformamide, dimethyl sulfoxide, N-methylpyrrolidone, and tetrahydrofuran.

These solvents may be used alone or as mixtures. Preferred examples of the solvents are esters, such as 2-methoxyethyl acetate, ethylene glycolmonoethyl ether acetate, propylene glycol monomethyl ether acetate, methyl methoxypropionate, ethyl ethoxypropionate, and ethyl lactate. Use of such solvents is advantageous because the oxime sulfonate derivatives represented by formula (I) or (IA) according to the present invention have good compatibility therewith and better solubility therein.

A surfactant can be added to the solvent. Examples of suitable surfactants include nonionic surfactants, such as polyoxyethylene alkyl ethers, e.g. polyoxyethylene lauryl ether, polyoxyethylene stearyl ether, polyoxyethylene acetyl ether, and polyoxyethylene oleyl ether; polyoxyethylene alkylaryl ethers, e.g. polyoxyethylene, octylphenol ether and polyoxyethylene nonylphenol ether; polyoxyethylene/polyoxypropylene block copolymers, sorbitan/fatty acid esters, e.g. sorbitan monolaurate, sorbitan monopalmitate, sorbitan monostearate, sorbitan monooleate, sorbitan trioleate; fluorochemical surfactants such as F-top EF301, EF303, and EF352 (manufactured by New Akita Chemical Company, Japan). Megafac F171 and F17.3 (manufactured by Dainippon Ink & Chemicals, Inc, Japan), Fluorad FC 430 and FC431 (manufactured by Sumitomo 3M Ltd., Japan), Asahi Guard AG710 and Surflon S-382, SC101, SC102, SC103, SC104, SC105, and SC106 (manufactured by Asahi Grass Col, Ltd., Japan); organosiloxane polymer KP341 (manufactured by Shin-Etsu Chemical Co., Ltd., Japan); and acrylic or methacrylic (co)polymers Poly-flow Now.75 and NO.95 (manufactured by Kyoeisha Chemical Co., Ltd., Japan). Other examples are described in JP-A-2001-318459, JP-A2002-6483. The added amount of the surfactant usually is 2 parts by weight or lower, desirably 0.5 part by weight or lower, per 100 parts by weight of the solid components of the composition of the present invention. The surfactants may be added alone or in combination of two or more thereof.

The solution of the polymerizable composition comprising the compounds of the formula (I) or (IA) is uniformly applied to a substrate by means of known coating methods, for example by spin-coating, immersion, knife coating, curtain pouring techniques, brush application, spraying and roller coating. It is also possible to apply the photosensitive layer to a temporary, flexible support and then to coat the final substrate by coating transfer (laminating).

The amount applied (coating thickness) and the nature of the substrate (coating substrate) are dependent on the desired field of application. The range of coating thicknesses can in principle include values from approximately 0.01 μm to more than 100 μm.

After the coating operation generally the solvent is removed by heating, resulting in a layer of the photosensitive resin composition on the substrate. The drying temperature must of course be lower than the temperature at which certain components of the composition might react or decompose. In general, drying temperatures are in the range from 60 to 160° C.

The coating is then irradiated image-wise. The expression "image-wise irradiation" includes irradiation in a predetermined pattern using actinic radiation, i.e. both irradiation through a mask containing a predetermined pattern, for example a transparency, a chrome mask or a reticle, and irradiation using a laser beam or electron beam that writes directly onto the coated surface, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997, 107 pp. 275-281 and by K. P. Nicolay in Offset Printing 1997, 6, pp. 34-37.

After the irradiation and, if necessary, thermal treatment, the irradiated sites (in the case of positive photoseisitive resin compositions) or the non-irradiated sites (in the case of negative photoseisitive resin compositions) of the composition are removed in a manner known perse using a developer.

In order to accelerate the catalytic reaction and hence the development of a sufficient difference in solubility between the irradiated and unirradiated sections of the resist coating in the developer, the coating is preferably heated before being developed. The heating can also be carried out or begun during the irradiation. Temperatures of from 60 to 160° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under those processing conditions.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may, for example, be used for the development. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5 N, but are usually diluted in suitable manner before use. For example solutions having a normality of approximately 0.1-0.3 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of these solvents. A typical aqueous/organic developer system is based on Butylcellosolve®/water.

Especially in case of formulations including a component with a functional group for applications, such as insulating layers, interlayer dielectric films, passivation layers, planarization layers, protecting layers, overcoat layers, banks and so on, a pattern obtained after development process may be subjected to a thermal treatment using a hotplate or an oven at a preferable temperature from 130 to 270° C., more preferably at the temperature from 180 to 250° C. for the period from 3 to 120 min, more preferably from 5 to 90 min, to complete acid decomposition reaction resulting in generating carboxyl group and/or phenolic group and to crosslink the group with a functional group, e.g. glycidyl group. As a result, the obtained film or pattern with excellent heat resistance, hardness is formed. Additionally the thermal treatment under nitrogen atmosphere may give the film better transparency.

Subject of the invention also is a process for the preparation of a photoresist by (1) applying to a substrate a composition as described above;

(2) post apply baking the composition at temperatures between 60° C. and 140° C.;

(3) image-wise irradiating with light of wavelengths between 200 nm and 450 nm;

(4) optionally post exposure baking the composition at temperatures between 60° C. and 140° C.; and (5) developing with a solvent or with an aqueous alkaline developer;

(6) optionally flood exposing the coating with light of the wavelengths of between 200 nm and 450 nm;

(7) baking at a temperature between 90° C. and 250° C.

Preferred is a process as described above, wherein the image-wise irradiation is carried out with monochromatic or polychromatic radiation in the wavelength range from 10 to 600 nm, in particular in the range from 10 to 700 nm.

The photoresist compositions can be used on all substrates and with all exposure techniques known to the person skilled in the art. For example, semiconductor substrates can be used, such as silicon, gallium arsenide, germanium, indium antimonide; furthermore substrate covered by oxide or nitride layers, such as silicon dioxide, silicon nitride, titanium nitride, siloxanes, as well as metal substrates and metal coated substrates with metals such as aluminium, copper, tungsten, etc. The substrate can also be coated with polymeric materials, for example with organic antireflective coatings, insulation layers and dielectric coatings from polymeric materials prior to coating with the photoresist.

The photoresist layer can be exposed by all common techniques, such as direct writing, i.e. with a laser beam or projection lithography in step- and repeat mode or scanning mode, or by contact printing through a mask.

In case of projection lithography a wide range of optical conditions can be used such as coherent, partial coherent or incoherent irradiation. This includes off-axis illumination techniques, for example annular illumination and quadrupol illumination where the radiation is allowed to pass only certain regions of the lens, excluding the lens center.

The mask used to replicate the pattern can be a hard mask or a flexible mask. The mask can include transparent, semitransparent and opaque patterns. The pattern size can include also patterns which are at or below the resolution limit of the projection optics and placed on the mask in a certain way in order to modify the aerial image, intensity and phase modulation of the irradiation after having passed the mask. This includes phase shift masks and half-tone phase shift masks.

The patterning process of the photoresist composition can be used to generate patterns of any desired geometry and shape, for example dense and isolated lines, contact holes, trenches, dots, etc.

The photosensitive resin compositions according to the invention have excellent lithographic properties, in particular a high sensitivity, and high resist transparency for the imaging radiation.

Possible areas of use of the composition according to the invention are as follows: use as photosensitive resin compositions for electronics, such as etching resists, ionimplantation resist, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques, which are employed for various applications, for example, 3D optical information storage described in J. Photochem. Photobio. A, 158, 163 (2003), Chem. Mater. 14, 3656 (2002).

The composition according to the invention is also suitable for making inter-metal dielectrics layer, buffer layer, passivation coat of semiconductor devices and suitable for making waveguide for optoelectronics. For MEMS (micro electro mechanical systems) application, the composition according to the invention can be used as etching resist, mold for material deposition, and three dimensional objects of device itself. The coating substrates and processing conditions vary accordingly. Such example is described in U.S. Pat. No. 6,391,523.

The compounds of formula (I) and (IA) according to the present invention, in combination with a sensitizer compound as described above, can also be used in holographic data storage (HDS) systems as for example described in WO03/021358.

The compositions according to the invention include also adhesives, as used, for example, for adhesive bonding (DVD bonding) in the manufacture of digital versatile disks (DVD) and as described, for example, in: WO99/66506, WO99/63017, JP11-241055A, JP11-181391A, WO 98/31765, and also as radiation-curable laminating adhesives for flexible packaging (see, e.g., U.S. Pat. No. 5,328,940), optical adhesives (e.g. German Patent Application DD 225985) and pressure-sensitive adhesives (e.g. U.S. Pat. No. 4,988,741 and EP115870).

The compositions according to the invention are advantageously used where there is a need for hard coatings, adhesive bonds or photopolymerised dimensionally stable three-dimensional mouldings (e.g. for rapid prototyping) having good adhesion to paper, glass, metal, silicon, polycarbonate, acrylate polymers and other polymer substrates, and that exhibit only slight shrinkage during curing.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

The invention relates also to the use of compounds of formula (I) or (IA) as photolatent acid donors in compositions that can be crosslinked under the action of an acid and/or as dissolution enhancers in compositions wherein the solubility is increased under the action of an acid.

Subject of the invention further is a process of crosslinking compounds that can be crosslinked under the action of an acid, which method comprises adding a compound of formula (I) or (IA) to the above-mentioned compositions and irradiating imagewise or over the whole area with light having a wavelength of 10-1500 nm.

The invention relates also to the use of compounds of formula (I) or (IA) as photosensitive acid donors in the preparation of pigmented and non-pigmented surface coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, insulating layers, interlayer dielectric films, passivation layers, planarization layers, protecting layers, overcoat layers, banks, electroluminescence displays and liquid crystal displays (LCD), waveguides, optical switches, color proofing systems, resists, photoresists for electronics, electroplating resists, etch resists both for liquid and dry films, solder resist, photoresist materials for a UV and visible laser direct imaging system, photoresist materials for forming dielectric layers in a sequential build-up layer of a printed circuit board, image-recording materials, image-recording materials for recording holographic images, optical information storage or holographic data storage, decolorizing materials, decolorizing materials for image recording materials, image recording materials using microcapsules, magnetic recording materials, micromechanical parts, plating masks, etch masks, glass fibre cable coatings, microelectronic circuits;

especially to the use of compounds of the formula (I) or (IA) as photosensitive acid donors in the preparation of surface coatings, printing inks, printing plates, colour filters, resists or image-recording materials, or image-recording materials for recording holographic images;

in particular to the use of compounds of the formula (I) or (IA) as photosensitive acid donors in the preparation of spacers, insulating layers, interlayer dielectric films, planarization layers, protecting layers, overcoat layers, banks for electroluminescence displays and liquid crystal displays (LCD);

to the use of compounds of the formula (I) or (IA) as photosensitive acid donors in the preparation of photo resist formulations for display application, e.g. insulation layer, liquid crystal displays (LCD), organic light emitting diode (OLED).

Subject of the invention is also the use of compounds of formula (I) or (IA) as photosensitive acid donors in the preparation of colour filters or chemically amplified photoseisitive resin composition materials; as well as to a process for the preparation of colour filters or chemically amplified photosensitive resin compositions.

The invention further pertains to a color filter prepared by providing red, green and blue picture elements and optionally, a black matrix, all comprising a photosensitive resin and a pigment and/or dye on a transparent substrate and providing a transparent electrode either on the surface of the substrate or on the surface of the color filter layer, wherein said photosensitive resin comprises compounds of formula (I) or (IA) as photosensitive acid donors.

The person skilled in the art is aware of suitable pigments or dyes to provide the color elements, as well as the black matrix and corresponding suitable resins as shown in, for examples, JP9-203806A, JP10-282650A, JP10-333334A, JP11-194494A, JP10-203037A, JP2003-5371A.

As already mentioned above, in photocrosslinkable compositions, oxime sulfonate derivatives act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Oxime sulfonate derivatives according to the present invention can also be used to produce so-called "print-out" images when the compound is used together with a colourant that changes colour when the pH changes, as described e.g. in JP4-328552A or in U.S. Pat. No. 5,237,059. Such color-change systems can be used according to EP199672 also to monitor goods that are sensitive to heat or radiation.

In addition to a colour change, it is possible during the acid-catalysed deprotection of soluble pigment molecules (as described e.g. in EP648770, EP648817 and EP742255) for the pigment crystals to be precipitated; this can be used in the production of colour filters as described e.g. in EP654711 or print out images and indicator applications, when the colour of the latent pigment precursor differs from that of the precipitated pigment crystal.

Compositions using pH sensitive dyes or latent pigments in combination with oxime sulfonate derivatives can be used as indicators for electromagnetic radiation, such as gamma radiation, electron beams, UV- or visible light, or simple throw away dosimeters. Especially for light, that is invisible to the human eye, like UV- or IR-light, such dosimeters are of interest.

Finally, oxime sulfonate derivatives that are sparingly soluble in an aqueous-alkaline developer can be rendered soluble in the developer by means of light-induced conversion into the free acid, with the result that they can be used as solubility enhancers in combination with suitable film-forming resins.

Resins which can be crosslinked by acid catalysis and accordingly by the photolatent acids of formula (I) or (IA) according to the invention, are, for example, the ones as described above.

In coating applications the surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxygroup-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. Polysiloxanes can also be crosslinked using acid catalysis. These siloxane group-containing resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a poly-vinyl alcohol. This type of polycondensation of polysiloxanes is described, for example, in J. J. Lebrun, H. Pode, Comprehensive Polymer Science, Vol. 5, p. 593, Pergamon Press, Oxford, 1989. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-2H-pyran (dimeric acrolein) or the 3,4-dihydro-2H-pyran-2-carboxylic acid ester of 2-hydroxymethyl-3,4-dihydro-2H-pyran; vinyl esters, such as vinyl acetate and vinyl stearate, mono- and di-olefins, such as a-methylstyrene, N-vinylpyrrolidone or N-vinylcarbazole.

For certain purposes, resin mixtures having monomeric or oligomeric constituents containing polymerisable unsaturated groups are used. Such surface coatings can also be cured using compounds of formula (I) or (IA). In that process, radical polymerisation initiators or photoinitiators can additionally be used. The former initiate polymerisation of the unsaturated groups during heat treatment, the latter during UV irradiation.

The invention further pertains to a composition comprising (a) a compound which cures upon the action of an acid or a compound whose solubility is increased upon the action of an acid; and (b) as photosensitive acid donor, at least one compound of the formula (I) or (IA).

According to the invention, the compounds of formula (I) or (IA) can be used together with further photosensitive acid donor compounds (b1), further photoinitiators (d), sensitisers (e) and/or additives (c).

Suitable photosensitive acid donor compounds (b1), sensitizers (e) and addtives (c) are described above.

Examples of additional photoinitiators (d) are radical photoinitiators, such as for example camphor quinone; benzophenone, benzophenone derivatives; ketal compounds, as for example benzildimethylketal; acetophenone, acetophenone derivatives, for example α-hydroxycycloalkyl phenyl ketones or α-hydroxyalkyl phenyl ketones, such as for example 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methylpropionyl)-benzyl]-phenyl}-2-methyl-propan-1-one; 2-hydroxy-1-{4-[4-(2hydroxy-2-methyl-propionyl)-phenoxy]-phenyl}-2-methyl-propan-1-one; dialkoxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyl) aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)propoxy]-ethyl ester; oximeesters, e.g. 1,2-octanedione 1-[4-(phenylthio)phenyl]-2-(Obenzoyloxime), ethanone 1-[9-ethyl-6-(2-methylbenzoyl)-9H-carbazol-3-yl]-1-(O-acetyloxime), 9H-thioxanthene-2-carboxaldehyde 9-oxo-2-(O-acetyloxime), peresters, e,g. benzophenone tetracarboxylic peresters as described for example in EP 126541, monoacyl phosphine oxides, e.g. (2,4,6-trimethyl-benzoyl)diphenylphosphine oxide, ethyl (2,4,6trimethylbenzoyl phenyl) phosphinic acid ester; bisacylphosphine oxides, e.g. bis(2,6-dimethoxy-benzoyl)-(2,4,4-trimethyl-pentyl) phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, halomethyltriazines, e.g. 2-[2-(4-methoxyphenyl)-vinyl]-4,6-bis-trichloromethyl-[1,3,5]triazine, 2-(4-methoxy-phenyl) 4,6-bis-trichloromethyl-[1,3,5]triazine, 2-(3,4-dimethoxy-phenyl)-4,6-bis-trichloromethyl-[1,3,5]-triazine, 2-methyl-4,6-bis-trichloromethyl-[1,3,5]triazine, hexaarylbisimidazole/coinitiators systems, e.g. ortho-chlorohexaphenyl-bisimidazole combined with 2-mercaptobenzthiazole, ferrocenium compounds, or titanocenes, e.g. bis (cyclopentadienyl)bis(2,6-difluoro-3-pyrryl-phenyl) titanium. Further, borate compounds, as for example described in U.S. Pat. No. 4,772,530, EP775706, GB2307474, GB2307473 and GB2304472. The borate compounds preferably are used in combination with electron acceptor compounds, such as, for example dye cations, or thioxanthone derivatives.

Further examples of additional photoinitiators are peroxide compounds, e.g. benzoyl peroxide (other suitable peroxides are described in U.S. Pat. No. 4,950,581, col. 19, I. 17-25) or cationic photoinitiators, such as aromatic sulfonium or iodonium salts, such as those to be found in U.S. Pat. No. 4,950,581, col. 18, I. 60 to col. 19, I. 10, or cyclopentadienyl-arene-iron(II) complex salts, for example ($\eta^6$-isopropylbenzene)($\eta^5$-cyclopentadienyl)-iron(III) hexafluorophosphate.

The compositions can also comprise thermally curable component as additional additives (c). Examples of component (c) include oligomers and/or polymers derived from $\alpha,\beta$-unsaturated acids and derivatives thereof, for example polyacrylates and polymethacrylates, polymethyl methacrylates impact-resistant-modified with butyl acrylate, polyacrylamides and polyacrylonitriles. Further examples of component (c) are urethanes, polyurethanes derived on the one hand from polyethers, polyesters and polyacrylates having free hydroxyl groups and on the other hand from aliphatic or aromatic polyisocyanates, and educts thereof. Component (c) accordingly also includes, for example, crosslinkable acrylic resins derived from substituted acrylic acid esters, for example epoxy acrylates, urethane acrylates and polyester acrylates. Alkyd resins, polyester resins and acrylate resins and modifications thereof that are crosslinked with melamine resins, urea resins, isocyanates, isocyanurates, polyisocyanates, polyisocyanurates and epoxy resins, may also be a constituent of component (c).

Component (c) is, for example, generally a film-forming binder based on a thermoplastic or thermocurable resin, especially on a thermocurable resin. Examples thereof are alkyd, acrylic, polyester, phenolic, melamine, epoxy and polyurethane resins and mixtures thereof. Examples thereof can be found, for example, in Ullmann's Encyclopedia of Industrial Chemistry, 5th Ed., Vol. A18, pp. 368-426, VCH, Weinheim 1991.

Component (c) may also be a cold-curable or hot-curable binder, in which case the addition of a curing catalyst may be advantageous. Suitable catalysts that accelerate the full cure of the binder can be found, for example, in Ullmann's Encyclopedia of Industrial Chemistry, Vol. A18, page 469, VCH Verlagsgesellschaft, Weinheim 1991.

Specific examples of binders suitable as component (c) are:

1. surface-coatings based on cold- or hot-crosslinkable alkyd, acrylate, polyester, epoxy or melamine resins or mixtures of such resins, optionally with the addition of a curing catalyst;
2. two-component polyurethane surface-coatings based on hydroxyl-group-containing acrylate, polyester or polyether resins and aliphatic or aromatic isocyanates, isocyanurates or polyisocyanates;
3. one-component polyurethane surface-coatings based on blocked isocyanates, isocyanurates or polyisocyanates, which are de-blocked during heating; it is also possible to add melamine resins as appropriate;
4. one-component polyurethane surface-coatings based on aliphatic or aromatic urethanes or polyurethanes and hydroxyl-group-containing acrylate, polyester or polyether resins;
5. one-component polyurethane surface-coatings based on aliphatic or aromatic urethane acrylates or polyurethane acrylates having free amine groups in the urethane structure and melamine resins or polyether resins, optionally with the addition of a curing catalyst;
6. two-component surface-coatings based on (poly) ketimines and aliphatic or aromatic isocyanates, isocyanurates or polyisocyanates;
7. two-component surface-coatings based on (poly) ketimines and an unsaturated acrylate resin or a polyacetoacetate resin or a methacrylamidoglycolate methyl ester;
8. two-component surface-coatings based on carboxyl- or amino-group-containing poly-acrylates and polyepoxides;
9. two-component surface-coatings based on anhydride-group-containing acrylate resins and a polyhydroxy or polyamino component;
10. two-component surface-coatings based on acrylate-containing anhydrides and polyepoxides;
11. two-component surface-coatings based on (poly)oxazolines and anhydride-group-containing acrylate resins or unsaturated acrylate resins or aliphatic or aromatic isocyanates, isocyanurates or polyisocyanates;
12. two-component surface-coatings based on unsaturated polyacrylates and polymalonates;
13. thermoplastic polyacrylate surface-coatings based on thermoplastic acrylate resins or extrinsically crosslinking acrylate resins in combination with etherified melamine resins;
14. surface-coating systems based on urethane (meth) acrylate having (meth)acryloyl groups and free isocyanate groups and on one or more compounds that react with isocyanates, for example free or esterified polyols. Such systems have been published, for example, in EP 928800.

Blocked isocyanates that can also be used as component (c) are described, for example, in Organischer Metallschutz: Entwicklung und Anwendung von Beschichtungsstoffen, pages 159-160, Vincentz Verlag, Hanover (1993). These are compounds in which the highly reactive NCO group is "blocked" by reaction with specific radicals, for example a primary alcohol, phenol, acetic acid ethyl ester, ε-caprolactam, phthalimide, imidazole, oxime or amine. The blocked isocyanate is stable in liquid systems and also in the presence of hydroxy groups. Upon heating, the blocking group (protecting group) is removed again and the NCO group is freed.

1-Component and 2-component systems may be used as component (c). Examples of such systems are described in Ullmann's Encyclopedia of Industrial Chemistry, Vol. A18, Paints and Coatings, pages 404-407, VCH Verlagsgesellschaft mbH, Weinheim (1991).

It is possible to optimise the composition by specific adaptation, for example by varying the binder/crosslinking agent ratios. Such measures will be known to the person skilled in the art and are customary in coating technology.

In the curing process according to the invention, component (c) is preferably a mixture based on acrylate/melamine (and melamine derivatives), 2-component polyurethane, 1-component polyurethane, 2-component epoxy/carboxy or 1-component epoxy/carboxy. Mixtures of such systems are also possible, for example the addition of melamine (or derivatives thereof) to 1-component polyurethanes.

Component (c) is preferably a binder based on a polyacrylate with melamine or on a melamine derivative or a system based on a polyacrylate and/or polyester polyol with an unblocked polyisocyanate or polyisocyanurate.

Component (c) may also comprise monomeric and/or oligomeric compounds having ethylenically unsaturated bonds (prepolymers) that additionally contain at least one or more OH, NH₂, COOH, epoxy or NCO group(s) (=c1) that are capable of reaction with the binder and/or the crosslinking agent constituent of component (c). After application and thermal curing, the ethylenically unsaturated bonds are converted to a crosslinked, high molecular weight form by irradiation with UV light. Examples of such components (c) are described, for example, in the above-mentioned publication, Ullmann's Encyclopedia of Industrial Chemistry, 5th Ed., Vol. A18, pages 451-453, or by S. Urano, K. Aoki, N. Tsuboniva and R. Mizuguchi in Progress in Organic Coatings, 20 (1992), 471-486, or by H. Terashima and O. Isozaki in JOCCA 1992 (6), 222.

(c1) may, for example, also be an OH-group-containing unsaturated acrylate, for example hydroxyethyl or hydroxybutyl acrylate or a glycidyl acrylate. Component (c1) may be of any desired structure (for example it may contain units of polyester, polyacrylate, polyether, etc.), provided that it contains an ethylenically unsaturated double bond and additionally free OH, COOH, NH₂, epoxy or NCO groups.

(c1) may, for example, also be obtained by reacting an epoxy-functional oligomer with acrylic acid or methacrylic acid. A typical example of an OH-functional oligomer having vinylic double bonds is

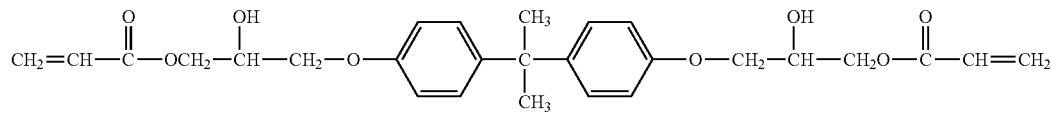

obtained by reaction of

CH₂=CHCOOH with

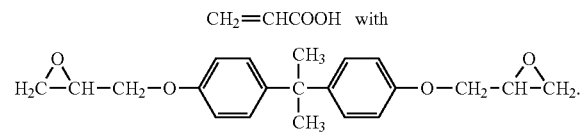

Another possible method of obtaining component (c1) is, for example, the reaction of an oligomer that contains only one epoxy group and has a free OH group at another position in the molecule.

The quantity ratio of the free-radically radiation-curable-polymerisable components to the thermally polymerisable component (c) in the UV- and thermally-crosslinkable formulations is not critical. "Dual-cure" systems are known to the person skilled in the art, who will therefore be familiar with the optimum mixing ratios of the free-radically- and thermally-crosslinkable components according to the intended use. For example, the ratio can be in the range from 5:95 to 95:5, from 20:80 to 80:20 or from 30:70 to 70:30, for example from 40:60 to 60:40.

Examples of "dual-cure" systems, that is to say systems comprising both radiation-curable and thermally curable components, can be found inter alia in U.S. Pat. No. 5,922,473, columns 6 to 10.

The surface coatings may be solutions or dispersions of the surface-coating resin in an organic solvent or in water, but they may also be solventless. Of special interest are surface coatings having a low solvent content, so-called "high solids surface coatings", and powder coating compositions. The surface coatings may be clear lacquers, as used, for example, in the automobile industry as finishing lacquers for multilayer coatings. They may also comprise pigments and/or fillers, which may be inorganic or organic compounds, and metal powders for metal effect finishes.

The surface coatings may also comprise relatively small amounts of special additives customary in surface-coating technology, for example flow improvers, thixotropic agents, leveling agents, antifoaming agents, wetting agents, adhesion promoters, light stabilisers, antioxidants, or sensitisers.

UV absorbers, such as those of the hydroxyphenyl-benzotriazole, hydroxyphenyl-benzophenone, oxalic acid amide or hydroxyphenyl-s-triazine type may be added to the compositions according to the invention as light stabilisers. Individual compounds or mixtures of those compounds can be used with or without the addition of sterically hindered amines (HALS).

Examples of such UV absorbers and light stabilisers are
1. 2-(2'-Hydroxyphenyl)-benzotriazoles, such as 2-(2'-hydroxy-5'-methyl phenyl)-benzotriazole, 2-(3',5'-di-tert-butyl-2'-hydroxyphenyl)-benzotriazole, 2-(5'-tert-butyl-2'-hydroxyphenyl)benzotriazole, 2-(2'-hydroxy-5'-(1,1,3,3-tetramethylbutyl)phenyl)-benzotriazole, 2-(3',5'-dit-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'hydroxy-4'-octyloxyphenyl)-benzotriazole, 2-(3',5'-di-tert-amyl-2'-hydroxyphenyl)-benzotriazole, 2-(3',5'-bis-(α, α-dimethylbenzyl)-2'-hydroxyphenyl)-benzotriazole, mixture of 2-(3'tert-butyl-2'-hydroxy-5'-(2-octyloxycarbonylethyl)phenyl)-5-chloro-benzotriazole, 2-(3'-t-butyl-5'-[2-(2-ethyl-hexyloxy)-carbonylethyl]-2'-hydroxyphenyl)-5-chloro-benzotriazole, 2-(3'-tertbutyl-2'-hydroxy-5'-(2-methoxycarbonylethyl)phenyl)-5-chloro-benzotriazole, 2(3'-tert-butyl2'-hydroxy-5'-(2-methoxycarbonylethyl)phenyl)-benzotriazole, 2-(3'-tert-butyl-2'-hydroxy-5'(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)-benzotriazole and 2-(3'-tertbutyl-2'-hydroxy-5'-(2-isooctyloxycarbonylethyl) phenyl-benzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—CH₂CH₂—COO(CH₂)₃]₂— wherein R=3'-tert-butyl-4'-hydroxy-5'-2H-benzotriazol-2-yl-phenyl.

2. 2-Hydroxybenzophenones, such as the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.

3. Esters of unsubstituted or substituted benzoic acids, such as 4-tert-butyl-phenyl salicylate, phenyl salicylate, octylphenyl salicylate, dibenzoylresorcinol, bis(4-tert-butyl-benzoyl)resorcinol, benzoylresorcinol, 3,5-di-tert-butyl-4-hydroxybenzoic acid 2,4-ditert-butylphenyl ester, 3,5-di-tert-butyl-4-hydroxybenzoic acid hexadecyl ester, 3,5-ditertbutyl-4-hydroxybenzoic acid octadecyl ester, 3,5-di-tert-butyl-4-hydroxybenzoic acid 2-methyl-4,6-di-tert-butylphenyl ester.

4. Acrylates, such as α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(b-carbomethoxy-β-cyanovinyl)-2-methyl-indoline.

5. Sterically hindered amines, such as bis(2,2,6,6-tetramethyl-piperidyl)sebacate, bis(2,2,6,6-tetramethyl-piperidyl)succinate, bis(1,2,2,6,6-pentamethylpiperidyl)sebacate, n-butyl-3,5-di-tert-butyl-4-hydroxybenzyl-malonic acid bis (1,2,2,6,6-pentamethylpiperidyl) ester, condensation product of 1-hydroxyethyl-2,2,6,6-tetramethyl-4-hydroxypiperidine and succinic acid, condensation product of N,N'-bis(2, 2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2, 6,6-tetramethylpiperidine, bis(1,2,2,6,6-pentamethylpiperidyl)-2-n-butyl-2-(2-hydroxy3,5-di-tert-butylbenzyl)malonate, 3-n-octyl-7,7,9,9-tetramethyl-1,3,8-triazaspiro[4.5] decane2,4-dione, bis(1-octyloxy-2,2,6,6-tetramethyl piperidyl)sebacate, bis(1-octyloxy-2,2,6,6-tetramethylpiperidyl)succinate, condensation product of N,N'-bis(2,2,6,6-tetra-methyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylaminol, 2,2,6,6-pentamethylpiperidyl)-1,3,5-triazine and 1,2-bis (3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2, 5-dione, 3-dodecyl-1-(1,2,2,6,6-pentamethyl-4-piperidyl) pyrrolidine-2,5-dione.

6. Oxalic acid diamides, such as 4,4'-dioctyloxy-oxanilide, 2,2'-diethoxy-oxanilide, 2,2'-di-octyloxy-5,5'-di-tert-butyl-oxanilide, 2,2'-didodecyloxy-5,5'-di-tert-butyl-oxanilide, 2-ethoxy-2'ethyl-oxanilide, N,N'-bis(3-dimethylaminopropyl)oxalamide, 2-ethoxy-5-tertbutyl-2'-ethyloxanilide and a mixture thereof with 2-ethoxy-2'-ethyl-5,4'-di-tert-butyloxanilide, mixtures of o- and p-methoxy- and of o- and p-ethoxy-di-substituted oxanilides.

7. 2-(2-Hydroxyphenyl)-1,3,5-triazines, such as 2,4,6-tris (2-hydroxy-4-octyloxyphenyl)1,3,5triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2, 4-dimethylphenyl)-1,3,5-triazine, 2-(2-hydroxy-4-octyloxyphenyl)4,6-bis(4-methylphenyl)-1,3,5-triazine, 2-(2-hydroxy-4-dodecyloxyphenyl)-4,6-bis(2,4-dimethylphenyl)-1,3,5triazine, 2-[2-hydroxy-4-(2-hydroxy-3-butyloxy-propyloxy)phenyl]-4,6-bis(2,4-dimethyl-phenyl)-1,3, 5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl-/tridecyl-oxy-(2-hydroxypropyl)oxy-2-hydroxy-phenyl]4,6-bis(2,4-dimethylphenyl)-1,3,5-triazine.

8. Phosphites and phosphonites, such as triphenyl phosphite, diphenyl alkyl phosphites, phenyl dialkyl phosphites, tris(nonylphenyl) phosphite, trilauryl phosphite, trioctadecyl phosphite, distearyl-pentaerythritol diphosphite, tris(2,4-di-tert-butylphenyl) phosphite, diisodecylpentaerythritol diphosphite, bis(2,4-di-tert-butylphenyl)pentaerythritol diphosphite, bis(2,6-di-tertbutyl-4-methylphenyl)pentaerythritol diphosphite, bisisodecyloxy-pentaerythritol diphosphite, bis(2,4-di-tert-butyl-6-methylphenyl)pentaerythritol diphosphite, bis-(2,4,6-tri-tert-butylphenyl)pentaerythritol diphosphite, tristearyl-sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tertbutyl-6-methylphenyl)methyl phosphite, bis(2,4-di-tert-butyl-6-methylphenyl)ethyl phosphite.

Such light stabilisers can also be added, for example, to an adjacent surface-coating layer from which they gradually diffuse into the layer of stoving lacquer to be protected. The adjacent surface-coating layer may be a primer under the stoving lacquer or a finishing lacquer over the stoving lacquer.

It is also possible to add to the resin, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat. No. 4,017,652), 3-acyl-coumarins (as described, for example, in U.S. Pat. No. 4,366,228, EP738928, EP22188), keto-coumarines (as described e.g. in U.S. Pat. No. 5,534,633, EP538997, JP8272095-A), styryl-coumarines (as described e.g. in EP624580), 3-(aroylmethylene)-thiazolines, thioxanthones, condensed aromatic compounds, such as perylene, aromatic amines (as described, for example, in U.S. Pat. No. 4,069, 954 or WO96/41237) or cationic and basic colourants (as described, for example, in U.S. Pat. No. 4,026,705), for example eosine, rhodanine and erythrosine colourants, as well as dyes and pigments as described for example in JP8320551A, EP747771, JP7036179A, EP619520, JP6161109A, JP6043641A, JP6035198A, WO93/15440, EP568993, JP5005005A, JP5027432A, JP5301910A, JP4014083A, JP4294148A, EP359431, EP103294, U.S. Pat. No. 4,282,309, EP39025, EP5274, EP727713, EP726497 or DE 2027467.

Other customary additives are—depending on the intended use—optical brighteners, fillers, pigments, colourants, wetting agents or flow improvers and adhesion promoters. For curing thick and pigmented coatings, the addition of micro glass beads or powdered glass fibres, as described in U.S. Pat. No. 5,013,768, is suitable.

Oxime sulfonate derivatives can also be used, for example, in hybrid systems. These systems are based on formulations that are fully cured by two different reaction mechanisms. Examples thereof are systems that comprise components that are capable of undergoing an acid-catalysed crosslinking reaction or polymerisation reaction, but that also comprise further components that crosslink by a second mechanism. Examples of the second mechanism are radical full cure, oxidative crosslinking or humidity-initiated crosslinking. The second curing mechanism may be initiated purely thermally, if necessary with a suitable catalyst, or also by means of light using a second photoinitiator. Suitable additional photoinitiators are described above.

If the composition comprises a radically crosslinkable component, the curing process, especially of compositions that are pigmented (for example with titanium dioxide), can also be assisted by the addition of a component that is radical-forming under thermal conditions, such as an azo compound, for example 2,2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP245639, or thermolatent radical initiators as described for example in U.S. Pat. No. 6,929,896, WO 2010057922, WO2012113829, WO2012101245, WO2013156509 or WO2014064064. The addition of redox initiators, such as cobalt salts, enables the curing to be assisted by oxidative crosslinking with oxygen from the air.

The surface coating can be applied by one of the methods customary in the art, for example by spraying, painting or immersion. When suitable surface coatings are used, electrical application, for example by anodic electrophoretic deposition, is also possible. After drying, the surface coating film is irradiated. If necessary, the surface coating film is then fully cured by means of heat treatment.

It is known from EP592139 that sulfonate derivatives can be used as acid generators, which can be activated by light in compositions that are suitable for the surface treatment and cleaning of glass, aluminium and steel surfaces. The use of such compounds in organosilane systems results in compositions that have significantly better storage stability than those obtained when the free acid is used. The compounds of formula (I) or (IA) are also suitable for this application.

The oxime sulfonate derivatives of the present invention can also be used to shape polymers that undergo an acid induced transition into a state where they have the required properties using photolithography. For instance the oxime sulfonate derivatives can be used to pattern conjugated emissive polymers as described, for example, in M. L. Renak; C. Bazan; D. Roitman; Advanced materials 1997, 9, 392. Such patterned emissive polymers can be used to manufacture microscalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coatings, insulating layers and buffer layers in the production of microchips and printed circuit boards.

The formulations of the invention may also be used as conformal coatings, photoimagable insulating layers and dielectrics.

It is known that conjugated polymers like, e.g. polyanilines can be converted from semiconductive to conductive state by means of proton doping. The oxime sulfonate derivatives of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

Suitable radiation sources for the compositions comprising compounds of formula (I) or (IA) are radiation sources that emit radiation of a wavelength of approximately from 10 to 1500, for example from 10 to 1000, or preferably from 10 to 700 nanometers as well as e-beam radiation and high-energy electromagnetic radiation such as X-rays. Both, point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights or laser plasma. The distance between the radiation source and the substrate according to the invention to be irradiated can vary, for example, from 2 cm to 150 cm, according to the intended use and the type and/or strength of the radiation source. Suitable radiation sources are especially mercury vapour lamps, especially medium and high pressure mercury lamps, from the radiation of which emission lines at other wavelengths can, if desired, be filtered out. That is especially the case for relatively short wavelength radiation. It is, however, also possible to use low energy lamps (for example fluorescent tubes) that are capable of emitting in the appropriate wavelength range. An example thereof is the Philips TL03 lamp. Another type of radiation source that can be used are the light emitting diodes (LED) that emitt at different wavelengths throughout the whole spectrum either as small band emitting source or as broad band (white light) source. Also suitable are laser radiation sources, for example excimer lasers, such as Kr—F lasers for irradiation at 248 nm, Ar—F lasers at 193 nm, or $F_2$ laser at 157 nm. Lasers in the visible range and in the infrared range can also be used. Especially suitable is radiation of the mercury i, h and g lines at wavelengths of 365, 405 and 436 nanometers. A suitable laser-beam source is, for example, the argon-ion laser, which emits radiation at wavelengths of 454, 458, 466, 472, 478, 488 and 514 nanometers. Nd-YAG-lasers emitting light at 1064 nm and its second and third harmonic (532 nm and 355 nm respectively) can also be used. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities. On irradiation, the oxime sulfonate derivatives in the composition in the irradiated sections of the surface coating decompose to form the acids.

The invention further relates to the use of the photoresist composition to manufacture color filters for a variety of display applications and for image sensors such as charge coupled device (CCD) and complementary metal-oxide semiconductor (CMOS), spacers for LCD, overcoat layer for color filter and LCD, sealant for LCD, optical films for a variety of display applications, insulation layer for LCD, organic light-emitting diode displays (OLED), touch panels and flexible displays, resists or photosensitive compositions to generate structures or layers in the manufacturing processes of plasma-display panels, electroluminescence displays, OLED, touch panels, flexible displays and LCD, solder resists, as a photoresist material used for forming dielectric layers in a sequential build-up layer of a printed circuit board.

The compositions according to the invention are particularly suitable for the production of color filters or color mosaic systems, such as described, for example, in EP 320 264.

The color filters can be used, for example, for flat panel display technology such as LCD, electroluminescent display and plasma display, for image sensors such as CCD and CMOS, and the like.

The color filters usually are prepared by forming red, green and blue pixels and optionally black matrix on a glass substrate. In these processes photocurable compositions according to the invention can be employed. A particularly preferred method of use comprises adding of the coloring matters, dyes and pigments of red, green and blue colors to the light-sensitive resin composition of the present invention, coating of the substrate with the composition, drying of the coating with a short heat treatment, patternwise exposure of the coating (i.e. through a suitable mask) to actinic radiation and subsequent development of the pattern in a suitable aqueous alkaline developer solution and a heat treatment. Thus, by subsequently applying a red, green, blue and optionally black pigmented coating, in any desired order, on top of each other with this process a color filter layer with red, green and blue color pixels and optionally a black matrix can be produced.

In addition to a process in which the light-sensitive resin composition is coated on a substrate and dried, the light-sensitive resin composition of the present invention can be used as well for a layer transfer material. That is, the light-sensitive resin composition is layer-wise provided directly on a temporary support, preferably on a polyethylene terephthalate film, or on a polyethylene terephthalate film on which an oxygen-shielding layer and a peeling layer or the peeling layer and the oxygen-shielding layer are provided. Usually, a removable cover sheet made of a synthetic resin is laminated thereon for a protection in handling. Further, there can be applied as well a layer structure in which an alkali soluble thermoplastic resin layer and an intermediate layer are provided on a temporary support and further a light-sensitive resin composition layer is provided thereon (JP5-173320A).

The above cover sheet is removed in use and the light-sensitive resin composition layer is laminated on a permanent support. Subsequently, peeling is carried out between those layer and a temporary support when an oxygen-shielding layer and a peeling layer are provided, between the peeling layer and the oxygen-shielding layer when the peeling layer and the oxygen-shielding layer are provided, and between the temporary support and the light-sensitive resin composition layer when either the peeling layer or the oxygen-shielding layer is not provided, and the temporary support is removed.

The developer solution can be used in all forms known to the person skilled in the art, for example in form of a bath solution, puddle, or a spraying solution. In order to remove the non-cured portion of the light-sensitive resin composition layer, there can be combined the methods such as rubbing with a rotary brush and rubbing with a wet sponge. Usually, the temperature of the developing solution is preferably at and around room temperature to 40° C. The developing time is changeable according to the specific kind of the light-sensitive resin composition, the alkalinity and temperature of the developing solution, and the kind and concentration of the organic solvent in the case where it is added. Usually, it is 10 seconds to 2 minutes. It is possible to put a rinsing step after the development processing.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 250° C., for about 2 to about 60 minutes.

Examples for color filter resists, the composition of such resists and the processing conditions are given by T. Kudo et al., Jpn. J. Appl. Phys. Vol. 37 (1998) 3594; T. Kudo et al., J. Photopolym. Sci. Technol. Vol 9 (1996) 109; K. Kobayashi, Solid State Technol. November 1992, p. S15-S18; U.S. Pat. No. 5,368,976; U.S. Pat. No. 5,800,952; U.S. Pat. No. 5,882,843; U.S. Pat. No. 5,879,855; U.S. Pat. No. 5,866,298; U.S. Pat. No. 5,863,678; JP 06-230212A; EP320264; JP09-269410A; JP10-221843A; JP01-090516A; JP10-171119A, U.S. Pat. No. 5,821,016, U.S. Pat. No. 5,847,015, U.S. Pat. No. 5,882,843, U.S. Pat. No. 5,719,008, EP881541, or EP902327.

Instead of forming a black matrix using a photosensitive composition and patterning the black photosensitive composition photolithographically by patternwise exposure to form the black pattern separating the red green and blue colored areas on the transparent substrate it is alternatively possible to use an inorganic black matrix. Such inorganic black matrix can be formed from deposited (i.e. sputtered) metal (i.e. chromium) film on the transparent substrate by a suitable imaging process, for example utilizing photolithographic patterning by means of an etch resist, etching the inorganic layer in the areas not protected by the etch resist and then removing the remaining etch resist.

The photosensitive or thermosetting composition of the present invention can also be used to form such overcoat layers, because a cured film of the composition is excellent in flatness, hardness, chemical and thermal resistance, transparency especially in a visible region, adhesion to a substrate, and suitability for forming a transparent conductive film, e.g., an ITO film, thereon. In the production of a protective layer, there has been a demand that unnecessary parts of the protective layer, for example on scribing lines for cutting the substrate and on bonding pads of solid image sensors should be removed from the substrate as described in JP57-42009A, JP1-130103A and JP1-134306A. In this regard, it is difficult to selectively form a protective layer with good precision using the above-mentioned thermosetting resins. The photosensitive composition, however, allows to easily remove the unnecessary parts of the protective layer by photolithography.

The photosensitive compositions according to the invention can further be used for manufacturing spacers, which control a cell gap of the liquid crystal part in liquid crystal display panels. Since the properties of light transmitted or reflected through the liquid crystal layer in a liquid crystal display are dependent on the cell gap, the thickness accuracy and uniformity over the pixel array are critical parameters for the performance of the liquid crystal display unit. By using photolithographic process, columns of a resin can be formed as spacers in the region between the pixel array region and the counter electrode to form a prescribed cell gap. Photosensitive materials having adhesive properties with photolithography are commonly used, for instance, in the manufacturing process of color filters. This method is advantageous compared with the conventional method using spacer beads in the points that location, number and height of the spacers may be controlled freely. In a color liquid crystal display panel, such spacers are formed in the non-imaging area under black matrix of color filter elements. Therefore, the spacers formed using photosensitive compositions do not decrease brightness and optical aperture.

Photosensitive compositions for producing protective layer with spacers for color filters are disclosed in JP2000-81701A and dry film type photoresists for spacer materials are also disclosed in JP11-174459A and JP11-174464A. As described in the documents, the photosensitive compositions, liquid and dry film photoresists, are comprising at least an alkaline or acid soluble binder polymer, a radically polymerizable monomer, and a radical initiator. In some cases, thermally crosslinkable components such as epoxide and carboxylic acid may additionally be included.

The steps to form spacers using a photosensitive composition are as follows: a photosensitive composition is applied to the substrate, for instance a color filter panel and after the substrate is prebaked, it is exposed to light through a mask. Then, the substrate is developed with a developer and patterned to form the desired spacers. When the composition contains some thermosetting components, usually a post-baking is carried out to thermally cure the composition.

The photocurable compositions according to the invention are suitable for producing spacers for liquid crystal displays (as described above).

The compositions according to the invention are also suitable for manufacturing interlayer insulating layers or dielectric layers in a liquid crystal display, and more particularly in specific LCD structures such as color filter on array type and reflection type LCDs. Explanation on this application in detail is disclosed in JP2014-10382A, JP2014-10200, JP2013-242537A, JP 2013-242511A, and JP2013-231868.

The photosentive (radiation-sensitive) acid-generating compounds of the formula (I) and (IA) of the present invention are in particular suitable in compositions for manufacturing insulating layers.

For example in the formulations as described in

JP5-165214-A, which proposes a photosensitive resin composition including (A) a resin that is soluble in an alkaliaqueous solution and is a copolymer of (a) an unsaturated carboxylic acid or an unsaturated carboxylic acid anhydride, (b) a radically polymerizable compound having an epoxy group and (c) another radically polymerizable compound; and (B) a radiation-sensitive acid-generating compound.

JP Patent No. 4207604, which proposes a photosensitive resin composition including (A) a high molecular weight polymer having an acetal structure and/or a ketal structure and an epoxy structure, and having a weight average molecular weight of 2000 or more (polystyrene converted) measured by gel-permeation chromatography; and (B) a compound that generates an acid having a pKa of 4.0 or less when exposed to radiation. JP2009-098616A, which proposes a photosensitive resin composition including at least (A) a resin that contains a structural unit having an acid dissociative group represented by the following formula

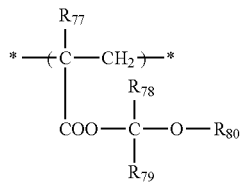

and having a functional group capable of forming a covalent bond by reacting with a carboxyl group, the resin being insoluble with respect to alkali but becoming alkali soluble upon dissociation of the acid-dissociative group; and (B) a compound that generates an acid when exposed to actinic light or radiation, where in the above formula $R_{77}$ is H, $CH_3$, halogen or CN, $R_{78}$ and $R_{79}$ each are H or alkyl, where at least one of $R_{78}$ and $R_{79}$ is alkyl; and $R_{80}$ is aryl or aralkyl, and $R_{78}$ and $R_{80}$ or $R_{79}$ and $R_{80}$ may be bonded to each other to form a cyclic ether.

Insulation Layers

The compounds of the formula (I) and (IA) of the present invention are in particular suited as photosensitive acid-generators in the resin compositions as disclosed for example in US20120045616A and US20130171415A, e.g for the formation of insultaing layers. According to these publications the composition comprises a radiation sensitive acid generator compound and a resin (A) comprising a structural unit having an acid dissociative group and a structural unit having a functional group capable of forming a covalent bond by reacting with a carboxyl group or a phenolic hydroxyl group.

In the preferred compositions of the present invention the radiation-sensitive acid generator compound as described in US20120045616A and US20130171415A is replaced by the radiation sensitive acid generator compound of the formula (I) or (IA) of the present invention.

The specific resin (A) as described in these above publications, as well as in the present text below is preferred as component (a), or (a1) respectively as are subject in the present claims.

The specific resin (A), for example used in the composition for preparing insulating layers, is a resin that at least includes a structural unit having an acid decomposable group that decomposes by acid and generates a carboxyl group or a phenolic hydroxyl group and a structural unit capable of forming a covalent bond by reacting with a carboxyl group or a phenolic hydroxyl group.

The specific resin (A) may include only one kind of each of the structural units, respectively, or plural kinds thereof may be included in combination. In addition, as will be described later, the specific resin (A) may include a structural unit having a structure different from that of the aforementioned structural units.

The specific resin (A), for example used in the composition for preparing insulating layers, is a resin that at least includes a structural unit having an acid decomposable group that decomposes by acid and generates a carboxyl group or a phenolic hydroxyl group and a structural unit capable of forming a covalent bond by reacting with a carboxyl group or a phenolic hydroxyl group.

The specific resin (A) may include only one kind of each of the structural units, respectively, or plural kinds thereof may be included in combination. In addition, as will be described later, the specific resin (A) may include a structural unit having a structure different from that of the aforementioned structural units.

Acid Dissociative Group (Acid Decomposable Group).

The acid dissociative group contained in the specific resin (A) refers to a group that generates a carboxyl group or a phenolic hydroxyl group via decomposition with acid (hereinafter, also simply referred to as an "acid decomposable group"). Examples of the structural units having an acid dissociative group in the present invention include a structural unit having group that generates a carboxyl group by decomposition (dissociation) with acid, specifically, a structural unit having a structure represented by the following formula (Iaa) or (IIaa); and a structural unit having a group that generates a phenolic hydroxyl group by decomposition with acid, specifically, a structural unit having a structure represented by the following formula (Ibb) or (IIbb). The specific resin (A) is preferably a resin that includes at least one selected from these structural units:

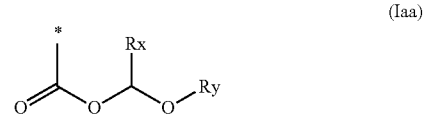
(Iaa)

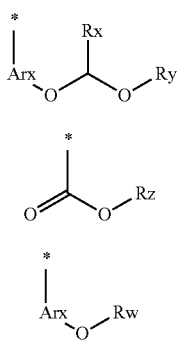

(Ibb)

(IIaa)

(IIbb)

In formulas (Iaa) and (Ibb), Ry independently represents a linear or branched alkyl group or cycloalkyl group, which are unsubstituted or substituted; Rx each independently represents a linear or branched alkyl group; Arx represents a divalent aromatic group; and the symbol * represents a bonding site with another structure.

In formula (IIaa), Rz represents a tertiary alkyl group or a 2-tetrahydropyranyl group. In formula (IIbb), Rw represents a tertiary alkyl group, a tert-butoxycarbonyl group or a 2-tetrahydropyranyl group; Arx represents a divalent aromatic group; and the symbol * represents a bonding site with another structure.

The linear or branched alkyl group represented by Ry preferably has 1 to 20 carbon atoms, more preferably 1 to 10 carbon atoms, and still more preferably 1 to 7 carbon atoms.

Examples of the linear or branched alkyl groups are given above.

When Ry represents a cycloalkyl group, the cycloalkyl group preferably has 3 to 20 carbon atoms, more preferably 3 to 10 carbon atoms, and still more preferably 5 to 7 carbon atoms.

Examples of the cycloalkyl group represented by Ry include a cyclopropyl group, a cyclobutyl group, a cyclopentyl group, a cyclohexyl group, a cycloheptyl group, a cyclooctyl group, a norbornyl group and an isobornyl group.

The linear or branched alkyl group or cycloalkyl group represented by Ry may have a substituent, for examples include a cycloalkyl group having 3 to 10 carbon atoms, an aryl group having 6 to 10 carbon atoms, a halogen atom (such as a fluorine atom, a chlorine atom, a bromine atom, or iodine atom), a cyano group, a nitro group, a hydroxyl group and an alkoxy group having 1 to 10 carbon atoms. Additionally, a ring structure of the cycloalkyl group may have, as a substituent, an alkyl group having 1 to 10 carbon atoms (such as a methyl group, an ethyl group, a propyl group or a butyl group).

As the halogen atom as the substituent, a fluorine atom is useful, and a fluoroalkyl group containing a fluorine atom, such as $CF_3$, is a particularly useful substituent. Additionally, the linear or branched alkyl group or the cycloalkyl group represented by Ry is preferably an alkyl group having 1 to 10 carbon atoms, a cycloalkyl group having 3 to 10 carbon atoms or an aralkyl group having 7 to 11 carbon atoms, more preferably an alkyl group having 1 to 6 carbon atoms, a cycloalkyl group having 3 to 6 carbon atoms or a benzyl group, still more preferably an ethyl group or a cyclohexyl group, and particularly preferably an ethyl group.

In formulas (Iaa) and (Ibb), Rx each independently represents a linear or branched alkyl group. The linear or branched alkyl group represented by Rx preferably has 1 to 20 carbon atoms, more preferably 1 to 10 carbon atoms, and still more preferably 1 to 7 carbon atoms.

Additionally, the linear or branched alkyl group represented by Rx is preferably an alkyl group having 1 to 6 carbon atoms, and particularly preferably a methyl group.

In formula (Ibb), Arx represents a divalent aromatic group and has a structure having OCH(ORy)(Rx) on an aromatic ring.

The divalent aromatic group represented by Arx is not specifically limited, and examples of the divalent aromatic group include a phenylene group, a substituted phenylene group, a naphthylene group and a substituted naphthylene group. The divalent aromatic group is preferably a phenylene group or a substituted phenylene group, more preferably an unsubstituted phenylene group, and still more preferably 1,4-phenylene group.

In addition, the divalent aromatic group represented by Arx may have a substituent on an aromatic ring. Examples of the substituent that can be introduced in the aromatic ring include a linear or branched alkyl group having 1 to 10 carbon atoms (such as a methyl group, an ethyl group, a propyl group, or a butyl group), a cycloalkyl group having 3 to 10 carbon atoms, an aryl group having 6 to 10 carbon atoms, a halogen atom (such as a fluorine atom, a chlorine atom, a bromine atom, or an iodine atom), a cyano group, a nitro group, a hydroxyl group and an alkoxy group having 1 to 10 carbon atoms. These substituents may be further substituted by a substituent such as the above substituents.

The structural unit having an acid decomposable group preferably includes at least one selected from the structures represented by formulas (Iaa) and (Ibb).

The carboxylic acid monomer that can form a structural unit having a structure represented by formula (Iaa) by protecting a carboxyl group is not specifically limited as long as it can form a structural unit having an acid decomposable group having the above-mentioned structure by protecting a carboxyl group. Examples of the carboxylic acid monomer include monocarboxylic acids such as acrylic acid, methacrylic acid, crotonic acid and α-methyl-p-carboxystyrene; and dicarboxylic acids such as maleic acid, fumaric acid, citraconic acid, mesaconic acid and itaconic acid. Additionally, the structural unit having an acid decomposable group is preferably a monomer unit derived from a carboxylic acid in which the carboxyl group is protected.

A monomer having a phenolic hydroxyl group that can form a structural unit having a structure represented by formula (Ibb) by protecting the phenolic hydroxyl group is not specifically limited, as long as it can form a structural unit having an acid decomposable group by protecting the phenolic hydroxyl group. Examples of the monomer include hydroxystyrenes such as p-hydroxystyrene and a-methyl-p-hydroxystyrene, compounds mentioned in paragraphs [0011] to [0016] of JP-A No. 2008-40183; 4-hydroxybenzoic acid derivatives mentioned in paragraphs [0007] to [0010] of Japanese Patent No. 2888454; an addition-reaction product of 4-hydroxybenzoic acid and glycidyl methacrylate and an addition-reaction product of 4-hydroxybenzoic acid and glycidyl acrylate.

Among them, more preferred are α-methyl-p-hydroxystyrene, the compounds mentioned in paragraphs [0011] to [0016] of JP-A No. 2008-40183, the 4-hydroxybenzoic acid derivatives mentioned in paragraphs [0007] to [0010] of Japanese Patent No. 2888454, the addition-reaction product of 4-hydroxybenzoic acid and glycidyl methacrylate and the addition-reaction product of 4-hydroxybenzoic acid and glycidyl acrylate.

Among these structures, a particularly preferable structural unit having an acid decomposable group is a structural unit represented by formula (IIIaa)

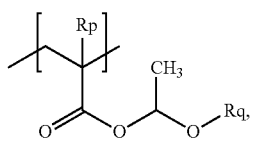

wherein

Rq represents a linear or branched alkyl group or cycloalkyl group, and preferable embodiments of Rq are the same as the preferable embodiments of Ry in formulas (Ia) and (Ib); Rp represents a hydrogen atom or a methyl group.

Preferable specific examples of a radical polymerizable monomer used to form a structural unit represented by formula (IIIaa) include 1-ethoxyethyl methacrylate, 1-ethoxyethyl acrylate, 1-methoxyethyl methacrylate, 1-methoxyethyl acrylate, 1-n-butoxyethyl methacrylate, 1-n-butoxyethyl acrylate, 1-n-isobutoxyethyl methacrylate, 1-n-isobutoxyethyl acrylate, 1-(2-ethylhexyloxy)ethyl methacrylate, 1-(2-ethylhexyloxy)ethyl acrylate, 1-n-propoxyethyl methacrylate, 1-n-propoxyethyl acrylate, 1-cyclohexyloxyethyl methacrylate, 1-cyclohexyloxyethyl acrylate, 1-(2-cyclohexylethoxy)ethyl methacrylate, 1-(2-cyclohexylethoxy)ethyl acrylate, 1-benzyloxyethyl methacrylate and 1-benzyloxyethyl acrylate. Particularly preferred examples are 1-ethoxyethyl methacrylate and 1-ethoxyethyl acrylate. These structural units may be included alone or in a combination of two or more kinds thereof.

The radical polymerizable monomer used to form a structural unit having an acid decomposable group may be a commercially available product or a product synthesized by a known method. For example, as shown below, the radical polymerizable monomer can be synthesized by allowing (meth)acrylic acid to react with a vinyl ether compound in the presence of an acid catalyst.

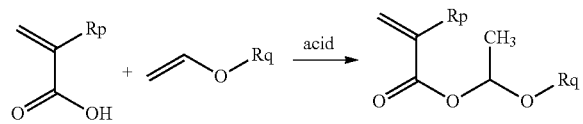

In the above scheme, each of Rq and Rp corresponds to Rq and Rp in formula (IIIaa).

It is also possible to form a structural unit having an acid decomposable group by polymerizing a monomer containing a carboxyl group or a phenolic hydroxyl group with a monomer (described later) or its precursor, and then reacting the carboxyl group or the phenolic hydroxyl group with a vinyl ether compound. Specific examples of a preferable monomer unit that can be obtained by this method are the same as those of the preferable specific examples of the above radical polymerizable monomer.

In formulas (IIaa) and (IIbb) above, Rz represents a tertiary alkyl group, a 2-tetrahydropyranyl group or a 2-tetrahydrofuranyl group; Rw represents a tertiary alkyl group, a tert-butoxycarbonyl group, a 2-tetrahydropyranyl group or a 2-tetrahydrofuranyl group; Arx represents a divalent aromatic group; and the symbol * represents a bonding site with another structure. The tertiary alkyl group represented by Rz and Rw 4 preferably has 4 to 20 carbon atoms, more preferably 4 to 14 carbon atoms, and still more preferably 4 to 8 carbon atoms.

The tertiary alkyl group or the 2-tetrahydropyranyl group represented by Rz, the tertiary alkyl group, the tert-butoxycarbonyl group, the 2-tetrahydropyranyl group or the 2-tetrahydrofuranyl group represented by Rw, and the divalent aromatic group represented by Arx may have a substituent. Examples of the substituent include an alkyl group having 1 to 10 carbon atoms (such as a methyl group, an ethyl group, a propyl group or a butyl group), a cycloalkyl group having 3 to 10 carbon atoms, an aryl group having 6 to 10 carbon atoms, a halogen atom (such as a fluorine atom, a chlorine atom, a bromine atom, or an iodine atom), a cyano group, a nitro group, a hydroxyl group and an alkoxy group having 1 to 10 carbon atoms. These substituents may be further substituted by a substituent selected from the above substituents.

The tertiary alkyl group represented by Rz and Rw is preferably at least one selected from a group consisting of groups represented by the following formula (Vaa) —C[(Rs)(Rt)(Ru)], wherein Rs, Rt and Ru each independently represent an alkyl group having 1 to 12 carbon atoms, a cycloalkyl group having 3 to 12 carbon atoms, an aryl group having 6 to 12 carbon atoms or an aralkyl group having 7 to 12 carbon atoms, and any two of Rs, Rt and Ru may be bonded to each other to form a ring together with the carbon atom to which Rs, Rt and Ru are bonded.

In formula (Vaa), the alkyl group having 1 to 12 carbon atoms represented by each of Rs, Rt and Ru may be linear or branched. Examples of the alkyl group having 1 to 12 carbon atoms include a methyl group, an ethyl group, an n-propyl group, an i-propyl group, an n-butyl group, an i-butyl group, a sec-butyl group, an n-pentyl group, a neopentyl group, an n-hexyl group, an n-heptyl group, an n-octyl group, a 2-ethylhexyl group, an n-nonyl group and an n-decyl group.

Examples of the cycloalkyl group having 3 to 12 carbon atoms include a cyclopropyl group, a cyclobutyl group, a cyclopentyl group, a cyclohexyl group, a cycloheptyl group, a cyclooctyl group, a norbornyl group and an isobornyl group.

Examples of the aryl group having 6 to 12 carbon atoms include a phenyl group, a tolyl group, a xylyl group, a cumenyl group and a 1-naphthyl group.

Examples of the aralkyl group having 7 to 12 carbon atoms include a benzyl group, an α-methylbenzyl group, a phenethyl group and a naphthylmethyl group.

Examples of the ring structure in which Rs and Rt, Rs and Ru, or Rt and Ru are bonded to each other include a cyclobutyl group, a cyclopentyl group, a cyclohexyl group, a cycloheptyl group, a tetrahydrofuranyl group, an adamantyl group and a tetrahydropyranyl group.

Among these structures, a particularly preferred structural unit having an acid decomposable group is a structural unit represented by the following formula (IVaa)

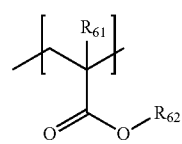

wherein, $R_{62}$ represents a tertiary alkyl group, a 2-tetrahydropyranyl group or a 2-tetrahydrofuranyl group, and $R_{61}$ represents a hydrogen atom or a methyl group.

In formula (IVaa), a preferable embodiment of $R_{62}$ is the same as that of Rx in formula (IIaa).

Preferable specific examples of a radical polymerizable monomer used to form a structural unit represented by formula (IVaa) include tert-butyl methacrylate, tert-butyl acrylate, tetrahydro-2H-pyran-2-yl methacrylate, tetrahydro-2H-pyran-2-yl acrylate, tetrahydro-2H-furan-2-yl methacrylate, tetrahydro-2H-furan-2-yl acrylate, 2-methyl-2-adamantyl methacrylate, 2-methyl-2-adamantyl acrylate, 1-methylcyclohexyl methacrylate and 1-methylcyclohexyl acrylate. Particularly preferred monomers are tert-butyl methacrylate and tert-butyl acrylate. These structural units can be used alone or as a combination of two or more kinds thereof.

Preferable specific examples of the acid decomposable group-containing structural unit include the following monomer units:

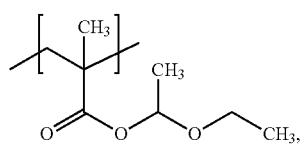
(a1-1)

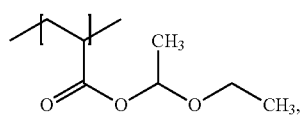
(a1-2)

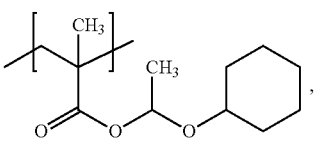
(a1-3)

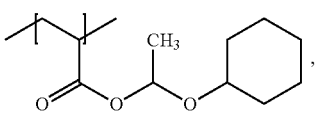
(a1-4)

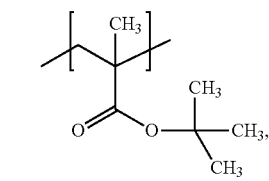
(a2-1)

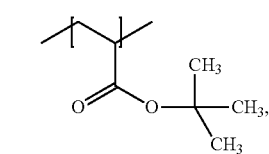
(a2-2)

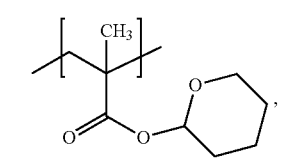
(a2-3)

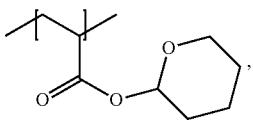
(a2-4)

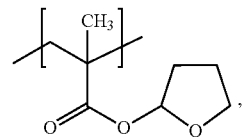
(a2-5)

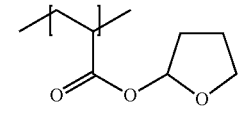
(a2-6)

The content of the monomer units that form a structural unit having an acid decomposable group is preferably 5 to 60 mol %, more preferably 10 to 50 mol %, and particularly preferably 10 to 40 mol %, with respect to the total monomer units that constitute the specific resin (A). When the content is within the above range, a photosensitive resin composition having a high sensitivity and a wide exposure latitude can be obtained.

Functional Group Capable of Forming a Covalent Bond by Reacting with Carboxyl Group or Phenolic Hydroxyl Group.

Examples of the functional group capable of forming a covalent bond by reacting with a carboxyl group or a phenolic hydroxyl group include an epoxy group, an oxetanyl group, an acid anhydride group, an acid halide group and an isocyanate group. A radical polymerizable monomer containing any of these functional groups is preferably used for synthesis of the specific resin (A). Among the functional groups, an epoxy group and/or an oxetanyl group are preferable.

The structural unit having an epoxy group and/or an oxetanyl group is preferably a structural unit having an alicyclic epoxy group and/or an oxetanyl group, and more preferably a structural unit having an oxetanyl group.

The alicyclic epoxy group is a group in which a condensed ring is formed from an aliphatic ring and an epoxy ring. Preferable specific examples of the alicyclic epoxy group include a 3,4-epoxycyclohexyl group, a 2,3-epoxycyclohexyl group and a 2,3-epoxycyclopentyl group.

The group containing an oxetanyl group is not specifically limited as long as it contains an oxetanyl ring, but a preferable example thereof is a (3-ethyloxetan-3-yl)methyl group.

The structural unit having an epoxy group and/or an oxetanyl group is not specifically limited as long as it has at least one epoxy or oxetanyl group. A single structural unit may contain one or more epoxy groups and one or more oxetanyl groups, two or more epoxy groups, or two or more oxetanyl groups without particular limitation, but the total number of the epoxy group and/or the oxetanyl group contained in the structural unit is preferably 1 to 3, more preferably 1 or 2, and still more preferably one epoxy group or one oxetanyl group.

In the chemical formulas regarding the structural units of the specific resin (A), a substituent that can be accepted by an alkyl group, a cycloalkyl group, an aromatic group and the like may be any substituent, as long as it is an inert substituent that does not negatively affect the composition or the cured film formation method according to the present invention. Specific examples of such a substituent include a lower alkoxy group having 1 to 4 carbon atoms, an acyl group having 2 to 5 carbon atoms, and a chlorine atom.

Specific examples of the radical polymerizable monomer used for forming a structural unit having an epoxy group include glycidyl acrylate, glycidyl methacrylate, glycidyl α-ethyl acrylate, glycidyl α-n-propyl acrylate, glycidyl α-n-butyl acrylate, 3,4-epoxybutyl acrylate, 3,4-epoxybutyl methacrylate, 6,7-epoxyheptyl acrylate, 6,7-epoxyheptyl methacrylate, 6,7-epoxyheptyl α-ethyl acrylate, o-vinyl benzyl glycidyl ether, m-vinyl benzyl glycidyl ether, p-vinyl benzyl glycidyl ether, and alicyclic epoxy skeleton-containing compounds described in paragraphs [0031] to [0035] of Japanese Patent No. 4168443.

Examples of the radical polymerizable monomer used for forming a structural unit having an oxetanyl group include (meth)acrylic acid esters containing an oxetanyl group described in paragraphs [0011] to [0016] of JP-A No. 2001-330953.

A preferable example of the radical polymerizable monomer is 1-ethyl-3-oxacyclobutyl-methyl(meth)acrylate.

Preferable examples of the radical polymerizable monomer used for forming a structural unit having at least one of an epoxy group or an oxetanyl group include a monomer having a methacrylic acid ester structure and a monomer having an acrylic acid ester structure.

Among those monomers, still more preferable monomers are the alicyclic epoxy skeleton-containing compounds described in paragraphs [0034] to [0035] of Japanese Patent No. 416844 and the oxetanyl group-containing (meth)acrylates described in paragraphs [0011] to [0016] of JP-A No. 2001-330953, in which the oxetanyl group-containing (meth)acrylate esters described therein are particularly preferable. Among them, preferred examples are 3,4-epoxycyclohexylmethyl acrylate, 3,4-epoxycyclohexyl-methyl methacrylate, (3-ethyloxetan-3-yl)methyl acrylate and (3-ethyloxetan-3-yl)methyl methacrylate, and most preferred are (3-ethyloxetan-3-yl)methyl acrylate and (3-ethyloxetan-3-yl)methyl methacrylate. These structural units can be used alone or as a combination of two or more kinds thereof.

Preferable specific examples of the structural unit having a functional group capable of forming a covalent bond by reacting with a carboxyl group or a phenolic hydroxyl group include the following structural units:

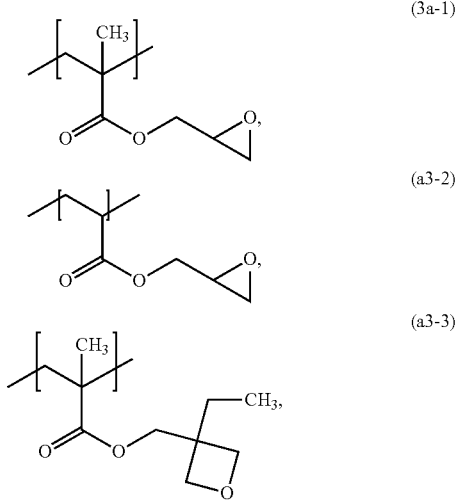

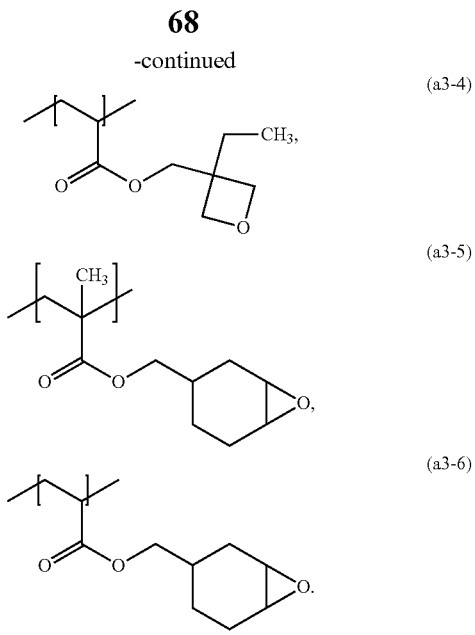

The content of monomer units that constitute a structural unit having a functional group capable of forming a covalent bond by reacting with a carboxyl group or a phenolic hydroxyl group is preferably 10 to 80 mol %, more preferably 15 to 70 mol %, and particularly preferably 20 to 65 mol %, with respect to the total monomer units that constitute the specific resin (A).

Among these structural units, an oxetanyl group-containing structural unit is particularly preferable in view of improving the preservation stability of the photosensitive resin composition.

The content ratio between the structural unit having an acid decomposable group and the structural unit having a functional group capable of forming a covalent bond by reacting with a carboxyl group or a phenolic hydroxyl group is preferably from 1:1 to 2:1 in terms of a molar ratio, in addition to satisfying the preferable contents thereof as mentioned above. When the content ratio is within the above range, sensitivity, exposure latitude and preservation stability may be improved at the same time.

Other Structural Units.

The specific resin (A) may include a further structural unit other than the above structural units. Exemplary radical polymerizable monomers that form a further structural unit include the compounds described in paragraphs [0021] to [0024] of JP-A No. 2004-264623.

Among them, from the viewpoint of improving the electrical characteristics, preferred are (meth)acrylates containing an alicyclic structure, such as dicyclopentanyl(meth)acrylate, cyclohexyl(meth)acrylate and cyclohexyl acrylate.

The specific resin (A) preferably includes, as a further structural unit, a structural unit derived from at least one compound selected from a group consisting of styrene derivatives, maleimide derivatives, (meth)acrylic acids and hydroxyl group-containing (meth)acrylate compounds.

Preferable styrene derivatives include styrene, chloromethyl styrene and acetoxystyrene.

Preferable maleimide derivatives include N-butylmaleimide and N-cyclohexyl maleimide.

Preferable hydroxyl group-containing (meth)acrylate compounds include hydroxyethyl(meth)acrylate, 2-hydroxypropyl(meth)acrylate, 3-hydroxypropyl(meth)acrylate and 4-hydroxybutyl(meth)acrylate.

The content of monomer units that constitute a further structural unit is preferably 0 to 50 mol %, more preferably 0 to 45 mol %, and particularly preferably 5 to 40 mol %, with respect to the total structural unit of the specific resin (A).

The weight average molecular weight of the specific resin (A) is preferably 1,000 to 100,000, and more preferably 2,000 to 50,000. The weight average molecular weight used in the insulation layer is preferably a weight average molecular weight in terms of polystyrene by gel permeation chromatography (GPC).

The following are preferable examples of the specific resin (A) together with the constituent monomers and the copolymerization ratio thereof shown in the parentheses.

However, the composition for forming an insulation layer is not limited to these examples.

The weight average molecular weight of the following examples of the specific resin (A) is preferably from 2,000 to 50,000.

1-ethoxyethyl methacrylate/tert-butyl methacrylate/glycidyl methacrylate copolymer (55/25/20)

1-ethoxyethyl methacrylate/tert-butyl methacrylate/glycidyl methacrylate/methacrylate copolymer (55/25/10/10);

1-ethoxyethyl methacrylate/tetrahydro-2H-pyran-2-yl methacrylate/glycidyl methacrylate/methacrylate copolymer (25/45/20/10);

1-ethoxyethyl methacrylate/tetrahydro-2H-furan-2-yl methacrylate/glycidyl methacrylate/methacrylate copolymer (35/35/15/15);

1-ethoxyethyl methacrylate/tert-butyl methacrylate/3,4-epoxycyclohexylmethyl methacrylate copolymer (35/40/25);

1-ethoxyethyl methacrylate/tert-butyl methacrylate/3,4-epoxycyclohexylmethyl methacrylate/methacrylate copolymer (40/15/25/20);

1-ethoxyethyl methacrylate/tert-butyl methacrylate/3,4-epoxycyclohexylmethyl methacrylate/(3-methacryloyloxy-2-hydroxypropyl)4-hydroxybenzoate copolymer (45/35/10/10);

1-ethoxyethyl methacrylate/tert-butyl methacrylate/3,4-epoxycyclohexylmethylmethacrylate/(3-methacryloyloxypropyl)4-hydroxybenzoate copolymer (40/30/10/10)

1-ethoxyethyl methacrylate/tert-butyl methacrylate/3,4-epoxycyclohexylmethyl methacrylate/(3-methacryboyloxy-propyl)4-hydroxybenzoate/2-hydroxyethyl methacrylate copolymer (30/20/20/15/15)

1-ethoxyethyl methacrylate/tert-butyl methacrylate/3,4-epoxycyclohexylmethyl methacrylate/(3-methacryloyloxypropyl)4-hydroxybenzoate/methyl methacrylate copolymer (40/15/15/15/15)

1-ethoxyethyl methacrylate/tetrahydro-2H-pyran-2-yl methacrylate/3,4-epoxycyclohexyl-methyl methacrylate/(3-methacryloyloxypropyl)4-hydroxybenzoate copolymer (20/30/20/30)

1-ethoxyethyl methacrylate/tetrahydro-2H-furan-2-yl methacrylate/3,4-epoxycyclohexyl-methyl methacrylate/(3-methacryloyloxypropyl)4-hydroxybenzoate copolymer (25/35/25/15)

1-ethoxyethyl methacrylate/tetrahydro-2H-pyran-2-yl methacrylate/3,4-epoxycyclohexyl-methyl methacrylate/(3-methacryloyloxypropyl)4-hydroxybenzoate/2-hydroxyethyl methacrylate copolymer (40/20/20/15/5)

1-ethoxyethyl methacrylate/tetrahydro-2H-furan-2-yl methacrylate/3,4-epoxycyclohexyl-methyl methacrylate/(3-methacryloyloxypropyl)4-hydroxybenzoate/2-hydroxyethyl methacrylate copolymer (35/20/20/15/10)

1-ethoxyethyl methacrylate/tert-butyl methacrylate/3,4-epoxycyclohexylmethyl acrylate/(3-methacryloyloxypropyl)4-hydroxybenzoate copolymer (25/25/25/25);

1-ethoxyethyl methacrylate/tert-butyl methacrylate/3,4-epoxycyclohexylmethyl acrylate/(3-methacryloyloxypropyl)4-hydroxybenzoate/2-hydroxyethyl methacrylate copolymer (20/35/20/15/10);

1-ethoxyethyl methacrylate/tert-butyl methacrylate/(3-ethyloxetan-3-yl)methyl methacrylate copolymer (45/25/30);

1-ethoxyethyl methacrylate/tert-butyl methacrylate/(3-ethyloxetan-3-yl)methyl methacrylate/methacrylate copolymer (25/25/35/15);

1-ethoxyethyl methacrylate/tert-butyl methacrylate/(3-ethyloxetan-3-yl)methyl methacrylate/(3-methacryloyloxy-2-hydroxypropyl)4-hydroxybenzoate copolymer (35/25/20/20);

1-ethoxyethyl methacrylate/tert-butyl methacrylate/(3-ethyloxetan-3-yl)methyl methacrylate/(3-methacryloyloxypropyl)4-hydroxybenzoate copolymer (35/25/20/20);

1-ethoxyethyl methacrylate/2-methyl-2-adamantyl methacrylate/(3-ethyloxetan-3-yl)methyl methacrylate/(3-methacryloyloxypropyl)4-hydroxybenzoate copolymer (25/25/25/25);

1-ethoxyethyl methacrylate/1-methyl-1-cyclohexyl methacrylate/(3-ethyloxetan-3-yl)methyl methacrylate/(3-methacryloyloxypropyl)4-hydroxybenzoate copolymer (15/50/15/20);

1-ethoxyethyl methacrylate/tert-butyl methacrylate/(3-ethyloxetan-3-yl)methyl methacrylate/(2-methacryloyloxyethyl)4-hydroxybenzoate copolymer (40/25/20/15);

1-ethoxyethyl methacrylate/tert-butyl methacrylate/(3-ethyloxetan-3-yl)methyl methacrylate/(6-methacryloyloxyhexyl)4-hydroxybenzoate copolymer (30/30/20/20);

1-ethoxyethyl methacrylate/tert-butyl methacrylate/(3-ethyloxetan-3-yl)methyl methacrylate/(3-methacryloyloxypropyl)4-hydroxybenzoate/2-hydroxyethyl methacrylate copolymer (20/20/25/25/10);

1-ethoxyethyl methacrylate/methacrylate/glycidyl methacrylate/2-hydroxyethylmethacrylate copolymer (30/10/40/20);

1-cyclohexyloxyethyl methacrylate/methacrylate/glycidyl methacrylate/2-hydroxyethyl methacrylate copolymer (40/10/30/20);

tetrahydro-2H-pyran-2-yl methacrylate/methacrylate/(3-ethyloxetan-3-yl)methyl methacrylate/2-hydroxyethyl methacrylate copolymer (30/10/40/20);

tetrahydro-2H-pyran-2-yl methacrylate/methacrylate/glycidyl methacrylate/2-hydroxyethyl methacrylate copolymer (30/10/40/20);

tetrahydro-2H-pyran-2-yl methacrylate/methacrylate/glycidyl methacrylate/styrene/2-hydroxyethyl methacrylate copolymer (30/10/40/15/5);

tetrahydrofuran-2-yl methacrylate/methacrylate/(3-ethyloxetan-3-yl)methyl methacrylate/2-hydroxyethyl methacrylate copolymer (40/10/30/20);

tetrahydrofuran-2-yl methacrylate/methacrylate/glycidyl methacrylate/2-hydroxyethyl methacrylate copolymer (41/9/30/20);

1-ethoxyethyl methacrylate/methacrylate/glycidyl methacrylate/2-hydroxyethyl methacrylate/cyclohexyl methacrylate copolymer (30/15/30/20/5);

1-ethoxyethyl methacrylate/methacrylate/glycidyl methacrylate/poly(ethylene glycolpropylene glycol)-monomethacrylate (BLEMMER 50PEP-300, trade name, manufactured by NOF Corp.)/dicyclopentanyl methacrylate copolymer (50/10/30/4/6);

1-ethoxyethyl methacrylate/methacrylate/glycidyl methacrylate/methoxypolyethylene glycol methacrylate (BLEMMER PME-400, trade name, manufactured by NOF Corp.) copolymer (46/4.5/48/1.5);

1-cyclohexyloxyethyl methacrylate/acrylate/glycidyl methacrylate/methoxypolyethylene-glycol methacrylate (BLEMMER PME-400, trade name, manufactured by NOF Corp.) copolymer (40/15/43/2);

1-cyclohexyloxyethyl methacrylate/methacrylate/glycidyl methacrylate/methoxypolyethylene glycol methacrylate (BLEMMER PME-400, trade name, manufactured by NOF Corp.)/dicyclopentanyl methacrylate copolymer (40/15/33/2/10);

tetrahydro-2H-pyran-2-yl methacrylate/methacrylate/glycidyl methacrylate/2-hydroxyethyl methacrylate copolymer (42/10/28/20);

1-ethoxyethyl methacrylate/methacrylate/(3-ethyloxetan-3-yl)methyl methacrylate/2-hydroxyethyl methacrylate copolymer (45/10/25/20).

The specific resin (A) may be used alone or as a combination of two or more kinds thereof. The content of the specific resin (A) in the photosensitive resin composition according to the present invention is preferably 20 to 99% by weight, more preferably 40 to 97% by weight, and still more preferably 60 to 95% by weight, with respect to the total solid content of the photosensitive resin composition. When the content of the specific resin (A) is within the above range, a favorable pattern can be formed upon development.

In the present specification, the solid content of the photosensitive resin composition refers to the total amount of the components other than a solvent.

The content of the resin other than the specific resin (A) is preferably smaller than that of the specific resin (A).

Photo-Sensitive Acid Generator (B):

The compounds of the formula (I) and (IA) as described above are used as the component (B) in the above mentioned formulation Sensitizer (C):

As the optional component (C), a sensitizer in the above formulation, the sensitizer compounds as described above are suitable.

In the positive photosensitive resin composition for insulating layer as described above, the content of the sensitizer (C) is preferably within a range from 0.1 to 10 parts by weight, more preferably within a range from 0.5 to 10 parts by weight, with respect to 100 parts by weight of the specific resin (A).

Solvent (D):

The positive photosensitive resin composition of the invention preferably includes (D) a solvent. Suitable are solvents as described above.

Other Additives:

In general, in a positive photosensitive resin composition, if necessary, the following known additives may be used as optional components: (E) an antioxidant, (F) a cross-linker, (G) an adhesion improving agent, (H) a basic compound, (L) a surfactant, (J) a plasticizer, (K) a thermal radical generator, a thermal acid generator, a UV absorbent, a thickener, an organic or inorganic suspending agent, and the like.

(E) Antioxidant:

The antioxidant (E) may be a known antioxidant, and addition of an antioxidant makes it possible to suppress coloring of a cured film in a more favorable manner. In addition, the amount of reduction in film thickness due to decomposition of a starting material or the like may be reduced, and heat-resistant transparency of the obtained cured film may be further improved.

Examples of the antioxidant that may be used in the present invention include phosphorus antioxidants, hydrazides, hindered amine antioxidants, sulfur antioxidants, phenol antioxidants, ascorbic acids, zinc sulfate, sugars, nitrites, sulfites, thiosulfates and hydroxylamine derivatives. Among them, phenol antioxidants are particularly preferable in terms of effectively suppressing coloring of a cured film and suppressing reduction in film thickness.

Phenol antioxidants are available also as commercial products, and examples thereof include ADEKASTUB AO-60, ADEKASTUB AO-80 (manufactured by ADEKA Co., Ltd.) and IRGANOX 1098 (manufactured by BASF Japan Ltd.)

The antioxidant (E) may be used alone or as a mixture of two or more kinds. The content of the antioxidant (E) is preferably within a range from 0.1 to 6% by weight, more preferably within a range from 0.2 to 5% by weight, and particularly preferably within a range from 0.5 to 4% by weight, with respect to the total solid content of the photosensitive resin composition.

In addition, as an additive other than the antioxidant (E), various UV absorbents described in "Kobunshi Tenkazai no Shin Tenkai (New Horizon of High Polymer Additives)", published by Nikkan Kogyo Shimbun Ltd., as well as the UV-absorbers as described above, metal inactivating agents or the like may be added to the photosensitive resin composition of the invention.

(F) Cross-Linker

Examples of the cross-linker (F) include a compound containing two or more epoxy groups or oxetanyl groups in a molecule, an alkoxymethyl-containing cross-linker and a compound containing at least one ethylenically unsaturated double bond.

Compounds Containing Two or More Epoxy or Oxetanyl Groups in the Molecule.

Specific examples of the compound containing two or more epoxy groups or oxetanyl groups in a molecule include bisphenol A epoxy resins, bisphenol F epoxy resins, phenol novolac epoxy resins, cresol novolac epoxy resins and aliphatic epoxy resins.

These compounds are commercially available. Examples of the bisphenol A epoxy resins include JER 827, JER 828, JER 834, JER 1001, JER 1002, JER 1003, JER 1055, JER 1007, JER 1009 and JER 1010 (all manufactured by Japan Epoxy Resins Co., Ltd.), EPICLON 860, EPICLON 1050, EPICLON 1051 and EPICLON 1055 (all manufactured by DIC Co. Ltd.); examples of the bisphenol F epoxy resins include JER 806, JER 807, JER 4004, JER 4005, JER 4007 and JER 4010 (all manufactured by Japan Epoxy Resins Co., Ltd.), EPICLON N-740, EPICLON N-770 and EPICLON N-775 (all manufactured by DIC Co. Ltd.); examples of the cresol novolac epoxy resins include EPICLON N-660, EPICLON N-665, EPICLON N-670, EPICLON N-673, EPICLON N-680, EPICLON N-690 and EPICLON N-695 (all manufactured by DIC Co. Ltd.) and EOCN-1020 (manufactured by Nippon Kayaku Co., Ltd.); and examples of aliphatic epoxy resins include ADEKA RESIN EP-4080S, ADEKA RESIN EP-4085S and ADEKA RESIN EP-4088S (manufactured by ADEKA Co., Ltd.), CELLOXIDE 2021P, CELLOXIDE 2081, CELLOXIDE 2083, CELLOXIDE 2085, EHPE 3150, EPOLEAD PB 3600 and EPOLEAD PB 4700 (manufactured by Daicel Chemical Industries, Ltd.) In addition to these examples, ADEKA RESIN EP-4000S, ADEKA RESIN EP-4003S, ADEKA RESIN EP-4010S, ADEKA RESIN EP-4011S, NC-2000, NC-3000, NC-7300, XD-1000, EPPN-501, EPPN-502 (manufactured by ADEKA Co., Ltd.) are also usable. These products may be used alone or as a combination of two or more kinds thereof.

Among them, preferred are bisphenol A epoxy resins, bisphenol F epoxy resins and phenol novolac epoxy resins. Particularly preferred is bisphenol A epoxy resins.

Specific examples of the compound containing two or more oxetanyl groups in a molecule include ARON OXETANE OXT-121, OXT-221, OX-SQ and PNOX (manufactured by Toagosei Co., Ltd.).

The oxetanyl group-containing compounds may be used alone or as a mixture with an epoxy group-containing compound.

The amount of the compound containing two or more epoxy groups or oxetanyl groups in a molecule in the photosensitive resin composition is preferably within a range from 1 to 50 parts by weight, and more preferably within a range from 3 to 30 parts by weight, with respect to 100 parts by weight of the total amount of the specific resin (A).

Alkoxymethyl Group-Containing Cross-Linker:

Preferable examples of the cross-linkers containing an alkoxymethyl group include alkoxymethylated melamine, alkoxymethylated benzoguanamine, alkoxymethylated glycoluril and alkoxymethylated urea. These compounds may be obtained by substituting a methylol group of methylolated melamine, methylolated benzoguanamine, methylolated glycoluril or methylolated urea with an alkoxymethyl group. The type of the alkoxymethyl group is not particularly limited, and examples thereof include a methoxymethyl group, an ethoxymethyl group, a propoxymethyl group and a butoxymethyl group. From the viewpoint of the amount of outgas generation, a butoxymethyl group is particularly preferable.

Among these cross-linking compounds, preferred are alkoxymethylated melamine, alkoxymethylated benzoguanamine and alkoxymethylated glycoluril. From the viewpoint of transparency, alkoxymethylated glycoluril is particularly preferable.

These alkoxymethyl group-containing cross-linkers are commercially available, and preferred examples thereof include CYMEL 300, 301, 303, 370, 325, 327, 701, 266, 267, 238, 1141, 272, 202, 1156, 1158, 1123, 1170, 1174, UFR 65, 300 (all manufactured by Mitsui Cyanamid Co., Ltd.), NIKALAC MX-750, -032, -706, -708, -40, -31, 270, -280, -290, NIKALAC MS-11, NIKALAC MW-30 HM, -100 LM, and -390 (all manufactured by Sanwa Chemical Co., Ltd.)

In the photosensitive resin composition, the content of the alkoxymethyl group-containing cross-linker is preferably within a range form 0.05 to 50 parts by weight, and more preferably within a range from 0.5 to 10 parts by weight, with respect to 100 parts by weight of the specific resin (A).

(G) Adhesion Improving Agent:

Examples of (G) an adhesion improving agent are inorganic substance as a base material, for example, silicon compounds such as silicon, silicon oxide and silicon nitride, and compounds that improve the adhesion between a dielectric film and a metal such as gold, copper or aluminum. Specific examples of the adhesion improving agent include silane coupling agents and thiol-based compounds. A silane coupling agent, which is used in the invention as an adhesion improving agent, provides modification of an interface and may be selected from known compounds without particular limitation. Preferable examples of the silane coupling agent include γ-aminopropyltrimethoxysilane, γ-aminopropyltriethoxysilane, γ-glycidoxypropyl trialkoxysilane, γ-glycidoxypropylalkyldialkoxysilane, γ-methacryloxypropyl trialkoxysilane, γ-methacryloxypropyl alkyldialkoxysilane, γ-chloropropyl trialkoxysilane, γ-mercaptopropyl trialkoxysilane, β-(3,4-epoxycyclohexyl)ethyltrialkoxysilane and vinyltrialkoxysilane.

Among them, γ-glycidoxypropyl trialkoxysilane and γ-methacryloxypropyl trialkoxysilane are more preferable, and γ-glycidoxypropyl trialkoxysilane is still more preferable.

These compounds may be used as alone or as a combination of two or more kinds thereof. These compounds are effective in terms of improving the adhesion to a substrate, and also adjusting a taper angle with respect to the substrate.

In the photosensitive resin composition of the present invention, the content of the component G is preferably within a range from 0.1 to 20 parts by weight and more preferably within a range from 0.5 to 10 parts by weight, with respect to 100 parts by weight of the specific resin (A).

(H) Basic Compound:

The basic compound may be selected from compounds used in chemically amplified resist materials. Examples of the basic compound include aliphatic amines, aromatic amines, heterocyclic amines, quaternary ammonium hydroxides and quaternary ammonium salts of carboxylic acid.

Specific examples of the basic compound include compounds described in paragraphs [0052] to [0056] of JP-A No. 2009-98616.

The basic compound that can be used in the present invention may be used alone or as a combination of two or more kinds, but a combination of two kinds is preferred, and a combination of two kinds of heterocyclic amines is more preferred.

The content of the basic compound (H) in the photosensitive resin composition is preferably within a range from 0.001 to 1.0 parts by weight, and more preferably within a range from 0.005 to 0.2 parts by weight, with respect to 100 parts by weight of the specific resin (A).

(L) Surfactant:

The surfactant may be anionic, cationic, nonionic or amphoteric, but nonionic surfactants are preferred.

Examples of the surfactant include polyoxyethylene higher alkylethers, polyoxyethylene higher alkylphenyl ethers, polyethylene glycol higher fatty acid diesters, silicones and fluorosurfactants. Examples of commercially available products include KP (trade name, manufactured by Shin-Etsu Chemical Co., Ltd.), POLYFLOW (trade name, Kyoeisya Chemical Co., Ltd.), FTOP (trade name, manufactured by JEMCO Inc.), MEGAFAC (tradename, manufactured by DIC Co., Ltd.), FLUORAD (trade name, manufactured by Sumitomo 3M Limited), ASAHIGUARD and SURFLON (trade names, manufactured by Asahi Glass Co., Ltd.) and POLYFOX (trade name, manufactured by OMNOVA Co., Ltd.).

The weight average molecular weight (Mw) of the copolymer used as a surfactant preferably within a range from 1,500 to 5,000.

The surfactants may be used alone or as a mixture of two or more kinds thereof.

The amount of the surfactant (L) in the photosensitive resin composition is preferably 10 or less parts by weight, more preferably 0.01 to 10 parts by weight, and still more preferably 0.01 to 1 parts by weight, with respect to 100 parts by weight of the specific resin (A).

(J) Plasticizer.

Examples of the plasticizer include dibutyl phthalate, dioctyl phthalate, didodecyl phthalate, polyethylene glycol, glycerin, dimethyl glycerin phthalate, dibutyl tartrate, dioctyl adipate and triacetyl glycerin.

The amount of the plasticizer (J) in the photosensitive resin composition is preferably within a range from 0.1 to 30 parts by weight, and more preferably within a range from 1 to 10 parts by weight, with respect to 100 parts by weight of the specific resin (A).

(K) Thermal Radical Generator:

The photosensitive resin composition may include (K) a thermal radical generator. When the photosensitive resin composition thereof contains an ethylenically unsaturated compound, such as a compound containing at least one ethylenically unsaturated double bond, the composition preferably contains a thermal radical generator (K).

A thermal radical generator is a compound that generates radicals by thermal energy, and initiates or promotes polymerization reaction of a polymerizable compound. Addition of a thermal radical generator may increase the strength of a cured film, thereby improving the thermal resistance and solvent resistance.

Preferable examples of the thermal radical generator include aromatic ketones, onium salt compounds, organic peroxides, thio compounds, hexaaryl biimidazole compounds, ketoxime ester compounds, borate compounds, azinium compounds, metallocene compounds, active ester compounds, compounds containing a carbon-halogen bond, azo-based compounds and bibenzyl compounds.

Further examples of thermal radical initiators are disclosed in U.S. Pat. No. 6,929,896, WO 2010057922, WO2012113829, WO2012101245, WO2013156509 or WO2014064064.

The thermal radical generator may be used alone or as a combination of two or more kinds.

The amount of the thermal radical generator (K) in the photosensitive generator of the present invention is preferably within a range from 0.01 to 50 parts by weight, more preferably within a range from 0.1 to 20 parts by weight, and most preferably within a range from 0.5 to 10 parts by weight, with respect to 100 parts by weight of the specific resin (A), from the viewpoint of improving the film properties.

Method for Preparing A Photosensitive Resin Composition:

The photosensitive resin composition may be prepared by, for example, mixing a specific resin (A), a specific acid generator (B) of the formula (I) or (IA), a sensitizer (C) and optional components at a given ratio, and dissolving these components by stirring. More specifically, for example, the resin composition may be prepared by preparing solutions each containing components (A) to (C) dissolved in a solvent (D), and then mixing these solutions at a given ratio.

The composition solution thus prepared may optionally be filtered before use.

Method for Forming a Cured Film:

The method for forming a cured film according to the present invention includes the following steps (1) to (5):

Step (1) applying the positive photosensitive resin composition of the present invention onto a substrate;

Step (2) removing the solvent from the applied positive photosensitive resin composition;

Step (3) exposing the positive photosensitive resin composition to actinic rays;

Step (4) developing the exposed positive photosensitive resin composition with an aqueous developer; and Step (5) carrying out post-baking to cure the positive photosensitive resin composition by heat.

In step (1), the positive photosensitive resin composition of the present invention is applied onto a substrate to form a wet film containing a solvent.

In step (2), the solvent is removed from the applied film by pressure reduction (vacuuming) and/or heating, and a dried photosensitive resin composition layer (film) is formed on the substrate.

In step (3), actinic rays having a wavelength of 300 to 450 nm is applied onto the obtained coating film. In this step, the specific acid generator (B) of the formula (I) or (IA) decomposes and generates acid. By means of catalytic action of the generated acid, hydrolysis of an acid decomposable group contained in the specific resin (A) is caused and a carboxyl group and/or a phenolic hydroxyl group is generated.

As necessary, the region in which an acid catalyst is generated may be subjected to post exposure baking (hereinafter, also referred to as PEB) in order to accelerate the hydrolysis. By performing PEB, generation of carboxyl groups from acid decomposable groups may be accelerated.

In the present invention, since the acid decomposable group in the specific resin (A) has a low activation energy of decomposition by acid, the acid decomposable group easily decomposes due to acid derived from the acid generator and generate a carboxyl group. Accordingly, in the present invention, a positive image can be formed by development without performing PEB.

Further, by performing PEB at a relatively low temperature, hydrolysis of the acid decomposable group can be accelerated without causing cross-linking reaction. The temperature for performing PEB is preferably from 30° C. to 130° C., more preferably from 40° C. to 100° C., and particularly preferably from 60° C. to 90° C.

In step (4), the polymer containing free carboxyl groups is developed with an alkali developer. By removing an exposed region containing the resin composition having a carboxyl group, which dissolves readily in the alkali developer, a positive image can be formed.

In step (5), by heating the obtained positive image, a cured film is formed by heating the positive image to allow the acid decomposable group in the specific resin (A) to thermally decompose to generate a carboxyl group, and allow the carboxyl group to cross-link with an epoxy group and/or an oxetanyl group. The heating temperature is preferably 150° C. or higher, more preferably from 180° C. to 250° C., and particularly preferably from 200° C. to 250° C. The time for heating can be appropriately determined depending on the heating temperature and the like, but is preferably within a range from 10 to 90 minutes.

By adding a step of exposing the entire region of developed pattern to actinic rays, preferably ultraviolet rays, prior to the post-baking, the cross-linking reaction can be promoted by acid generated during the actinic ray irradiation.

Method for Preparing a Photosensitive Resin Composition:

The method for preparing the photosensitive resin composition used to form a cured film is as described above. The amount of the solvent (D) may be adjusted in consideration of the thickness of the photosensitive resin composition layer to be formed. In addition, a surfactant or the like may be used for the purpose of improving the surface properties of the coated film.

Application Step and Solvent Removal Step:

A dried film is obtained by applying the resin composition onto a substrate and removing the solvent by pressure reduction and/or heating (pre-baking). Examples of the substrate include, in the case of manufacturing of a liquid crystal display device, a glass plate provided with a polarizing plate, optionally a black matrix layer and a color filter layer, and a transparent conductive circuit layer. The application method of the resin composition is not specifically limited, and examples thereof include slit coating, spray coating, roll coating and spin coating. Among them, slit coating is preferable in view of suitability for a large-size substrate. In the present specification, the large-size substrate refers to a substrate having a size of 1 m or more at each side.

The heating conditions at step (2), in which the solvent is removed, are determined such that the acid decomposable group in the specific resin (A) in an unexposed portion do not decompose to render the specific resin (A) soluble in an alkali developer, and may vary depending on the type or the composition ratio of the components. The heating conditions are preferably approximately 70° C. to 120° C. and approximately from 30 to 120 seconds.

Exposure Step:

At the exposure step, the coated film is exposed to actinic rays via a mask having a predetermined pattern. It is preferred to use actinic rays having a wavelength of 300 to 450 nm. After the exposure, heating (PEB) is performed, as necessary.

The exposure may be performed by using a low pressure mercury lamp, a high pressure mercury lamp, a chemical lamp, a laser beam generating apparatus and the like.

When a mercury lamp is used, actinic rays having a wavelength of g line (436 nm), i line (365 nm), h line (405 nm) or the like are preferably used. A mercury lamp is preferable as compared with lasers, since it is suitable for exposing a large area.

In the case of using lasers, solid-state (YAG) laser of 343 or 355 nm, excimer laser of 351 nm (XeF), and semiconductor laser of 375 or 405 nm may be used. Among them, 355 nm and 405 nm are preferable in terms of stability, costs and the like. Irradiation with laser may be performed on the coating film once or plural times.

The energy density per pulse of laser is preferably from 0.1 to 10,000 $mJ/cm^2$. In order to sufficiently cure the coating film, 0.3 $mJ/cm^2$ or more is more preferable and 0.5 $mJ/cm^2$ or more is most preferable. In order to prevent decomposition of the coating film due to ablation, 1,000 $mJ/cm^2$ or less is more preferable and 100 $mJ/cm^2$ or less is most preferable.

The pulse width is preferably from 0.1 nsec to 30.000 nsec. In order to prevent decomposition of a colored coating film due to ablasion, 0.5 nsec or more is preferable, and 1 nsec or more is most preferable. In order to improve the alignment precision of scanning exposure, 1,000 nsec or less is more preferable and 50 nsec or less is most preferable.

Furthermore, the frequency of laser is preferably from 1 to 50,000 Hz, and more preferably 10 to 1,000 Hz. When the laser frequency is lower than 1 Hz, the exposure time may be prolonged, whereas when the laser frequency is higher than 50,000 Hz, the alignment precision upon scanning exposure may be lowered.

In order to shorten the exposure time, 10 Hz or higher is more preferable and 100 Hz or higher is most preferable. In order to improve the alignment precision upon scanning exposure, 10,000 Hz or lower is more preferable and 1,000 Hz or lower is most preferable.

Lasers have an advantage over mercury lamps in that lasers are easier to focus the beam, which leads to cost reduction as a result of omitting a mask for pattern formation during exposure.

Furthermore, as necessary, the exposure light may be adjusted through a spectral filter such as a short pass filter, a long pass filter or a band pass filter.

Development Step:

In the development step, an image pattern is formed by removing the exposed region with a basic developer. Examples of the basic compound include alkali metal hydroxides such as lithium hydroxide, sodium hydroxide and potassium hydroxide; alkali metal carbonate salts such as sodium carbonate and potassium carbonate; alkali metal bicarbonates such as sodium bicarbonate and potassium bicarbonate; ammonium hydroxides such as tetramethylammonium hydroxide, tetraethylammonium hydroxide and choline hydroxide; and aqueous solutions such as sodium silicate and sodium metasilicate. It is also possible to use an aqueous solution prepared by adding an appropriate amount of aqueous organic solvent such as methanol or ethanol, or a surfactant, to an aqueous solution of alkali compounds as mentioned above.

The pH of the developer is preferably from 10.0 to 14.0.

The development time is preferably from 30 to 180 seconds, and the development method may be any of a puddle method, a dipping method or the like. After the development, the pattern is rinsed with running water for 30 to 90 seconds, thereby obtaining a desired pattern.

Post-Baking Step (Cross-Linking Step)

The pattern obtained by the development, which is formed from the unexposed region, is heated with a heater such as a hot plate or an oven at a temperature of, for example, from 180° C. to 250° C. The time period is, for example, from 5 to 60 minutes on a hot plate, or from 30 to 90 minutes in an oven. By heating the pattern, the acid decomposable group in the specific resin (A) is decomposed to generate a carboxyl group and/or a phenolic hydroxyl group, and the carboxyl group and/or the phenolic hydroxyl group reacts with the above-mentioned functional group in the specific resin (A) to cause cross-linking reaction, thereby allowing for formation of a protection film or an interlayer dielectric film having excellent thermal resistance, hardness and the like. In addition, transparency may also be improved by performing the heating under a nitrogen atmosphere.

Prior to the heating, it is preferable to perform re-exposure of the substrate on which a pattern has been formed with actinic rays, and subsequently perform post-baking, in order to generate acid from the component (B) existing in the unexposed region and utilize the acid as a catalyst for promoting the cross-linking reaction.

In other words, the method for forming a cured film according to the present invention preferably includes a step of performing re-exposure with actinic rays between the development and the post-baking.

The exposure in the re-exposure step may be performed in a similar manner to the exposure step as mentioned above. The re-exposure is preferably performed with respect to the entire surface of a side of the substrate on which a film is formed from the photosensitive resin composition of the present invention. The exposure amount at the re-exposure step is preferably from 50 to 1,000 $mJ/cm^2$.

With the photosensitive resin composition of the present invention, an interlayer dielectric film having excellent insulation properties and having high transparency, even when it is baked at high temperature, can be obtained. The interlayer dielectric film made of the photosensitive resin composition according to the present invention exhibits high transparency and excellent physical properties of a cured film. Therefore, the dielectric film is useful for organic EL display devices and liquid crystal display devices.

The structure of organic electronic (EL) display devices and liquid crystal display devices according to the present invention are not specifically limited as long as these display devices include a planarization film or an interlayer dielectric film formed from the photosensitive resin composition of the present invention, and any known devices having various structures are within the scope of the invention.

The following are exemplary embodiments of the invention. However, the invention is not limited to these embodiments:

A positive photosensitive resin composition comprising:
a resin (A) comprising a structural unit having an acid dissociative group and a structural unit having a functional group capable of forming a covalent bond by reacting with a carboxyl group or a phenolic hydroxyl group; and
an acid generator (B) represented by the formula (I) or (IA) as described above.

Interesting is the positive photosensitive resin composition as described above, wherein the acid generator is represented by formula (IA).

The positive photosensitive resin composition as described above, further comprising a sensitizer, for example selected from the group consisting of an anthracene derivative, an acridone derivative, a thioxanthone derivative, a coumarin derivative, a base styryl derivative and a distyrylbenzene derivative.

Also of interest is the positive photosensitive resin composition as described above, wherein the resin (A) further comprises at least one structural unit derived from a compound selected from the group consisting of a styrene derivative, a maleimide derivative, (meth)acrylic acid and a hydroxyl group-containing (meth)acrylate; as well as the positive photosensitive resin composition, wherein the functional group capable of forming a covalent bond by reacting with a carboxyl group or a phenolic hydroxyl group is at least one selected from an epoxy group and an oxetanyl group; in particular the positive photosensitive resin composition, wherein the functional group capable of forming a covalent bond by reacting with a carboxyl group or a phenolic hydroxyl group is an oxetanyl group.

Interesting further is a method for forming a cured film, the method comprising
(1) applying the positive photosensitive resin composition as described above onto a substrate to form a photosensitive resin composition layer;
2) removing a solvent from the photosensitive resin composition layer;
(3) exposing the positive photosensitive resin composition from which the solvent has been removed to actinic rays in a patterned manner;
(4) developing the exposed positive photosensitive resin composition with an aqueous developer; and
(5) curing the developed photosensitive resin composition layer after being developed by heating.

Further interesting is a cured film formed by the method as described above as well as an interlayer dielectric film formed from the cured film, an organic EL display device comprising the cured film and a liquid crystal display device comprising the cured film.

The examples which follow illustrate the invention in more detail, without restriciting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

Preparation of OS1 (not Representative for the Claims)

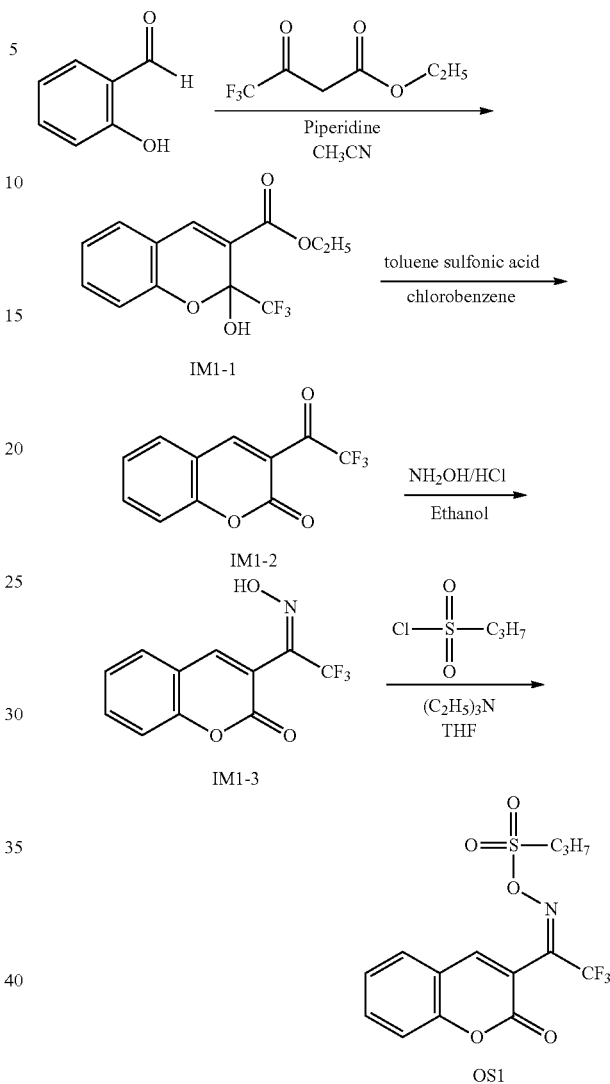

1.1: To 3.00 g of salicylaldehyde and 4.52 g of 4,4,4-ethyl trifluoroacetoacetate in acetonitrile (50 ml) are added 115 mg of piperidine and stirred under reflux for 21 hours. The reaction mixture is cooled to room temperature and water is added. The precipitate is collected by filtration and dried under vacuo, giving 4.68 g of IM1-1 as white solid.

1.2: To 4.60 g of IM1-1 in chlorobenzene (32 ml) is added 342 mg of p-toluenesulfonic acid monohydrate and stirred under reflux for 17 hours. The solvent is removed by evaporation and toluene (30 ml) and water are added to the mixture. The organic layer is separated from the aq. layer. The solution is refluxed for 3 hours and the resulting water is removed by Dean-Stark trap. After cooling to room temperature the reaction mixture is concentrated. The resulting solid is recrystallized from a mixture of dichloromethane and hexane, giving 2.3 g of IM1-2 as white solid.

1.3: To 508 mg of IM1-2 in ethanol (5 ml) is added 176 mg of hydroxyl ammonium chloride and refluxed for 22 hours. After cooling to room temperature, water is added to the reaction mixture. The precipitate is collected by filtration and dried under vacuo, giving 383 mg of IM1-3 as white solid.

1.4: To 303 mg of IM1-3 in tetrahydrofurane (THF) (5 ml) are added 203 mg of n-propanesulfonyl chloride and 168 mg of triethylamine at 0° C. After stirring for 2.5 hours, water is added to the mixture. The precipitate is collected by filtration and dried, giving 350 mg of OS1 as white solid. The physical data are collected in table 1 below.

Preparation of OS2 (not Representative for the Claims)

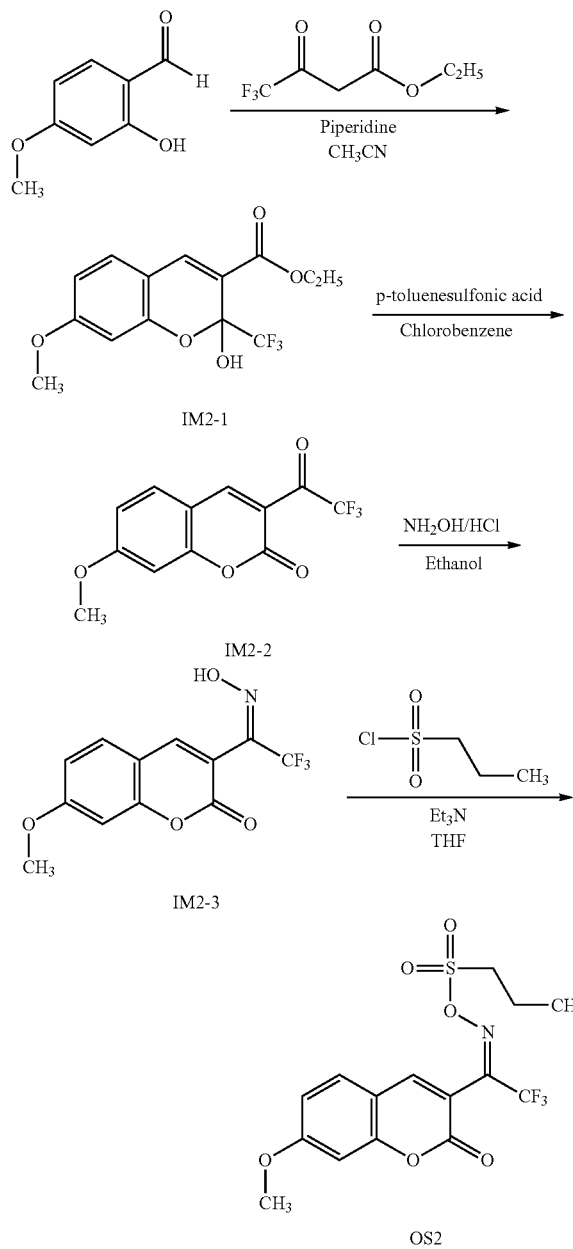

2.1: To 4.40 g of 4-methoxysalicylaldehyde and 6.45 g of 4,4,4-ethyl trifluoroacetoacetate in ace-tonitrile (60 ml) are added 275 mg of piperidine and stirred under reflux for 31 hours. The reaction mixture is cooled to room temperature and water and dichloro-methane are added. The organic solvent is collected and dried under vacuo, giving IM2-1 as yellow resin. IM2-1 is used to the next step without purification. 2.2: To IM2-1 in chlorobenzene (60 ml) is added 600 mg of p-toluenesulfonic anhydride and stirred under reflux for 22 hours. The solvent is removed by evaporation and toluene (30 ml) and water are added to the mixture. The organic layer is separated from the aq. layer. The solution is refluxed for 3 hours and the resulting water is removed by Dean-Stark trap. After cooling to room temperature the reaction mixture is concentrated. The resulting solid is recrystallized from a mixture of dichloromethane and hexane, giving 4.32 g of IM2-2 as white solid.

2.3: To 2.00 g of IM2-2 in ethanol (15 ml) is added 660 mg of hydroxyl ammonium chloride and refluxed for 19 hours. After cooling to room temperature, water is added to the reaction mixture. The precipitate is collected by filtration and dried under vacuo, giving 1.17 g of IM2-3 as white solid.

2.4: To 1.01 g of IM2-3 in THF (20 ml) are added 1.10 g of n-propanesulfonyl chloride and 600 mg of triethylamine at 0° C. After stirring for 15 hours, water is added to the mixture. The reaction mixture is added 20 mL of ethyl acetate, and washed with water. Organic layer is concentrated and purified by silicagel column chromatography with hexane and dichloromethane as eluent. 1.15 g of OS2 is obtained as white solid. The physical data are collected in table 1 below.

Preparation of OS3 (not Representative for the Claims)

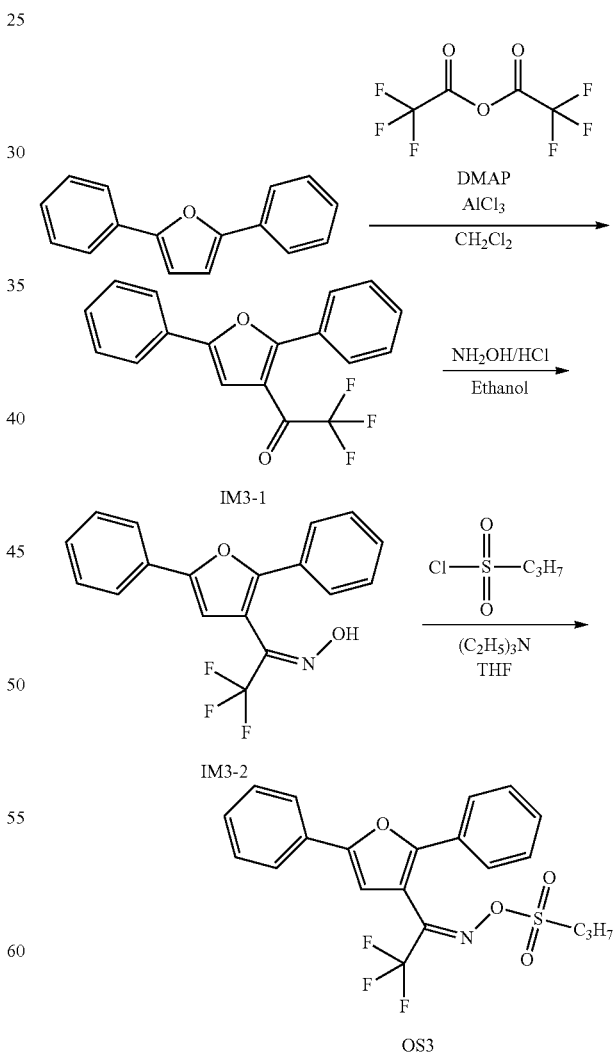

3.1: To 920 mg of 2,5-diphenylfuran, 627 mg of 4,4'-dimethylaminopyridine (DMAP) and 1.77 g of aluminum trichloride in dichloromethane (20 ml) are added 1.12 g of trifluoroacetic anhydride at 0° C. and stirred for 4 days at room temperature. The reaction mixture is added 30 mL of dichloromethane, and washed with water. Organic layer is concentrated and purified by silicagel column chromatography with hexane and dichloro-methane as eluent. 385 mg of IM3-1 is obtained as yellow solid.

3.2: To 385 mg of IM3-1 in ethanol (5 ml) is added 252 mg of hydroxyl ammonium chloride and refluxed for 2 hours. After cooling to room temperature, water is added to the reaction mixture, and extracted with ethyl acetate. Organic layer is dried with MgSO$_4$, and filtered. After evaporation of solvent, 387 mg of IM3-2 is obtained as yellow solid. 3.3: To 387 mg of IM3-2 in THF (10 ml) are added 171 mg of n-propanesulfonyl chloride and 217 mg of triethylamine at 0° C. and stirred for 4 hours. The reaction mixture is added 10 mL of ethyl acetate, and washed with water. Organic layer is concentrated and purified by silicagel column chromatography with hexane and dichloromethane as eluent. 150 mg of OS3 is obtained as white solid. The physical data are collected in table 1 below.

Preparation of OS4

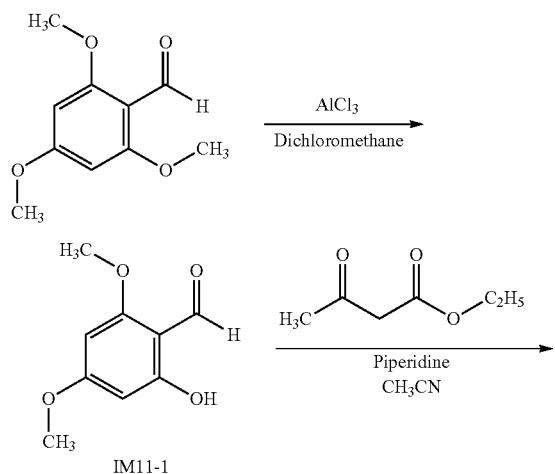

(not representative for the claims)

The compound OS4 is prepared in analogy to the compound OS2 employing the appropriate intermediates. The physical data are collected in table 1 below.

Preparation of OS11: (not Representative for the Claims)

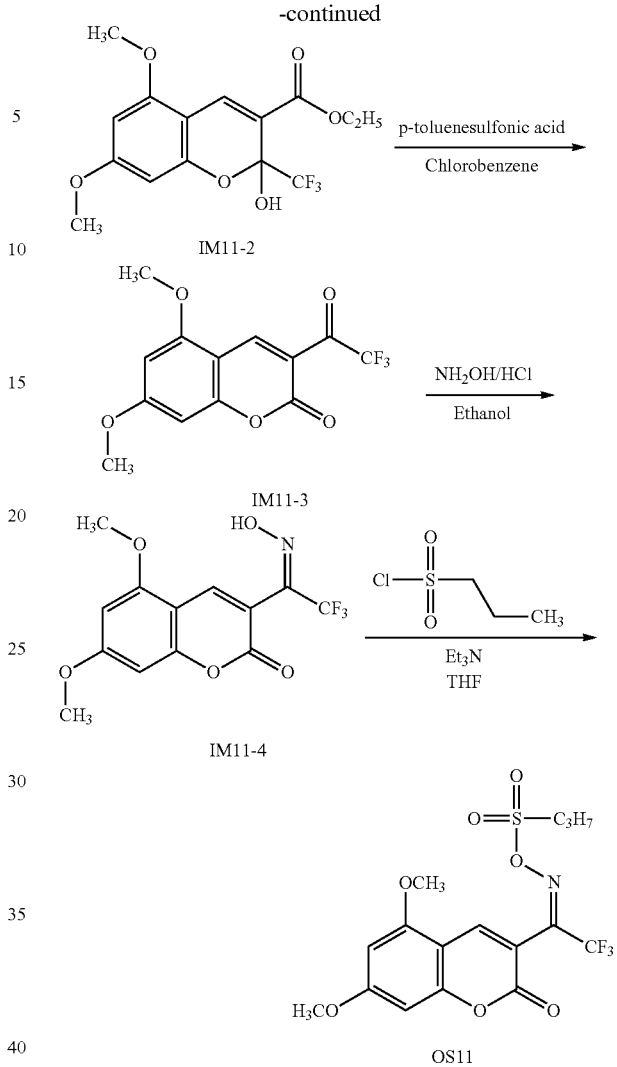

11.1: To 5.18 g of 2,4,6-trimethoxybenzaldehyde in dichlorimethane (60 ml) are added 4.04 g of aluminum chloride and stirred under reflux for 21 hours. The reaction mixture is cooled to room temperature and water and dichloro-methane are added. The organic solvent is collected and the resulting solid is recrystallized from a mixture of dichloro-methane and hexane, giving 3.66 g of IM11-1 as white solid.

11.2: To 3.66 g of IM11-1 and 4.74 g of 4,4,4-ethyl trifluoroacetoace-tate in ace-tonitrile (60 ml) are added 275 mg of piperidine and stirred under reflux for 31 hours. The reaction mixture is cooled to room temperature and water and dichloro-methane are added.

The organic solvent is collected and dried under vacuo, giving 6.46 g of IM11-2 as yellow solid. IM11-2 is used to the next step without purification.

11.3: To 6.46 g of IM11-2 in chlorobenzene (60 ml) is added 1000 mg of p-toluenesulfonic acid and stirred under reflux for 22 hours. The solvent is removed by evapora-tion and toluene (30 ml) and water are added to the mixture. The organic layer is sepa-rated from the aq. layer. The solution is refluxed for 3 hours and the resulting water is removed by Dean-Stark trap. After cooling to room temperature the reaction mixture is concentrated. The resulting solid is recrystallized from a mixture of dichloro-methane and hexane, giving 4.772 g of IM11-3 as yellow solid.

11.4: To 4.77 g of IM11-3 in ethanol (15 ml) is added 1.50 g of hydroxyl ammonium chloride and refluxed for 19 hours. After cooling to room temperature, water is added to the reaction mixture. The precipitate is collected by filtration and dried under vacuo, giving 4.46 g of IM11-4 as yellow solid.

11.5: To 1.51 g of IM11-4 in THF (20 ml) are added 0.82 g of n-propanesulfonyl chloride and 0.61 g of triethylamine at 0° C. After stirring for 15 hours, water is added to the mixture. The reaction mixture is added 20 mL of ethyl acetate, and washed with wa-ter. Organic layer is concentrated and purified by silicagel column chromatography with hexane and dichloromethane as eluent. 1.42 g of OS11 is obtained as yellow solid.

Preparation of OS16

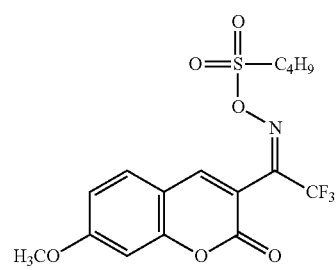

OS16

(not representative for the claims)

OS16 is prepared according to the same procedure as OS2, except using n-butanesulfonyl chloride instead of n-propanesulfonyl chloride.

Preparation of OS17

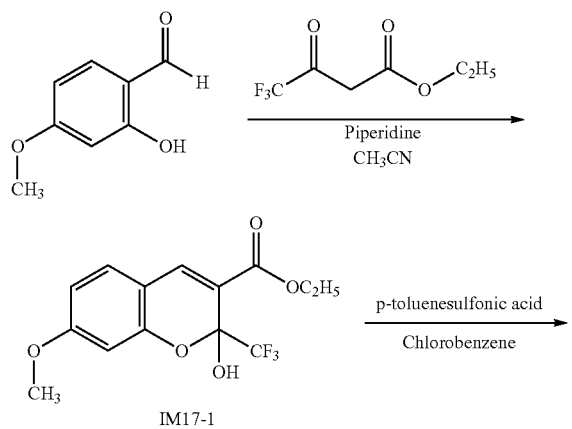

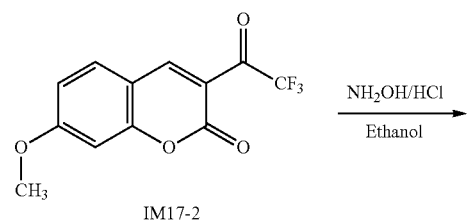

IM17-2

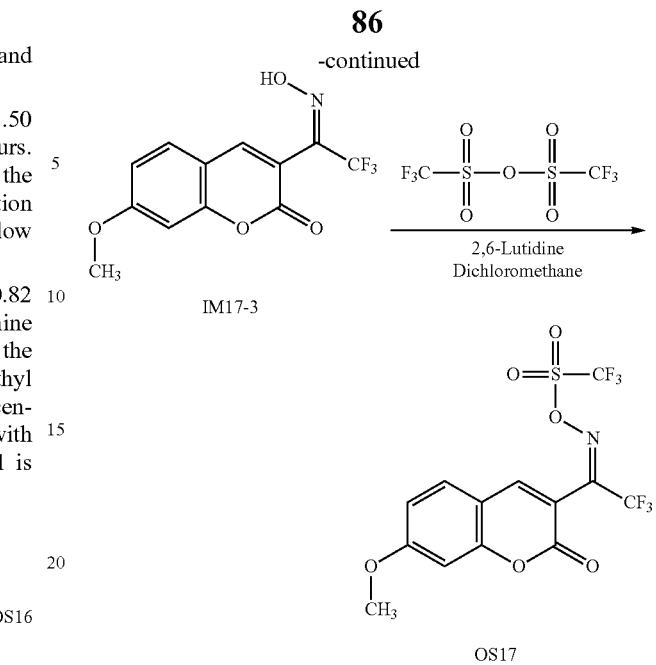

IM17-3

OS17

17.1: To 4.40 g of 4-methoxysalicylaldehyde and 6.45 g of 4,4,4-ethyl trifluoroacetoacetate in ethanol (60 ml) are added 275 mg of piperidine and stirred under reflux for 31 hours. The reaction mixture is cooled to room temperature and water and dichloro-methane are added. The organic solvent is collected and dried under vacuo, giving IM17-1 as yellow resin. IM17-1 is used to the next step without purification.

17.2: To IM17-1 in chlorobenzene (60 ml) is added 600 mg of p-toluenesulfonic anhydride and stirred under reflux for 22 hours. The solvent is removed by evapora-tion and toluene (30 ml) and water are added to the mixture. The organic layer is sepa-rated from the aq. layer. The solution is refluxed for 3 hours and the resulting water is removed by Dean-Stark trap. After cooling to room temperature the reaction mixture is concentrated. The resulting solid is recrystallized from a mixture of dichloro-methane and hexane, giving 4.32 g of IM17-2 as white solid.

17.3: To 2.00 g of IM17-2 in ethanol (15 ml) is added 660 mg of hydroxyl ammonium chloride and refluxed for 19 hours. After cooling to room temperature, water is added to the reaction mixture. The precipitate is collected by filtration and dried under vacuo, giving 1.17 g of IM17-3 as white solid.

17.4: To 1.01 g of IM17-3 in dichloromethane (20 ml) are added 1.10 g of trifluoromethanesulfonic anhydride and 554 mg of 2,6-lutidine at 0° C. After stirring for 15 hours, water is added to the mixture. The reaction mixture is added 20 mL of ethyl acetate, and washed with wa-ter. Organic layer is concentrated and purified by silicagel column chromatography with hexane and dichloromethane as eluent. 1.15 g of OS17 is obtained as white solid.

Preparation of OS24 (not Representative for the Claims)

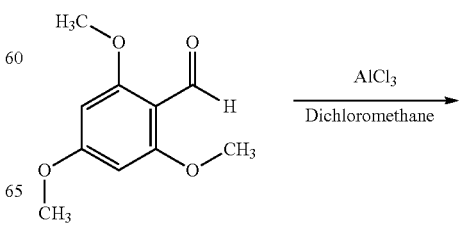

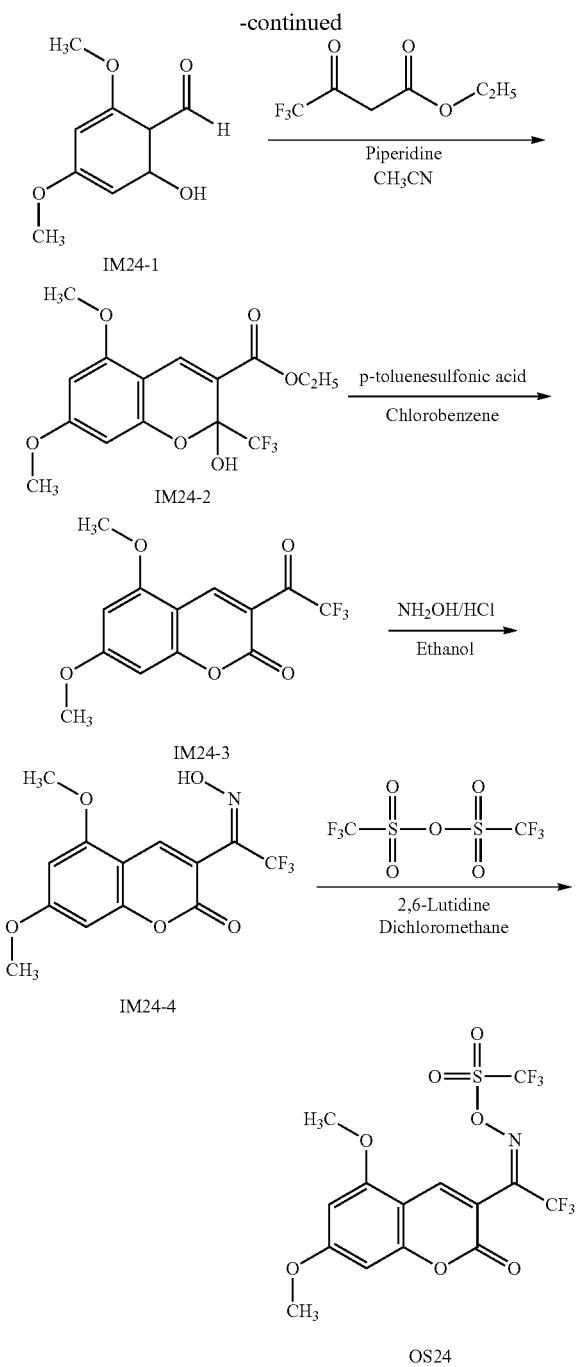

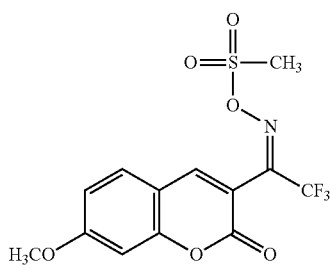

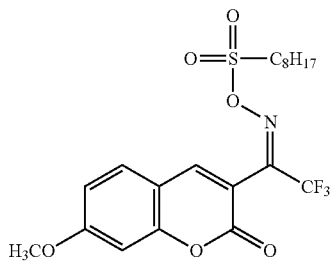

24.1: To 5.18 g of 2,4,6-trimethoxybenzaldehyde in dichlorimethane (60 ml) are added 4.04 g of aluminum chloride and stirred under reflux for 21 hours. The reaction mixture is cooled to room temperature and water and dichloro-methane are added. The organic solvent is collected and the resulting solid is recrystallized from a mixture of dichloro-methane and hexane, giving 3.66 g of IM24-1 as white solid.

24.2: To 3.66 g of IM24-1 and 4.74 g of 4,4,4-ethyl trifluoroacetoace-tate in ace-tonitrile (60 ml) are added 275 mg of piperidine and stirred under reflux for 31 hours. The reaction mixture is cooled to room temperature and water and dichloro-methane are added. The organic solvent is collected and dried under vacuo, giving 6.46 g of IM24-2 as yellow solid. IM24-2 is used to the next step without purification.

24.3: To 6.46 g of IM11-2 in chlorobenzene (60 ml) is added 1000 mg of p-toluenesulfonic acid and stirred under reflux for 22 hours. The solvent is removed by evapora-tion and toluene (30 ml) and water are added to the mixture. The organic layer is sepa-rated from the aq. layer. The solution is refluxed for 3 hours and the resulting water is removed by Dean-Stark trap. After cooling to room temperature the reaction mixture is concentrated. The resulting solid is recrystallized from a mixture of dichloro-methane and hexane, giving 4.772 g of IM24-3 as yellow solid.

24.4: To 4.77 g of IM24-3 in ethanol (15 ml) is added 1.50 g of hydroxyl ammonium chloride and refluxed for 19 hours. After cooling to room temperature, water is added to the reaction mixture. The precipitate is collected by filtration and dried under vacuo, giving 4.46 g of IM24-4 as yellow solid.

24.5: To 0.53 g of IM24-4 in dichloromethane (20 ml) are added 1.35 g of trifluoromethanesulfonic anhydride and 554 mg of 2,6-lutidine at 0° C. After stirring for 15 hours, water is added to the mixture. The reaction mixture is added 20 mL of ethyl acetate, and washed with wa-ter. Organic layer is concentrated and purified by silicagel column chromatography with hexane and dichloromethane as eluent. 1.12 g of OS24 is obtained as yellow solid.

Preparation of OS25

OS25 is prepared according to the same procedure as OS2 except using methenesulfonyl chloride instead of n-propanesulfonyl chloride.

Preparation of OS26

(not representative for the claims)

OS26 is prepared according to the same procedure as OS2 except using n-octanesulfonyl chloride instead of n-pro-panesulfonyl chloride.

Further examples of oxime ester compounds (not representative for the claims), prepared in analogy to the methods as given above are

| | |
|---|---|
| 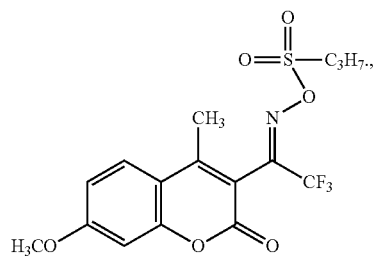 OS5 | 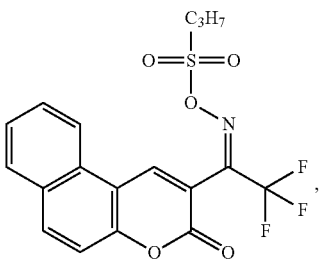 OS7 |
| 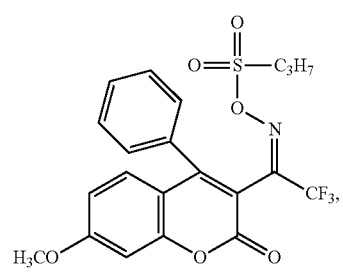 OS6 | 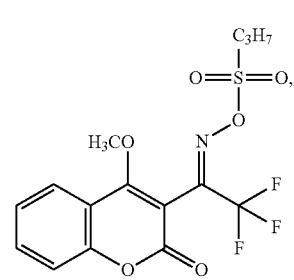 OS8 |
| 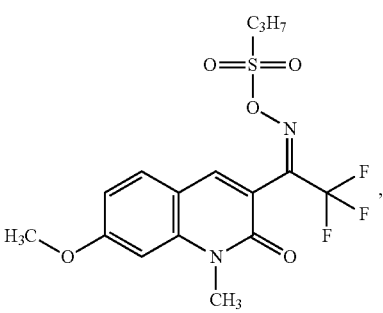 OS10 | 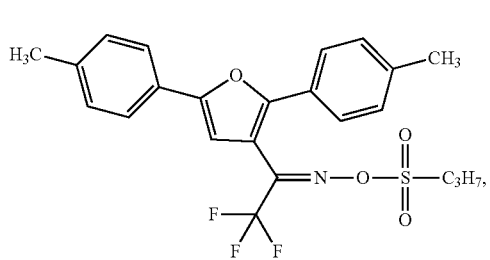 OS13 |
| 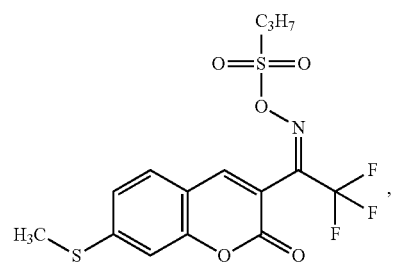 OS9 | 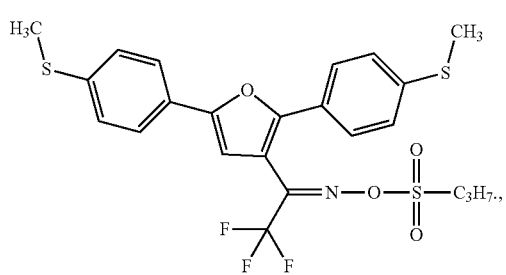 OS14 |
| 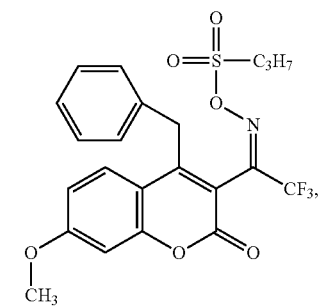 OS12 | 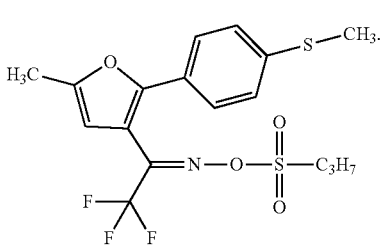 OS15 |

TABLE 1
| Oxime sulfonate(OS) | Structure | ¹H NMR in CDCl₃ |
|---|---|---|
| OS1 | 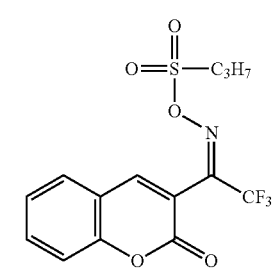 | 1.12(t, 3H), 1.97(m, 2H), 3.41(t, 2H), 7.39(t, 1H), 7.41(d, 1H), 7.60(d, 1H), 7.69(t, 1H), 7.88(s, 1H) |
| OS2 | 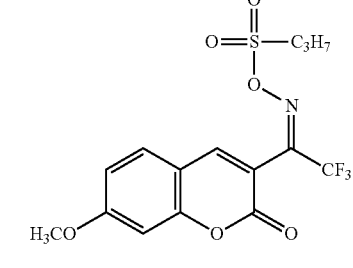 | 1.12(t, 3H), 1.97(m, 2H), 3.40(t, 2H), 3.93(s, 3H), 6.86(s, 1H), 6.94(d, 1H), 7.48(d, 1H), 7.80(s, 1H) |
| OS3 | 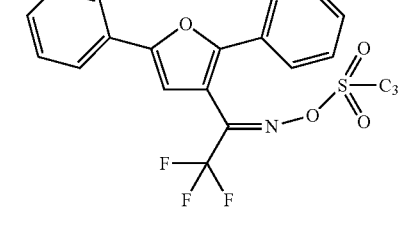 | 0.99(t, 3H), 1.65-1.71(m, 2H) 3.04-3.08(m, 2H), 6.76(m, 1H), 7.33-7.37(m, 1H), 7.42-7.48(m, 5H), 7.57-7.61(m, 2H), 7.72-7.75(m, 2H) |
| OS4 | 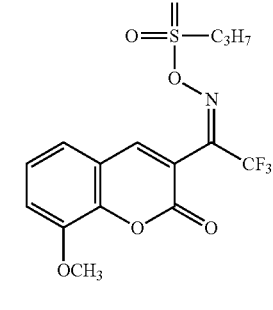 | (in DMSO-d6) 0.98(t, 3H), 1.74(m, 2H), 3.63(t, 2H), 3.92(s, 3H), 7.38-7.43(m, 2H), 7.49(t, 1H), 8.62(s, 1H) |
| OS7 | 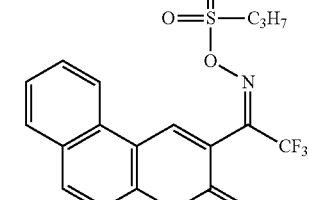 | 1.14(t, 3H), 2.00(m, 2H), 3.44(t, 2H), 7.52(d, 1H), 7.65(t, 1H), 7.77(t, 1H), 7.97(d, 1H), 8.15(d, 1H), 8.22(d, 1H), 8.63(s, 1H) |

TABLE 1-continued
Compound list and physical data thereof
| Oxime sulfonate(OS) | Structure | $^1$H NMR in CDCl$_3$ |
|---|---|---|
| OS11 | 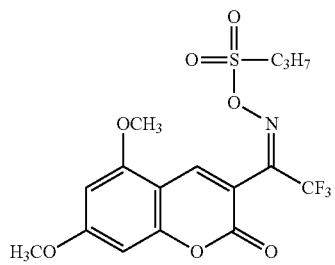 | 1.12(t, 3H), 1.95-2.05(m, 2H), 3.38-3.42(m, 2H), 3.90(s, 3H), 3.93(s, 3H), 6.33(d, 2H), 6.45(d, 1H), 8.13(s, 1H) |
| OS16 | 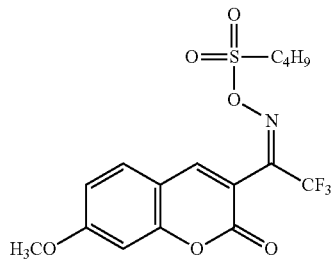 | 0.99(t, 3H), 1.53(m, 2H), 1.92(m, 2H), 3.43(m, 2H), 3.93(s, 3H), 6.86(d, 1H), 6.94(dd, 1H), 7.48(d, 1H), 7.80(s, 1H) |
| OS17 | 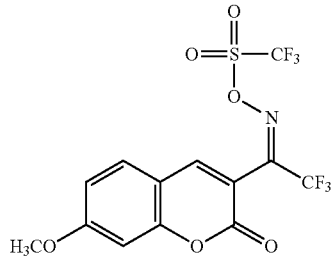 | 3.94(s, 3H), 6.88(d, 1H), 6.96(dd, 1H), 7.51(d, 1H), 7.84(s, 1H) |
| OS24 | 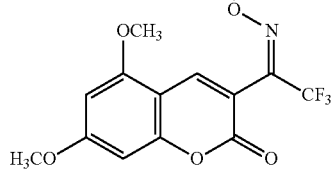 | 3.91(s, 3H) 3.94(s, 3H), 6.34(d, 1H), 6.47(d, 1H), 8.17(s, 1H) |
| OS25 | 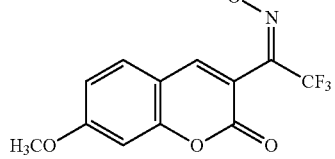 | 3.28(s, 3H), 3.93(s, 3H), 6.87(d, 1H), 6.94(dd, 1H), 7.48(d, 1H), 7.82(s, 1H) |

TABLE 1-continued

Compound list and physical data thereof

| Oxime sulfonate(OS) | Structure | $^1$H NMR in CDCl$_3$ |
|---|---|---|
| OS26 | 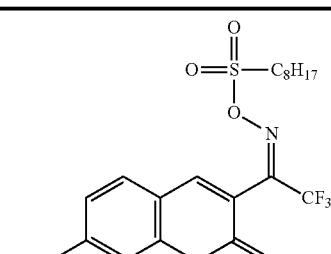 | 0.89(t, 3H), 1.18-1.49(m, 8H), 1.89-1.97(m, 2H), 3.05-3.07(m, 2H), 3.40-3.44(m, 2H), 3.93(s, 3H), 6.86(d, 1H), 6.94(dd, 1H), 7.48(d, 1H), 7.80(s, 1H) |

APPLICATION EXAMPLES

Preparation of the Binder Polymer

To 175.06 g of poly(p-hydorxystyrene), (VP-8000 produced by Nippon Soda Co., LTD., Japan) and 43.9 g of vinyl ethyl ether in tetrahydrofurane (850 ml) are added 78 mg of p-Toluenesulfonic Acid Monohydrate in THF (50 ml). After stirring 14 hours on water bath, the reaction mixture is passed through DIAION CR20 produced by Mitsubishi Chemical Corporation and the DIAION CR20 is washed by tetrahydrofurane (1 L). The combined organic solution is poured into water (15 L) to generate sticky solid. After removing solvents by decantation, 3 L of water is added. After stirring, a white powder is obtained by filtration. After drying at 65° C. for 3 hours followed by 90° C. for 23 hours, 174.8 g of off white solid is obtained.

Preparation of 1-Ethoxyethyl Methacrylate (MAEVE)

To 72.70 g of ethyl vinyl ether are added 0.28 g of phenothiazine and 2.80 g of pyridinium p-toluenesulfonate and 43.70 g of methacrylic acid. After stirring 5.5 hours, 2.50 g of sodium sulfate and 2.83 g of sodium bicarbonate are added to the reaction mixture. The insoluble precipitate is filtered and the mixture is concentrated by evapolator. The crude is purified by distillation under vacuum and 64.42 g of MAEVE is obtained as a colorless oil.

Preparation of Co-Polymer 1

To 7.93 g of MAEVE and 7.11 g of glycidyl methacrylate in 12.50 g of PGMEA is added 1.05 g of V-65 (produced by Wako Pure Chemical Industries, Ltd.) in 10.01 g of PGMEA dropwise at 70'C under a flow of nitrogen. The mixture is stirred for 8.5 hours and a solution of co-polymer 1 is obtained (solid content: 40%). It was found by means of gel permeation chromatography (GPC) that the weight-average molecular weight (Mw) of the co-polymer 1 is 56,000.

Example A1

Photosensitivity is measured in a model photosensitive resin composition under i-line exposure via a bandpass filter (Schott, Germany) with Mask Aligner PLA-501F (Canon, Japan) as an exposure tool. The positive tone resist utilizes the copolymer as prepared above. As for solvent, propylene glycol methyl ether acetate (PGMEA) from Tokyo Kasei Kogyo Co. LTD. is employed. The exact composition of the formulation and the amount of the photoacid generator (PAG) is described in Table 2.

The resist formulations are spin-coated at 1 µm thickness on silicon wafers on which hexamethyldislazane treatment is applied in advance and prebaked at 100° C. for 1 min. After exposure with various exposure doses, no post exposure bake but post exposure delay for 5 min is applied and the resists are then developed in NMD-3 developer from Tokyo Ohka Kogyo Co. Ltd., which is 2.38% aqueous tetramethyl ammonium hydroxide solution, for 1 min.

TABLE 2

| Binder polymer (parts) | 100 |
|---|---|
| PAG (parts) | 2 |
| Solvent (parts) | 400 |

As a measure for photosensitivity, the "Dose to Clear" ($E_0$), which is the dose just sufficient to completely remove the resist film with 1 min development, is determined. The smaller the required dose, the more sensitive is the resist formulation. The results are collected in Table 4 below and demonstrate that the compositions according to the invention are suitable for the preparation of positive tone resists.

Example A2

A formulation for transparency evaluation is prepared with the solution of co-polymer 1 mentioned above (solid content: 40%), PAG and solvent, PGMEA. The exact composition of the formulation is described in Table 3.

TABLE 3

| solution of co-polymer 1 (parts) | 100 |
|---|---|
| PAG (parts) | 0.8 |
| Solvent (parts) | 50 |

The formulations are spin-coated at 700 rpm on glass plates and prebaked at 80° C. for 10 min. Without exposure process, final bake process is applied at 210° C. for 30 min. Thickness of the final cured film is at 3 µm The transparency of the cured film is measured at a wavelength region from 400 to 800 nm with a UV-VIS spectrophotometer, UV-2550 from Shimadzu Corporation. The lowest transmittances as measured are listed in Table 4.

TABLE 4

| Compound of example | $E_0$ [mJ/cm$^2$] | Transparency [%] |
|---|---|---|
| OS1 | 20 | — |
| OS2 | 2.6 | 97.1 |
| OS3 | 6.2 | — |
| OS4 | 21 | — |
| OS11 | 1.7 | 92.3 |
| OS16 | 2.4 | 94.9 |
| OS17 | 1.5 | 98.8 |
| OS24 | 1.0 | 90.4 |
| OS25 | 0.7 | 96.7 |
| OS26 | 17 | 97.7 |

The results show, that the compound of the present invention provides a perfect balance between photosensitivity and transparency, which is in particular benevolent for the formation of insulation layers.

The invention claimed is:

1. A compound of the formula (I)

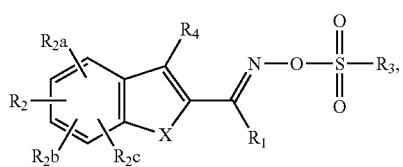

wherein
X is —O(CO)—;
$R_1$ is $C_1$-$C_{12}$haloalkyl or $C_6$-$C_{10}$haloaryl;
$R_2$ is located in position 7 of the coumarinyl ring and is $OR_8$;
$R_2a$, $R_2b$ and $R_2c$ independently of each other are hydrogen;
$R_3$ is $C_1$-$C_8$haloalkyl or $C_1$-$C_8$alkyl;
$R_4$ is hydrogen; and
$R_8$ is $C_1$-$C_6$alkyl.

2. A compound of the formula (I) according to claim 1, wherein the formula (I) is the formula (IA)

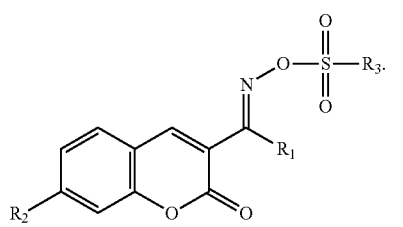

3. A compound of the formula (IA) according to claim 2, wherein
$R_1$ is $C_1$-$C_4$haloalkyl;
$R_2$ is $OR_8$;
$R_3$ is $C_1$-$C_4$haloalkyl or $C_1$-$C_4$alkyl; and
$R_8$ is $C_1$-$C_4$alkyl.

4. A compound of the formula (IA) which is

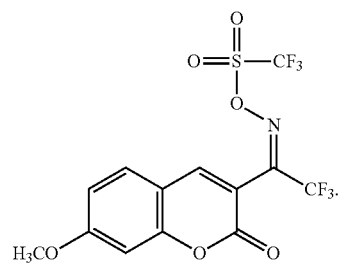

5. A chemically amplified photosensitive resin composition, comprising:
(a) a compound which cures upon the action of an acid, or a compound whose solubility is increased upon the action of an acid; and
(b) as a photosensitive acid donor, the compound of the formula m according to claim 1.

6. A chemically amplified photosensitive resin composition according to claim 5, which is positive tone.

7. A chemically amplified positive photosensitive resin composition according to claim 6, comprising:
(a1) at least one polymer having an acid-labile group which decomposes in the presence of an acid to increase the solubility in aqueous alkaline developer solution; and/or
(a2) at least one monomeric or oligomeric dissolution inhibitor having an acid-labile group which decomposes in the presence of an acid to increase the solubility in aqueous alkaline developer solution; and/or
(a3) at least one alkali-soluble monomeric, oligomeric or polymeric compound; and
(b) as the photosensitive acid donor, the compound of the formula (I).

8. A chemically amplified photosensitive resin composition according to claim 5, which is negative tone.

9. A chemically amplified negative photosensitive resin composition according to claim 8, comprising
(a4) an alkali-soluble resin as binder; and/or
(a6) a solvent-developable resin as binder; and/or
(a5) a component which is cationically or acid-catalytically polymerizable or crosslinkable with itself and/or with the other components; and
(b) as the photosensitive acid donor, at least one the compound of the formula (I).

10. A photosensitive resin composition according to claim 5, further comprising:
a further additive (c), a further photosensitive acid donor compound (b1), other photoinitiator (d), and/or a sensitizer (e).

11. A process for preparing a coating, comprising:
(1) applying to a substrate the composition according to claim 5;
(2) post apply baking the composition at temperatures between 60° C. and 140° C.;
(3) image-wise irradiating with light of wavelengths between 200 nm and 450 nm;
(4) optionally post exposure baking the composition at temperatures between 60° C. and 140° C.;
(5) developing with a solvent or with an aqueous alkaline developer;
(6) optionally flood exposing the coating with light of the wavelengths of between 200 nm and 450 nm; and
(7) baking at a temperature between 90° C. and 250° C.

12. A method for preparing a cured product, comprising:
curing a composition including, as a photosensitive acid donor, the compound of the formula (I) according to claim 1
wherein the cured product is selected from the group consisting of pigmented and non-pigmented coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, insulating layers, passivation layers, interlayer dielectric films, planarization layers, protecting layers, overcoat layers, banks, electroluminescence displays and liquid crystal displays (LCD), waveguides, optical switches, color proofing systems, etch resists, photoresists for manufacturing electronic circuits and displays, electroplating resists, solder resist, photoresist materials for UV and visible laser direct imaging system, photoresist materials for forming dielectric layers in a sequential build-up layer of a printed circuit board, image-recording materials, image-recording materials for recording holographic images, optical information storage or holographic data storage, decolorizing materials, decolorizing materials for image recording materials, image recording materials using microcapsules, magnetic recording materials, micromechanical parts, plating masks, etch masks, glass fibre cable coatings, and microelectronic circuits.

13. An electroluminescence display or liquid crystal display, comprising:
a protective coating or insulating layer or color filter, light shielding layer, black matrix, bank or photo-spacer prepared by the process according to claim 11.

14. An integrated circuit or multilayer circuit, prepared by the process according to claim 11.

15. A photosensitive resin composition, comprising:
a resin (A) comprising a structural unit having an acid dissociative group and a structural unit having a functional group capable of forming a covalent bond by reacting with a carboxyl group or a phenolic hydroxyl group; and
an acid generator (B) represented by the formula (I) according to claim 1,
wherein the resin (A) further comprises at least one structural unit derived from a compound selected from the group consisting of a styrene derivative, a maleimide derivative, (meth)acrylic acid and a hydroxyl group-containing (meth)acrylate.

16. A photosensitive resin composition according to claim 15, wherein the functional group capable of forming a covalent bond by reacting with a carboxyl group or a phenolic hydroxyl group is at least one selected from the group consisting of an epoxy group and an oxetanyl group.

17. A method for forming a cured film, the method comprising:
(1) applying the photosensitive resin composition according to claim 15 onto a substrate to form a photosensitive resin composition layer;
(2) removing a solvent from the photosensitive resin composition layer;
(3) exposing the photosensitive resin composition from which the solvent has been removed to actinic rays in a patterned manner;
(4) developing the exposed photosensitive resin composition with an aqueous developer; and
(5) curing the developed photosensitive resin composition layer after being developed by heating.

18. A cured film formed by the method according to claim 17.

19. A cured film according to claim 18, forming an interlayer dielectric film.

20. An organic EL display device, comprising:
the cured film and a liquid crystal display device comprising the cured film according to claim 18.

* * * * *

UNITED STATES PATENT AND TRADEMARK OFFICE
CERTIFICATE OF CORRECTION

PATENT NO. : 9,994,538 B2
APPLICATION NO. : 15/546699
DATED : June 12, 2018
INVENTOR(S) : Keita Tanaka et al.

It is certified that error appears in the above-identified patent and that said Letters Patent is hereby corrected as shown below:

In the Claims

Column 98, Line 2 "formula m" should read --formula (I)--

Column 98, Line 28 "(b) as the photosensitive acid donor, at least one the" should read --(b) as the photosensitive acid donor, the--

Signed and Sealed this
Twenty-sixth Day of February, 2019

Andrei Iancu
*Director of the United States Patent and Trademark Office*